US009714222B2

(12) United States Patent
Toretsky et al.

(10) Patent No.: US 9,714,222 B2
(45) Date of Patent: *Jul. 25, 2017

(54) METHODS AND COMPOSITIONS FOR TREATING EWINGS SARCOMA FAMILY OF TUMORS

(71) Applicant: GEORGETOWN UNIVERSITY, Washington, DC (US)

(72) Inventors: Jeffrey A. Toretsky, Silver Spring, MD (US); Milton Lang Brown, Brookville, MD (US); Perrer N. Tosso, Rockville, MD (US); Aykut Uren, Rockville, MD (US); Yali Kong, Centreville, VA (US)

(73) Assignee: Georgetown University, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/040,840

(22) Filed: Feb. 10, 2016

(65) Prior Publication Data

US 2016/0159741 A1 Jun. 9, 2016

Related U.S. Application Data

(63) Continuation of application No. 14/388,671, filed as application No. PCT/US2013/036234 on Apr. 11, 2013, now Pat. No. 9,290,449.

(60) Provisional application No. 61/623,349, filed on Apr. 12, 2012.

(51) Int. Cl.
C07D 209/38 (2006.01)
C07D 209/34 (2006.01)

(52) U.S. Cl.
CPC ......... *C07D 209/38* (2013.01); *C07D 209/34* (2013.01)

(58) Field of Classification Search
CPC ........................... C07D 209/38; C07D 209/34
See application file for complete search history.

(56) References Cited

U.S. PATENT DOCUMENTS

| | | | |
|---|---|---|---|
| 6,969,729 | B2 | 11/2005 | Jensen |
| 8,232,310 | B2 | 7/2012 | Toretsky et al. |
| 8,232,410 | B2 | 7/2012 | Ojima et al. |
| 9,045,415 | B2 | 6/2015 | Toretsky et al. |
| 9,290,449 | B2 | 3/2016 | Toretsky et al. |
| 9,511,050 | B2 | 12/2016 | Toretsky et al. |
| 2005/0288244 | A1 | 12/2005 | Manoharan et al. |
| 2010/0004179 | A1 | 1/2010 | Toretsky et al. |
| 2010/0160260 | A1 | 6/2010 | Skordalakes |
| 2010/0167994 | A1 | 7/2010 | Toretsky et al. |
| 2015/0051260 | A1 | 2/2015 | Toretsky et al. |
| 2015/0329488 | A1 | 11/2015 | Toretsky et al. |
| 2016/0102055 | A1 | 4/2016 | Vernier |
| 2016/0263086 | A1 | 9/2016 | Toretsky et al. |

FOREIGN PATENT DOCUMENTS

| | | |
|---|---|---|
| CN | 1365972 A | 8/2002 |
| CN | 103435606 | 12/2013 |
| EP | 0133244 A2 | 2/1985 |
| WO | WO 03/000925 A1 | 1/2003 |
| WO | WO 2006/113864 | 10/2006 |
| WO | WO 2006/117414 A1 | 11/2006 |
| WO | WO 2008/046083 | 4/2008 |
| WO | WO 2008/083326 | 7/2008 |
| WO | WO 2010/083505 | 7/2010 |
| WO | WO 2012/078519 | 6/2012 |

OTHER PUBLICATIONS

Allu et al., "Enantioselective organocatalytic adol reaction of unactivated ketones with isatins," Tetrahedron Letters 52:4080-4083 (2011).
Becerra et al., "Hydrogen-bonding patterns in 3-alkyl-3-hydroxyindolin-2-ones," Acta Cryst. C66:o79-o86 (2010).
Byler et al, "Identification of benzoylisoquinolines as potential anti-Chagas agents," J Bioorg Med Chem. 20:2587-2594 (2012).
Chen et al, "Catalyst-free aldol condensation of ketones and isatins under mild reaction conditions in DMF with molecular sieves 4 A as additive," Green Chem. 11:1465-1476 (2009).
El-Gendy et al., "Synthesis and Antimicrobial Activity of some New 2-Indolinone Derived Oximes and Spiro-Isoxazolines" Arch Pharm Res 23(4):310-314 (2000).
Grigg et al., "Siler Acetate Catalysed Cycloadditions of Isocyanoacetates," Tetrahedron 55:2025-2044 (1999).
Guo et al., "Quinidine Thiourea-catalyzed Aldol Reaction of Unactivated Ketones: Highly Enantioselective Synthesis of 3-Alkyl-3-hyroxy-indolin-2-ones," Angew Chem Int Ed 49:9460-9464 (2010).
Joshi et al., "Studies in Spiro Hetercycles: Part 4: Investigation of the Reactions of Flurointaed 3-Aroylmethylene-indol-2-ones with Hydrazine and Phenylhydrazine and Synthesis of Spiro [indole3,3'-pyrazol]-2-ones," Pharmazle 40:21-22 (1985).
Joshi et al., "Studies in Spiroheterocycles: Part XXVIII: Investigation of the Reaction of 3-Aroylmethyleneindolin-2-Ones with Thiosemicarbazide and Synthesis of SPIRO[3H-INDOLE-3,4'(3'H)-PYRIMIDIN]-2(1H)-ONES," Heterocycles 31(3):473-477 (1990).
Joshi et al., "Investigation of the reaction of 1,3-dihydro-3-(2 0phenyl-2-oxoethylidene)-indol-2(H)-ones with 3-amino-1-phenyl-2-pyrazolin-5-one," Indian J Chem 29B:933-936 (1990).
Joshi et al., "Synthesis and Antibacterial Activity of some Novel Fluorine containing Sipro[3H-indole-3,3'-'3H]-pyrazol]-2(IH)-one Derivatives," J Indian Chem Soc 67:753-756 (1990).
Ibrahim et al., "Synthesis of Spiro Heterocyclic Compounds", E-Journal of Chem. (2010) 7(1):55-58.
IUPAC-IUB [Inter'l Union of Pure and Applied Chemistry—Inter'l Union of Biochemistry} Commission of Biochemical Nomenclature. Appreviated nomenclature of synthetic polypeptides (polymerized amino acids). Revised Recommentations (1971); Biochem. (1972) 11(5):942-944.

(Continued)

*Primary Examiner* — Shawquia Jackson
(74) *Attorney, Agent, or Firm* — Knobbe, Martens, Olson & Bear LLP

(57) ABSTRACT

Compounds, compositions and methods relating to EWS-FLI1 protein inhibitors are provided. The compounds have utility in the treatment of cancers including the Ewing's sarcoma family of tumors.

20 Claims, 24 Drawing Sheets

(56) References Cited

OTHER PUBLICATIONS

Klöck et al., "Acylideneoxoindoles: A new class of reversible inhibitors of human transglutaminase 2," J Bioorg Med Chem Lett. 21:2692-2696 (2011).
Liu et al., "Organocatalytic asymmetric synthesis of 3-difluoroalkyl 3-hyrdrozyoxindoles" Chem Commun. 48:1919-1921 (2012).
López-Alvarado et al., "New Diastereoselective Synthesis of 3-Alkyidene-1-methyloxindoles" Synthesis 1:104-110 (2002).
Lu et al., "Synthesis of planar chiral [2.2] paracyclophane-based amino thioureas and their application in asymmetric aldol reactions of ketones with isatins" Tetrahetron 24:1082-1088 (2013).
Lutz et al., "Acid-Catalyzed Rearrangements of the y-(Methylanilino)lactone of cis-B(p-Bromobenzoyl)-B-methylacrylic Acid, and of trans-b-(p-Bromobenzoyl)acrykuc Methylanilide, to Oxindoles," J Organ Chem. 25(1):193-196 (1960).
Macaev et al., "Synthesis and Structure of New Oxoindoles," Chem Hetero Compounds. 43(3):298-305 (2007).
Nagle et al., "3-(2-Oxoethylidene)indolin-2-one Derivatives Activate Nrf2 and Inhibit NF-xB: Potential Candidates for Chemoprevention," ChemMedChem 9(8):1763-1774 (2014).
Pietra et al., "The stereochemistry of propiophenone addition to isatin," Gazzetta Chimica Italiana 92(XII): 1422-1431 (1962).
Richter et al, "Diazepam-bound GABAA receptor models identify new benzodiazepine binding-site ligands," Nature 8:455-464 (2012).
RN 667914-33-2 (Registry, 2H-Indol-2-one, 4, 7-dichloro-3-[2-(4-aminophenyl)-2-oxoethyl]-1, 3-dihydro-3-hydroxy, Mar. 26, 2004); 1 page.
RN 848688-25-5 (Registry, 2H-Indol-2-one, 4,6-dichloro-3-[2-(2, 4-dimethoxyphenyl)-2-oxoethyl]-1, 3-dihydro-3-hydroxy, Apr. 18, 2005); 1 page.
RN 900016-35-5 (Registry, 2H-Indol-2-one, 7-chloro-1, 3-dihydro-3-hydroxy-3-[2-oxo-2-(3,4,5-trimethoxphenyl) ethyl, Aug. 9, 2006); 1 page.
Registry File(STN), downloaded on Oct. 6, 2016; RN:1180038-32-7; 1146930-25-7; 1144428-37-4; 634174-66-6; 1144428-37-4; 634174-66-6; 442567-87-5; 421584-34-1; 421579-15-9; 421578-89-4; 385394-59-2; 383893-83-2; 370850-15-0; 370848-38-7; 369395-93-7; 362507-29-7, and 362506-54-5.
Registry File(STN), published Aug. 6, 2002, RN:442639-80-7.
Saidalimu et al., "Highly Enantioselective Construction of 3-Hyrdoxy Oxindoles through a Decarboxylative Aldol Additional Trifuoromethyl a-Fluorinated gen-diols to N-Benzyl Isatins," Angew Chem Int. Ed. 52:5566-5570 (2013).
Segura-Cabrera et al., "Structure-based prediction of *Mycobacterium tuberculosis* shikimate kinase inhibitors by high-throughput virtual screening," Bioorg Med Chem Lett. 18:3152-3157 (2008).
Yu et al., "Highly Efficient 'On Water' Catalyst-Free Neucleophilic Addition Reactions Using Difluoroenoxysilanes: Dramatic Flourine Effects," Angew Chem Int. Ed 53:9512-9516 (2014).
Zhong et al., "Molecular sieve mediated decarboxylative Mannich and aldol reactions of B-ketoacids," Tetrahedron Lett. 54:4333-4336 (2013).
National Center for Biotechnology Information. (PubChm Substance Database; SID=862348, (https://pubchem.ncbi.nlm.nih.gov/substance/862348; downloaded Jan. 2, 207); available Jun. 29, 2005; 8 pages.
Abaan et al., "PTPL1 is a direct transcriptional target of EWS-FLI1 and modulates Ewing's sarcoma tumorigenesis", Oncogene (2005) 24(16): 2715-2722.
Anderson et al., "BRCA1 protein is linked to the RNA polymerase II holoenzyme complex via RNA helicase A", Nat Genet (1998) 19(3):254-256.
Ankhiwala, Studies in Spiroheterocycles. Synthesis and Antimicrobial Activities of Some New Spiro (indoline-3, 5'-pyrazonlin)-1'-phenyl-2-ones and Spiro ( . . . J Indian Chem Soc. (1990) 67: 432-434.

Babu et al., "Heteropolyacid-silica mediated [3+2] cycloaddition of ylides—a facile multicomponent one-pot synthesis of novel dispiroheterocycles", Tetrahedron Ltt. (2006) 47(52): 9221-9225.
Baer et al., "Profiling and functional annotation of mRNA gene expression in pediatric rhabdomyosarcoma and Ewing's sarcoma", Int J Cancer (2004) 110(5):687-694.
Bayoumy et al., "Studies on Spiroheterocyclic Nitrogen Compounds. Part 1: Synthesis of Some New Spiro Pyrazolines, Isoxazolines and Pyrimidinethiones Containing Benzanilide Moiety", J Indian Chem Soc. (1984) LXI(1):520-522.
Beccalli et al., "Synthesis of [a]annulated carbazoles from indol-2,3-dione." Tetrahedron (1993) 49(21): 4741-4758.
Berg et al., "Small-molecule antagonists of Myc/Max dimerization inhibit Myc-induced transformation of chicken embryo fibroblasts", Proc Natl Acad Sci U S A (2002) 99(6):3830-3835.
Bhalla et al., "Local flexibility in molecular function paradigm", Mol Cell Proteomics (2006) 5:1212-1223.
Bowdish et al., "Immunomodulatory properties of defensins and cathelicidins", Curr Top Microbiol Immunol (2006) 306:27-66.
Braun et al., "Identification of target genes for the Ewing's sarcoma EWS/FLI fusion protein by representational difference analysis", Mol Cell Biol (1995) 15(8):4623-4630.
Carter et al., "Chemotherapy of Cancer", 2nd Edition; John Wiley & Sons, New York (1981), Appendix C—Drug-Tumor Interactions; 5 pages.
Castillero-Trejo et al., "Expression of the EWS/FLI-1 oncogene in murine primary bone-derived cells results in EWS/FLI-1-dependent, Ewing sarcoma-like tumors", Cancer Res (2005) 65(19):8698-8705.
Chen et al., "Specific alterations of U1-C protein or U1 small nuclear RNA can eliminate the requirement of Prp28p, an essential DEAD box splicing factor", Mol Cell (2001) 7(1):227-232.
Cheng et al., "Rational drug design via intrinsically disordered protein", Trends Biotechnol. (2006) 24(10):435-442.
Dandia et al., "Investigation of the Reactions of some New Fluorine containing 3-Aroylmethylene-indol-2-ones with Urea and Thiourea Derivatives", J Indian Chem Soc., (Nov. 1995) 72: 833-835.
Dandia et al., "Facile One Pot Microwave Induced Solvent-Free Synthesis and Antifungal, Antitubercular Screening of Spiro [1,5]-Benzothiazepin-2,3'[3'H]indol-2[1'H]ones", Chem Pharm Bull (2003) 51(10): 1137-1141.
Database accession No. CID 359736, 3-[2-(4-Amino-phenyl)-2-oxo-ethyl]-3-hydroxy-1,3-dihydro-indol-2-one—Compound Summary; (Mar. 26, 2005) XP-002717179; Database PubChem Compound; pp. 1-5.
Database accession No. CID 326411; NSC297830—Compound summary; XP-002717181; (Mar. 26, 2004) Database PubChem Compound; pp. 1-5.
Database accession No. CID 366668, NSC635343—Compound summary; XP-002717180; (Mar. 26, 2005) Database PubChem Compound; pp. 1-3.
Database accession No. CID 366694, NSC635411—Compound summary; (Mar. 6, 2005) Database PubChem Compound; pp. 1-3.
Database accession No. CID 398900, NCI60_038544—Compound summary; (May 30, 2009) Database PubChem Compound; pp. 1-2.
Database accession No. CID 703160, ZINC00085926—Compound summary; (Jul. 8, 2005) Database PubChem Compound; pp. 1-2.
Database accession No. CID 772922, ZINC00257314—Compound summary; (Jul. 8, 2005) Database PubChem Compound; pp. 1-2.
Database accession No. CID 797457, ZINC00302255—Compound summary; (Jul. 9, 2005) Database PubChem Compound; pp. 1-2.
Database accession No. CID 797741, ZINC00302664—Compound summary; (Jul. 9, 2005) Database PubChem Compound; pp. 1-2.
Database accession No. CID 1149577, ZINC00894999—Compound summary; (Jul. 10, 2005) Database PubChem Compound; pp. 1-2.
Database accession No. CID 1517002, ZINC01439946—Compound summary; (Jul. 11, 2005) Database PubChem Compound; pp. 1-2.
Database accession No. CID 51703682, ZINC35686355—Compound summary; (May 5, 2011) Database PubChem Compound; pp. 1-2.

(56) References Cited

OTHER PUBLICATIONS

Database accession No. RN 362506-54-5; XP-002745329; (Oct. 16, 2001) Supplier: ChemBridge Corporation; 1 page.
Database accession No. RN 362507-29-7; XP-002745330; (Oct. 16, 2001) Supplier: Interbioscreen Ltd.; 1 page.
Database accession No. RN 1144428-37-4; XP-002745331; (May 8, 2009) Supplier: Interbioscreen Ltd.; 1 page.
Delattre et al., "The Ewing family of tumors—a subgroup of small-round-cell tumors defined by specific chimeric transcripts", N Engl J Med (1994) 331(5):294-299.
Demichelis et al., TMPRSS2: ERG gene fusion associated with lethal cancer in a watchful waiting cohort, Oncogene (2007) 26:4596-4599.
Derossi et al., "The third helix of the Antennapedia homeodomain translocates through biological membranes", J Biol Chem (1994) 269(14):10444-10450.
Erkizan et al., "A small molecule blocking oncogenic protein EWS-FLI1 interaction with RNA helicase A inhibits growth of Ewing's sarcoma", Nat Med. (2009) 15(7): 750-756.
Feldmann et al., "Blockage of hedgehog signaling inhibits pancreatic cancer invasion and metastases: A new paradigm for combination therapy in solid cancers", Cancer Res. (2007) 67:2187-2196.
Frangioni et al., "Use of a general purpose mammalian expression vector for studying intracellular protein targeting: identification of critical residues in the nuclear lamin A/C nuclear localization signal", J Cell Sci (1993) 105(Pt. 2):481-488.
French et al., "Midline carcinoma of children and young adults with NUT rearrangement", J Clin Oncol (2004) 22(20):4135-4139.
Fujii et al., "An antagonist of dishevelled protein-protein interaction suppresses beta-catenin-dependent tumor cell growth", Cancer Res (2007) 67(2):573-579.
Gadek et al., "Small molecule antagonists of proteins", Biochem Pharmacol (2003) 65(1):1-8.
Gangwal et al., "Microsatellites as EWS/FLI response elements in Ewing's sarcoma", Proc Natl Acad Sci U S A (2008) 105(29):10149-10154.
Garden et al., "A versatile synthetic methodology for the synthesis of tryptophols", Tetrahedron (2002) 58(42):8399-8412.
Golub et al., "Molecular Classsification of Cancer: Class Discovery and Class Prediction by Gene Expression Monitoring", Science (1999) 286: 531-537.
Grier et al., "Addition of ifosfamide and etoposide to standard chemotherapy for Ewing's sarcoma and primitive neuroectodermal tumor of bone", N Engl J Med (2003) 348(8):694-701.
Gyurkocza et al., "Antileukemic activity of shepherdin and molecular diversity of hsp90 inhibitors", J Natl Cancer Inst (2006) 98(15):1068-1077.
Hartman et al., "RNA helicase A is necessary for translation of selected messenger RNAs", Nat Struct Mol Biol. (2006) 13:509-516.
Helman et al., "Mechanisms of sarcoma development", Nat Rev Cancer (2003) 3(9):685-694.
Hu-Lieskovan et al., "Sequencespecific knockdown of EWS-FLI1 by targeted, nonviral delivery of small interfering RNA inhibits tumor growth in a murine model of metastatic Ewing's sarcoma", Cancer Res (2005) 65:8984-8992.
Joshi et al., "Synthesis and central nervous system activities of certain fluorine-containing 3-substituted indol-2-ones." Pharmazie (1984) 39(3): 153-155.
Kaiser, J., "First Pass at Cancer Genome Reveals Complex Landscape", Sciene (2006) 313:1370.
Khan et al., "Classification and diagnostic prediction of cancers using gene expression profiling and artificial neural networks", Nat Med (2001) 7(6):673-679.
Kidwai et al., "Microwave-induced "solvent-free" novel technique for the synthesis of spiro [indole-pyrazole/isoxazole/pyrimidine] derivatives", Oxidation Communications (2001) 24(2): 287-290.
Kinsey et al., "NR0B1 is required for the oncogenic phenotype mediated by EWS/FLI in Ewing's sarcoma", Mol Cancer Res (2006) 4(11):851-859.

Knoop et al., "The splicing factor U1C represses EWS/FLI-mediated transactivation", J Biol Chem (2000) 275(32):24865-24871.
Knoop et al., "EWS/FLI alters 5'-splice site selection", J Biol Chem (2001) 276(25):22317-22322.
Kobayashi et al., "Studies on Indole Derivatives—Synthesis of 3-Phenyl-9H-pyridazino[3,4-b]indole Derivatives", Chem Pharm Bull. (1964) 12(10):1129-1135.
Kovar et al., "EWS/FLI-1 antagonists induce growth inhibition of Ewing tumor cells in vitro", Cell Growth Differ (1996) 7(4):429-437.
Kovar et al., "Potentials for RNAi in sarcoma research and therapy: Ewing's sarcoma as a model", Semin Cancer Biol. (2003) 13:275-281.
Krontiris et al., "Internal Medicine", 4th Edition, Elsevier Science (1994) Chapters 71-72, pp. 699-729.
Lala et al., "Role of nitric oxide in tumor progression: Lessons from experimental tumors", Cancer Metastasis Rev. (1998) 17(1): 91-106.
Lambert et al., EWS FLI-1 antisense nanocapsules inhibits Ewing sarcoma-related tumor in mice, Biochem Biophys Res Commun. (2000) 279(2):401-406.
Lang et al., "Identification of peptide mimetics of xenoreactive alpha-Gal antigenic epitope4 by phage display", Biochem Biophys Res Commun (2006) 306:27-66.
Lee et al., "RNA helicase A is essential for normal gastrulation", Proc Natl Acad Sci U S A (1998) 95(23):13709-13713.
Leeson et al., "The influence of drug-like concepts on decision-making in medicinal chemistry", Nature reviews (2007) 6(11):881-890.
Lessnick et al., "The Ewing's sarcoma oncoprotein EWS/FLI induces a p53-dependent growth arrest in primary human fibroblasts", Cancer Cell (2002) 1(4):393-401.
Li et al., "Control of apoptosis and mitotic spindle checkpoint by survivin", Nature (1998) 396(6711):580-584.
Lindgren et al., "Translocation properties of novel cell penetrating transportan and penetratin analogues", Bioconjug Chem (2000) 11(5):619-626.
Iost et al., "mRNAs can be stabilized by DEAD-box proteins", Nature (1994) 372(6502):193-196.
Maitra et al., "Detection of t(11;22)(q24;q12) Translation and EWS-FLI-1 Fusion Transcript in a Case of Solid Pseudopapillary Tumor of the Pancreas", Ped Develop Pathol. (2000) 3:603-605.
Maksimenko et al., "Oligonucleotides targeted against a junction oncogene are made efficient by nanotechnologies", Pharm Res (2003) 20(10):1565-1567.
Mateo-Lozano et al.; Rapamycin induces the fusion-type independent downregulation of the EWS/FLI-1 proteins and inhibits Ewing's sarcoma cell proliferation; Oncogene (2003) 22(58):9282-9287.
May et al., "Ewing sarcoma 11;22 translocation produces a chimeric transcription factor that requires the DNA-binding domain encoded by FLI1 for transformation", Proc Natl Acad Sci U S A (1993) 90(12):5752-5756.
May et al., "The Ewing's sarcoma EWS/FLI-1 fusion gene encodes a more potent transcriptional activator and is a more powerful transforming gene than FLI-1", Mol Cell Biol. (1993) 13(12):7393-7398.
Mcintyre et al., "Design and cloning strategies for constructing shRNA expression vectors", BMC Biotechnol. (2006) 6:1.
Medlineplus; Cancer [online]; [retrieved on Jul. 6, 2007] URL—http://www.nlm.nik.gov/medlineplus/cancer.html. 10 pages.
Merchant et al., "Potential use of imatinib in Ewing's sarcoma: evidence for in vitro and in vivo activity", J Natl Cancer Inst (2002) 94(22):1673-1679.
Merchant et al., Interferon gamma enhances the effectiveness of tumor necrosis factor-related apoptosis—Inducing ligand receptor agonists in a xenograft model of Ewing's sarcoma., Cancer Res (2004) 64(22):8349-8356.
Murray et al., "Targeting protein-protein interactions: Lessons from p53/MDM2", Biopolymers (2007) 88(5):657-686.
Myohanen et al., "Sequence-specific DNA binding activity of RNA helicase A to the p16INK4a promoter", J Biol Chem (2001) 276(2):1634-1642.

(56) References Cited

OTHER PUBLICATIONS

Nakajima et al., "RNA helicase A mediates assocation of CBP with RNA polymerase II", Cell (1997) 90(6):1107-1112.
Nakatani et al., "Identification of p21WAF1/CIP1 as a direct target of EWS-Fli1 oncogenic fusion protein", J Biol Chem (2003) 278(17):15105-15115.
Ng et al., "Multiple aromatic side chains within a disordered structure are critical for transcription and transforming activity of EWS family oncoproteins", Proc Natl Acad Sci U S A (2007) 104(2):479-484.
Ojida et al., "Highly enantioselective reformatsky reaction of ketones: Chelation-assisted enantio face discrimination", Org Lett (2002) 4(18):3051-3054.
Ouchida et al., "Loss of tumorigenicity of Ewing's sarcoma cells expressing antisense RNA to EWS-fusion transcripts", Oncogene (1995) 11(6):1049-1054.
Pagliaro et al., "Emerging classes of protein-protein interaction inhibitors and new tools for their development", Curr Opin Chem Biol. (2004) 8(4):442-449.
Pajouhesh et al., "Potential Anticonvulsants VI: Condensation of Isatins with Cyclohexonone and Other Cyclic Ketones", J Pharma Sciences (1983) 72(3):318-321.
Palermo et al., "The AF4-mimetic peptide, PFWT, induces necrotic cell death in MV4-11 leukemia cells", Leuk Res. (2008) 32(4):633-42.
Perez et al., "Antennapedia homeobox as a signal for the cellular internalization and nuclear addressing of a small exogenous peptide", J Cell Sci (1992) 102(Pt. 4):717-722.
Petermann et al., "Oncogenic EWS-Fli1 interacts with hsRPB7, a subunit of human RNA polymerase II", Oncogene (1998) 17:603-610.
Plescia et al., "Rational design of shepherdin, a novel anticancer agent", Cancer Cell (2005) 7(5):457-468.
Popp et al., "Synthesis of 3-Hydroxy-3-phenacyloxindole Analogs", J Pharma Science (1979) 68(4):519-520.
Poppe et al., "Expression analyses identify MLL as a prominent target of 11q23 amplification and support an etiologic role for MLL gain of function in myeloid malignancies", Blood (2004) 103(1):229-235.
Pui et al., "Clinical heterogeneity in childhood acute lymphoblastic leukemia with 11q23 rearrangements", Luekemia (2003) 17(4):700-706.
Pui et al., "Acute lymphoblastic leukemia", N Engl J Med (2004) 350(15):1535-1548.
Rahim et al., "YK-4-279 Inhibits ERG and ETV1 Mediated Prostate Cancer Cell Invasion", PLoS One (2011) 6(4):e19343; 8 pages.
"Remington's Pharmaceutical Sciences", Mack Publishing Company 19th edition (1995).
Riggi et al., "Ewing's sarcoma—Like tumors originate from EWS-FLI-1-expressing mesenchymal progenitor cells", Cancer Res (2006) 66(19):9786.
Righetti et al., "Heterodiene Syntheses. Part 21. etc.". J Chem Soc., Perkin Transactions I, (1979) 4: 863-868.
RN 667914-27-4 (Registry, 2H-Indol-2-one, 3-[2-(4-aminophenyl)-2-oxoethyl]-5, 7-dichloro-1, 3-dihydro-3-hydroxy, Mar. 26, 2004); 1 page.
RN 672338-27-1 (Registry, 2H-Indol-2-one, 4, 6-dichloro-1, 3-dihydro-3-hydroxy-3-[2-(3-nitrophenyl)-2-oxoehyl], Apr. 7, 2004); 1 page.
RN 6938523-27-7 (Registry, 2H-Indol-2-one, 7-bromo-1,3-dihydro-3-hydroxy-3-[2-(4-methoxyphenl)-2-oxoethyl]-5-methyl, Jun. 16, 2004); 1 page.
RN 909225-77-0 (Registry, 2H-Indol-2-one, 7-chloro-3-[2-(4-ethylphenyl)-2-oxoethyl]-1,3-hydroxy, Oct. 2, 2006); 1 page.
RN 692281-43-9 (Registry, 2H-Indol-2-one, 4-chloro-3-[2-(4-fluorophenyl)-2-oxoethyl]-1,3-dihydro-3-hydroxy-7-methyl, Jun. 13, 2004); 1 page.
RN 848755-10-2 (Registry, 2H-Indol-2-one,4,6-dichloro-3-[2-(3,4-dimethoxyphenyl)-2-oxoethyl]-1,3-dihydro-3-hydroxy, Apr. 19, 2005); 1 page.
Sanchez et al., "Alteration of cyclin D1 transcript elongation by a mutated transcription factor up-regulates the oncogenic D1b splice isoform in cancer", Proc Natl Acad Sci U S A. (2008) 105(16):6004-6009.
Sillerud et al., "Design and structure of peptide and peptidomimetic antagonists of protein-protein interaction", Curr Protein Pept Sci (2005) 6(2):151-169.
Smith et al., "Expression profiling of EWS/FLI identifies NKX2.2 as a critical target gene in Ewing's sarcoma", Cancer Cell (2006) 9(5):405-416.
Snyder et al., "Treatment of terminal peritoneal carcinomatosis by a transducible p53-activating peptide", PLos Biol (2004) 2(2):0186-0193.
Srinivasan et al., "The synthetic peptide PFWT disrupts AF4-AF9 protein complexes and induces apoptosis in t(4;11) leukemia cells", Leukemia (2004) 18(8):1364-1372.
Stegmaier et al., "Signature-based small molecule screening identifies cytosine arabinoside as an EWS/FLI modulator in Ewing sarcoma", PLoS medicine (2007) 4(4):e122.
Strigacova et al., "Novel oxindole derivatives and their biological activity", Folia Microbiol (Praha). (2001) 46(3):187-192.
Subramanian et al., "Gene set enrichment analysis: a knowledge-based approach for interpreting genome-wide expression profiles", Proc Natl Acad Sci U S A. (2005) 102(43):15545-15550.
Tanaka et al., "EWS-Fli1 antisense oligodeoxynucleotide inhibits proliferation of human Ewing's sarcoma and primitive neuroectodermal tumor cells", J Clin Invest (1997) 99(2):239-247.
Terrone et al., "Penetratin and related cell-penetrating cationic peptides can translocate across lipid bilayers in the presence of a transbilayer potential", Biochem. (2003) 42(47):13787-13799.
Tetsuka et al., "RNA helicase A interacts with nuclear factor kappaB p65 and functions as a transcriptional coactivator", Eur J Biochem (2004) 271(18):3741-3751.
Thoren et al., "The antennapedia peptide penetratin translocates across lipid bilayers—the first direct observation", FEBS Lett (2000) 482(3):265-268.
Tiemann et al., "Solid pseudopapillary neoplasms of the pancreas are associated with FLI-1 expression, but not with EWS/FLI-1 translocation." Mod Pathol. (2006) 19(11):1409-1413.
Torchia et al., "EWS/FLI-1 induces rapid onset of myeloid/erythroid leukemia in mice", Mol Cell Biol (2007) 27(22):7918-7934.
Toretsky et al., "Inhibition of EWS-FLI-1 fusion protein with antisense oligodeoxynucleotides", J Neurooncol. (1997) 31(1-2):9-16.
Toretsky et al., "Phosphoinositide 3-hydroxide kinase blockade enhances apoptosis in the Ewing's sarcoma family of tumors", Cancer Res (1999) 59(22):5745-5750.
Toretsky et al., "Glypican-3 expression in wilms tumor and hepatoblastoma", J Pediatr Hematol Oncol. (2001) 23(8):496-499.
Toretsky et al., "Oncoprotein EWS-FLI1 activity is enhanced by RNA helicase A", Cancer Res (2006) 66(11):5574-5581.
Üren et al., "Recombinant EWS-FLI1 oncoprotein activates transcription", Biochem. (2004) 43(42):13579-13589.
Üren et al., "Activation of the canonical Wnt pathway during genital keratinocyte transformation: a model for cervical cancer progression", Cancer Res (2005) 65(14):6199-6206.
Üren et al., "Ewing's Sarcoma Oncoprotein EWS-FLI1: The Perfect Target without a Therapeutic Agent", Future Onc. (2005) 1(4):521-528.
Üren et al., "Pediatric malignancies provide unique cancer therapy targets", Curr Opin Pediatr. (2005) 17:14-19.
Välineva et al., "Characterization of RNA helicase A as component of STAT6-dependent enhanceosome", Nucleic Acids Res (2006) 34(14):3938-3946.
Velikorodov et al., "Some Condensations of Methyl 4-Acetylphenylcarbamate", Russian J Org Chem (2010) 46(7):971-975.
Velikorodov et al., "Synthesis of New Spiro Compounds Containing a Carbamate Group", Russian J Org Chem. (2010) 46(12):1826-1829.

(56) References Cited

OTHER PUBLICATIONS

Velikorodov et al., "Synthesis of 3-Pyrrol-3'-yloxindoles with a Carbamate Function", Russian J Org Chem. (2011) 47(11):1715-1717.
Velikorodov et al., "L-Proline-Catalyzed 1,3-Dipolar Cycloaddition of Some Schiff Bases to Methyl 4-[1-Oxo-2(2-oxo-2,3-dihydrolH-indol-3-ylidene)ethyl]phenylcarbamate", Russian J Org Chem. (2011) 47(10):1596-1597.
Velikorodov et al., "Three-Component Synthesis of Spiro Compounds with a Carbamate Functionality", Russian J Org Chem. (2011) 47(3):402-404.
Von Hippel et al., "A general model for nucleic acid helicases and their "coupling" within macromolecular machines", Cell (2001) 104(2):177-190.
Walensky et al., "Activation of apoptosis in vivo by a hydrocarbon-stapled BH3 helix", Science (2004) 305(5689):1466-1470.
Wikipedia—Cancer [online]; [retrieved on Jul. 6, 2007]. URL; http://en.wikipedia.org/wiki/Cancer; 2 pages.
Xie et al., "Functional anthology of intrinsic disorder. 1. Biological processes and functions of proteins with long disordered regions", J Proteome Res. (2007) 6(5):1882-1898.
Yin et al., "Low molecular weight inhibitors of Myc-Max interaction and function", Oncogene (2003) 22(40):6151-6159.
Zhang et al., "Multiple functions of nuclear DNA helicase II (RNA helicase A) in nucleic acid metabolism", Acta Biochim Biophys Sin (Shanghai) (2004) 36(3):177-183.
Zhong et al., "RNA helicase A in the MEF1 transcription factor complex upregulates the MDR1 gene in multidrug-resistant cancer cells", J Biol Chem (2004) 279(17):17134-17141.
International Search Report and Written Opinion dated Jul. 31, 2013 for International Patent Application No. PCT/US2013/036234, filed Apr. 11, 2013.
European Supplemental Search Report dated Oct. 21, 2015 for Application No. 13776244.9, filed Nov. 6, 2014.

METHODS AND COMPOSITIONS FOR TREATING EWINGS SARCOMA FAMILY OF TUMORS

RELATED APPLICATIONS

This application is a continuation of U.S. Ser. No. 14/388,671 filed Sep. 26, 2014 entitled "METHODS AND COMPOSITIONS FOR TREATING EWINGS SARCOMA FAMILY OF TUMORS" which is the U.S. National Phase of PCT/US2013/036234 filed Apr. 11, 2013 published in English on Oct. 17, 2013 as WO 2013/155341 which claims the benefit of U.S. Prov. App. No. 61/623,349 entitled "METHODS AND COMPOSITIONS FOR TREATING EWINGS SARCOMA FAMILY OF TUMORS" filed on Apr. 12, 2012, the contents of which are incorporated herein by reference in their entireties.

STATEMENT REGARDING FEDERALLY SPONSORED R&D

This invention was made with government support under NIH Grant/Contract Numbers R01CA138212 and R01CA133662 awarded by the National Institutes of Health of the United States of America. The government has certain rights in the invention.

FIELD OF THE INVENTION

Compounds compositions, and methods are provided related to EWS-FLI1 protein inhibitors are provided. The compounds have utility in the treatment of cancers including the Ewing's sarcoma family of tumors.

BACKGROUND OF THE INVENTION

The Ewing's Sarcoma Family of Tumors (ESFT) are highly aggressive tumors that occur in children, adolescents and young adults in the bone and the soft tissues. They respond to chemotherapy, yet 75% to 80% of the patients who have developed metastatic ESFTs will die in five years despites high doses of chemotherapy (Grier, H. E et al., N. Engl. J. Med. 348, 694-701 (2003)). ESFTs contain a well characterized chromosomal translocation. This joins the Ewing's sarcoma gene (EWS), located on chromosome 22, to an ets family gene, often friend leukemia insertion (FLI)1 located on the chromosome 11, t(11:22) which lead to the expression of various fusion proteins (Aykut Uren, Jeffrey A Torestsky Ewing's sarcoma oncoproteins EWS-FLI1: the perfect target without a therapeutic agent, Future Oncol. 1(4), 521-528 (2005)).

In vitro and in vivo studies have demonstrated that the elimination of the oncoprotein, EWS-FLI1, leads to a decrease proliferation of ESTF cell lines and a decrease of tumor volume. EWS-FLI1 lacks enzymatic activity, however, the RHA helicase A (RHA) increases EWS-FLI1-modulated oncogenesis, therefore the protein-protein interactions between the two proteins is required for the maintenance of the tumor growth (Hyariye N Erkizan et al. A small molecule blocking oncogenic protein EWS-FI1 interacting with RHA helicase A inhibits growth of Ewing's sarcoma. Nature Medicine 15(7) 750-756 (2009)). The paradigm of disrupting key protein interactions may have utility in treatment of diseases including sarcomas with similar translocations, and leukemias with MLL translocations ((Helman L J, Meltzer P. Mechanisms of sarcoma development. Nat Rev Cancer 2003; 3(9):685-94); and Pui C H, Relling M V, Downing J R. Acute lymphoblastic leukemia. N Engl J Med 2004; 350(15):1535-48). Moreover, disordered proteins may be excellent therapeutic targets based on their intrinsic biochemical properties (Cheng Y, LeGall T, Oldfield C J, et al. Rational drug design via intrinsically disordered protein. Trends Biotechnol 2006; 24(10):435-42).

Despite years of in vitro and xenograft studies with antisense and siRNA directed towards EWS-FLI1, none of these is heretofore practical as a human therapy based on inadequate delivery and stability. Accordingly, there is a need for improved therapies to treat disorders such as ESFTs.

SUMMARY OF THE INVENTION

Some embodiments relate to a compound having a formula:

Formula (I)

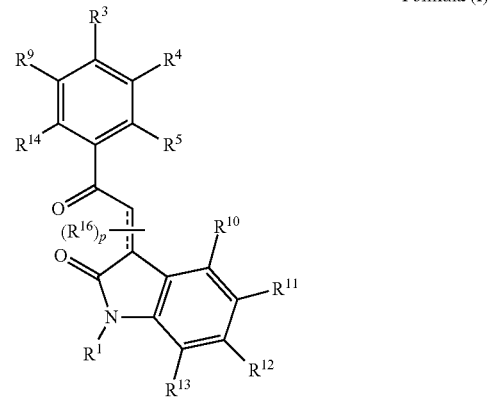

or a pharmaceutically acceptable salt thereof,
wherein $R^1$ is selected from the group consisting of hydrogen, $C_{1-6}$ alkyl, one amino acid, two amino acids linked together, three amino acids linked together,

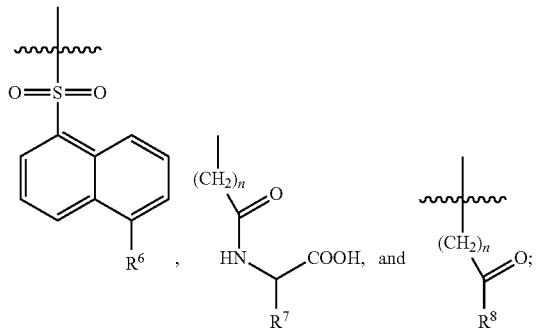

$R^3$, $R^4$, $R^5$, $R^9$, and $R^{14}$ are each independently selected from the group consisting of hydrogen, halogen, $C_{1-6}$ alkyl, $C_{1-6}$ alkoxy, —C(=O)NH$_2$, —NO$_2$, —NH$_2$, —OH, —NH($R^{15}$), —N($R^{15})_2$, and —S$R^{15}$; $R^{10}$, $R^{11}$, $R^{12}$, and $R^{13}$ are each independently selected from the group consisting of hydrogen, halogen, $C_{1-6}$ alkyl, $C_{1-6}$ alkoxy, —C(=O)NH$_2$, —NO$_2$, —NH$_2$, —OH, —NH($R^{15}$), —N($R^{15})_2$, and —S$R^{15}$; $R^6$ is $C_{1-6}$ dialkyl amine; $R^7$ is selected from the group consisting of hydrogen and $C_{1-6}$ alkyl; $R^8$ and $R^{15}$ are each independently $C_{1-6}$ alkyl; each $R^{16}$ is independently hydrogen, —OH, or $C_{1-6}$ alkoxy; n is an integer from 0 to 4; p is 1 or 3; and the dashed line represents an optional double bond where said double bond has a configuration selected from the group consisting of cis and trans, with the proviso that at least one of $R^3$, $R^4$, $R^5$, $R^9$, and $R^{14}$ is selected from the group consisting of —NH($R^{15}$), —N($R^{15}$)$_2$, and —S$R^{15}$.

In some embodiments, the compound of Formula I may be a compound having the structure of Formula Ia:

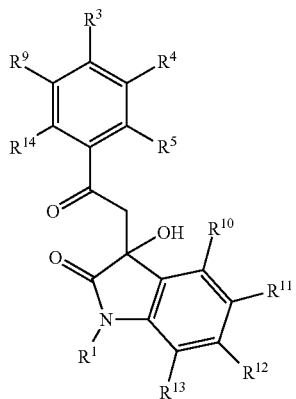

(Ia)

or a pharmaceutically acceptable salt thereof.

In some embodiments, the compound of Formula I may be a compound having the structure of Formula Ib:

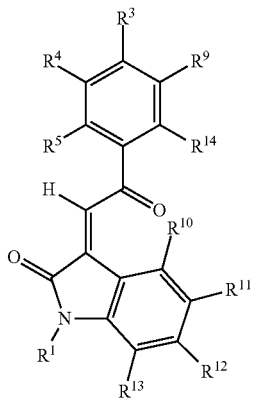

(Ib)

or a pharmaceutically acceptable salt thereof.

In some embodiments, $R^1$ is selected from the group consisting of Leu, Leu-Asp, Leu-Asp-Ala, —CH$_2$—C(=O)—NHCH$_2$COOH, —CH$_2$—C(=O)—(CH$_2$)C(CH$_3$)$_2$,

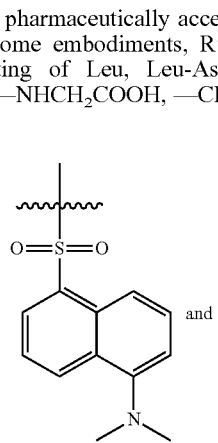

and

In some embodiments, $R^3$ is selected from —NH($R^{15}$), —N($R^{15}$)$_2$, and —S$R^{15}$;

In some embodiments, $R^3$ is —N(CH$_3$)$_2$.

In some embodiments, $R^3$ is —SCH$_3$.

In some embodiments, a pharmaceutical composition comprising the compound of Formula (I) and a pharmaceutically acceptable carrier are provided.

In some embodiments, a method for treating cancer is provided comprising administering an effective amount of the compound of Formula (I) to a subject in need thereof.

In some embodiments, the subject is mammalian.

In some embodiments, the subject is human.

In some embodiments, the cancer is selected from the group consisting of prostate cancer, and Ewing's sarcoma.

In some embodiments, a method of killing or inhibiting the growth of a neoplastic cell is provided, comprising contacting the cell with an effective amount of the compound of Formula (I).

In some embodiments, the cell is mammalian.

In some embodiments, the cell is human.

In some embodiments, the cell is in vitro.

In some embodiments, the cell is in vivo.

In some embodiments, a cancer comprises the cell, the cancer being selected from the group consisting of prostate cancer, breast cancer, pancreatic cancer, Ewing's sarcoma, and melanoma.

In some embodiments, the compound of Formula (I) has the formula:

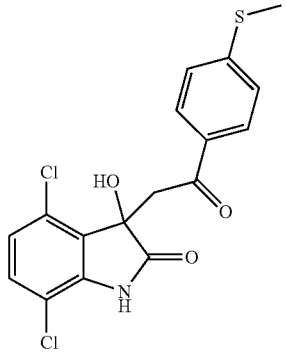

In some embodiments, the compound of Formula (I) has the formula:

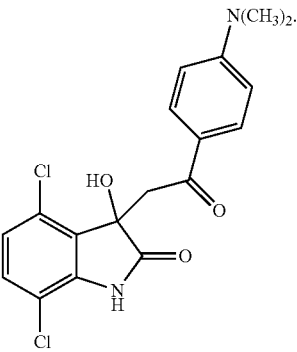 [SMILES: CN(C)c1ccc(C(=O)CC2(O)C(=O)Nc3c(Cl)ccc(Cl)c32)cc1]

In some embodiments, the compound of Formula (I) may be selected from the groups consisting of

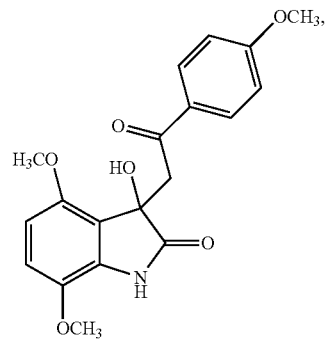

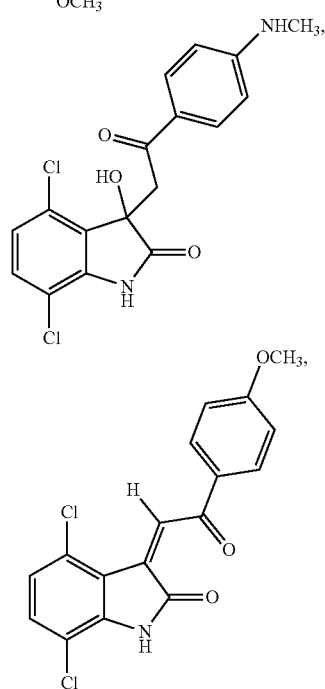

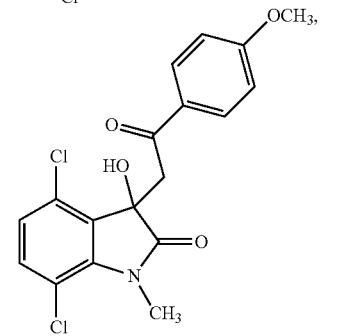

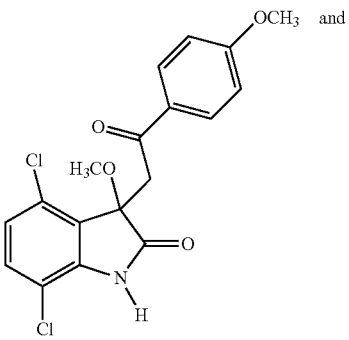

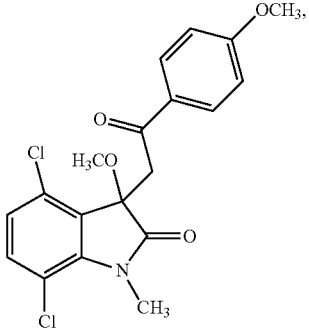 [SMILES: COc1ccc(C(=O)CC2(OC)C(=O)N(C)c3c(Cl)ccc(Cl)c32)cc1]

or a pharmaceutically acceptable salt thereof.

DETAILED DESCRIPTION

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Figure 1:
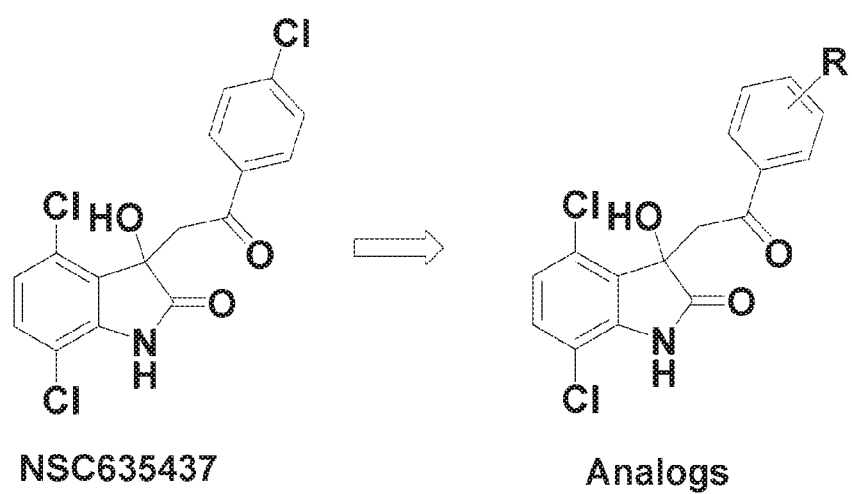
FIG. 1 shows the structure of NSC635453 and a generic structure for certain analogs.
Figure 2:
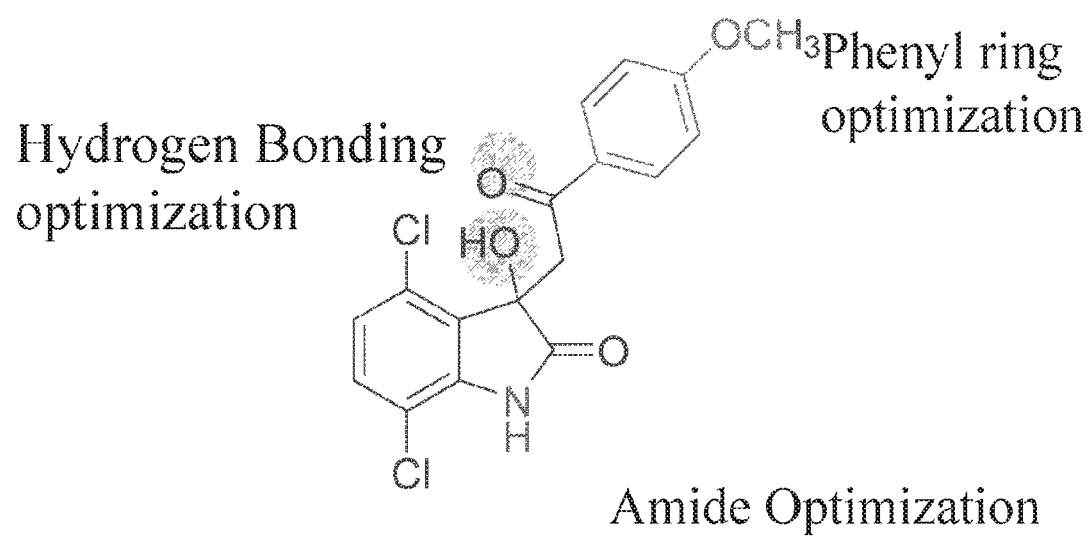
FIG. 2 shows an example strategy to increase the potency of YK-4-279.

A NCI/DTP library of three thousands small molecules was screened for EWS-FLI1 binding using Surface Plasmon Resonance. The compound, NSC635437, was selected as a suitable candidate for further optimization and further study (FIG. 1). Of the first series of analogs designed, YK-4-279, was the most active (FIG. 2). YK-4-279 has been shown to functionally inhibit EWS-FLI1 and ESFT cells and leads to caspase-3 activity increase (Hyariye N Erkizan et al. A small molecule blocking oncogenic protein EWS-FI1 interactin with RHA helicase A inhibits growth of Ewing's sarcoma. Nature Medicine 15(7) 750-756 (2009)). The present application relates to improved compounds and methods of using such compounds to treat disorders such as Ewing's sarcoma.

Definitions

As used herein, any "R" group(s) such as, without limitation, R, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^a$, $R^b$, represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. For example, without limitation, if $R^{1a}$ and $R^{1b}$ of an $NR^{1a}R^{1b}$ group are indicated to be "taken together," it means that they are covalently bonded to one another to form a ring:

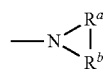

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino and a di-substituted amino group, and protected derivatives thereof.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

As used herein, "alkyl" refers to a straight or branched hydrocarbon chain that includes a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs.

A "(heteroalicyclyl)alkyl" and "(heterocyclyl)alkyl" refer to a heterocyclic or a heteroalicylylic group connected, as a substituent, via a lower alkylene group. The lower alkylene and heterocyclyl of a (heterocyclyl)alkyl may be substituted or unsubstituted. Examples include but are not limited tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl.

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl or a cycloalkynyl is defined as above. A non-limiting list of alkoxys is methoxy, ethoxy, n-propoxy, 1-methylethoxy (isopropoxy), n-butoxy, iso-butoxy, sec-butoxy and tert-butoxy. An alkoxy may be substituted or unsubstituted.

As used herein, "acyl" refers to a hydrogen, alkyl, alkenyl, alkynyl, or aryl connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy, and 2-fluoroisobutoxy. A haloalkoxy may be substituted or unsubstituted.

As used herein, "aryloxy" and "arylthio" refers to RO— and RS—, in which R is an aryl, such as but not limited to phenyl. Both an aryloxy and arylthio may be substituted or unsubstituted.

A "sulfenyl" or "thio" group refers to an "—SR" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. A sulfenyl may be substituted or unsubstituted.

The term "sulfenyl" or "thio" includes, but is not limited to an —SH group (also referred to as a "thiol" group) as well as an —$SR_A$ group (also referred to as a "thioether" when $R_A$ is not hydrogen).

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl, as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2$—" group wherein X is a halogen.

A "trihalomethanesulfonamido" group refers to an "$X_3CS(O)_2N(R_A)$—" group wherein X is a halogen and $R_A$ is hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl.

The term "amino" as used herein refers to a —$N(R)_2$ group, wherein R is independently selected from the group consisting of hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An amino may be substituted or unsubstituted. The term "amino" includes, but is not limited to a —$NH_2$ group (also referred to as an "ammonium" group), a —NHR group (also referred to as a "secondary amine" when R is not hydrogen), or a —$NR_2$ group (also referred to as a "tertiary amine" when R is not hydrogen).

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—$SO_2N(R_AR_B)$" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An S-sulfonamido may be substituted or unsubstituted.

An "N-sulfonamido" group refers to a "$RSO_2N(R_A)$—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-sulfonamido may be substituted or unsubstituted.

An "O-carbamyl" group refers to a "—OC(=O)N($R_AR_B$)" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An O-carbamyl may be substituted or unsubstituted.

An "N-carbamyl" group refers to an "ROC(=O)N($R_A$)—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-carbamyl may be substituted or unsubstituted.

An "O-thiocarbamyl" group refers to a "—OC(=S)—N($R_AR_B$)" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An O-thiocarbamyl may be substituted or unsubstituted.

An "N-thiocarbamyl" group refers to an "ROC(=S)N($R_A$)—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-thiocarbamyl may be substituted or unsubstituted.

A "C-amido" group refers to a "—C(=O)N($R_AR_B$)" group in which $R_A$ and $R_B$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. A C-amido may be substituted or unsubstituted.

An "N-amido" group refers to a "RC(=O)N($R_A$)—" group in which R and $R_A$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Certain Synthetic Methods

In some embodiments, appropriate acetophenone (4.0 equiv.) and catalytic amount of diethylamine (10 drops) were added to a solution of 4,7-dichloroisatin (1.0 equiv.) in methanol (5 mL). The mixture was stirred at room temperature until starting material (4,7-dichloroisatin) disappeared completely. The resulted solution was concentrated and applied to flash chromatography eluting with Hexane/Ethyl acetate to afford pure product in quantitative yield. Further purification was done by recrystallization with Hexane/Ethyl acetate. NMR spectra were recorded using a Varian-400 spectrometer for $^1$H (400 MHz), chemical shifts (δ) are given in ppm downfield from tetramethylsilane as internal standard, and coupling constants (J-values) are in hertz (Hz). Elemental analyses were performed by Atlantic Microlabs.

Certain compounds provided herein can be prepared according to the following synthesis schemes.

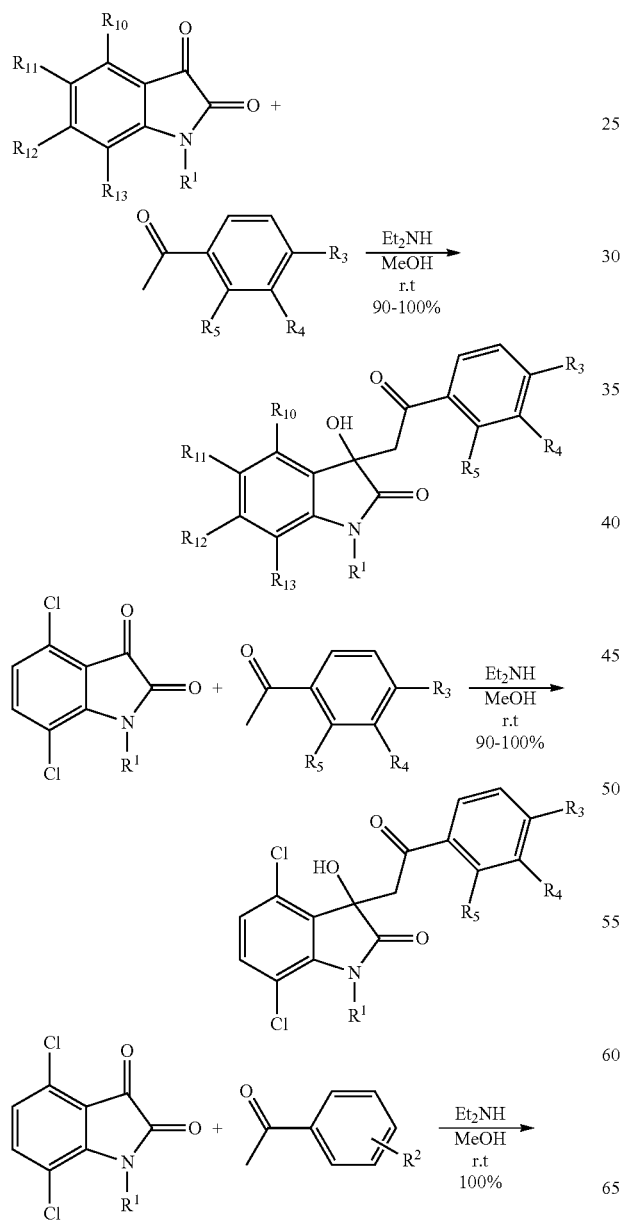

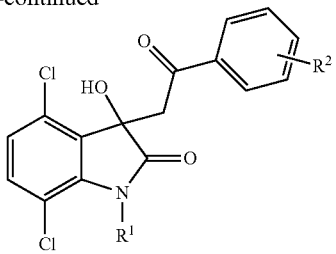

In these schemes, ketone (4.0 equiv.) and a catalytic amount of diethylamine (10 drops) are added to a solution of substituted isatin (1.0 equiv.) in methanol (5 mL). The mixture is stirred at room temperature until starting material (substituted isatin) disappears completely. The resulting solution is concentrated and applied to flash chromatography eluting with hexane/ethyl acetate to afford pure product in quantitative yield. Further purification is done by recrystallization with hexane/ethyl acetate.

The inhibitors incorporating a carbon-carbon double bond in the group linking the two ring systems can be prepared from the corresponding saturated inhibitor by reducing the compound using synthetic techniques known in the art.

Certain Compounds

Certain compounds provided herein include compounds having a formula:

Formula (I)

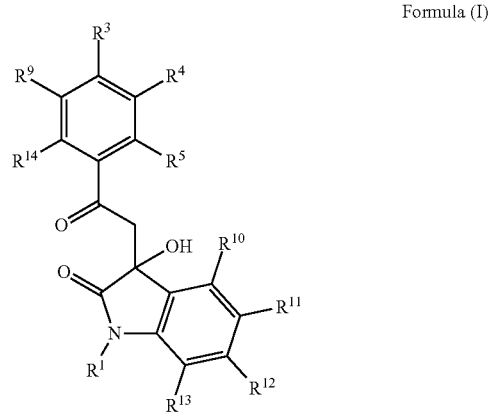

wherein $R^1$ is selected from the group consisting of hydrogen, one amino acid, two amino acids linked together, three amino acids linked together,

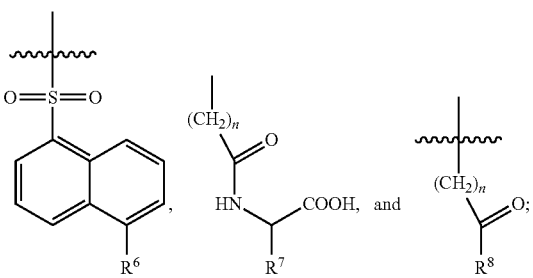

$R^3$, $R^4$, $R^5$, $R^9$, and $R^{14}$ are each independently selected from the group consisting of hydrogen, halogen, $C_{1-6}$ alkyl, $C_{1-6}$ alkoxy, —C(=O)NH$_2$, —NO$_2$, —NH$_2$, —OH, —NH($R^{15}$), —N($R^{15}$)$_2$, and —SR$^{15}$; $R^{10}$, $R^{11}$, $R^{12}$, and $R^{13}$ are each independently selected from the group consisting of hydrogen, halogen, $C_{1-6}$alkyl, $C_{1-6}$alkoxy, —C(=O)NH$_2$, —NO$_2$, —NH$_2$, —OH, —NH(R$^{15}$), —N(R$^{15}$)$_2$, and —SR$^{15}$; R$^6$ is $C_{1-6}$ dialkyl amine; R$^7$ is selected from the group consisting of hydrogen and $C_{1-6}$alkyl; R$^8$ and R$^{15}$ are each independently $C_{1-6}$alkyl; and n is an integer from 0 to 4; with the proviso that at least one of R$^3$, R$^4$, R$^5$, R$^9$, and R$^{14}$ is selected from the group consisting of —NH(R$^{15}$), —N(R$^{15}$)$_2$, and —SR$^{15}$.

In some embodiments, R$^1$ is selected from the group consisting of Leu, Leu-Asp, Leu-Asp-Ala, —CH$_2$—C(=O)—NHCH$_2$COOH, —CH$_2$—C(=O)—(CH$_2$)C(CH$_3$)$_2$,

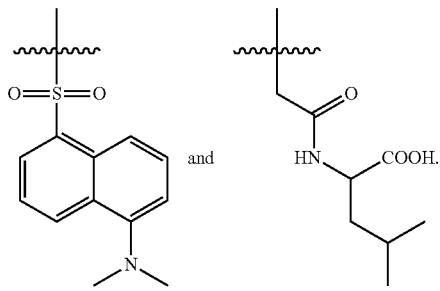 [SMILES: *S(=O)(=O)c1cccc2c(N(C)C)cccc12 ; *CC(=O)NC(CC(C)C)C(=O)O]

In some embodiments, R$^3$ is selected from —NH(R$^{15}$), —N(R$^{15}$)$_2$, and —SR$^{15}$;
In some embodiments, R$^3$ is —N(CH$_3$)$_2$.
In some embodiments, R$^3$ is —SCH$_3$.
In some embodiments, the compound of Formula (I) has the formula:

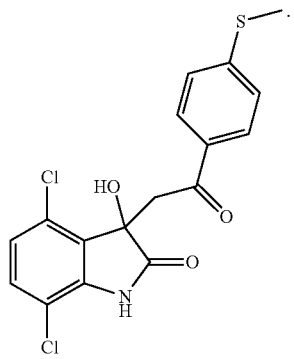 [SMILES: CSc1ccc(C(=O)CC2(O)C(=O)Nc3c(Cl)ccc(Cl)c32)cc1]

In some embodiments, the compound of Formula (I) has the formula:

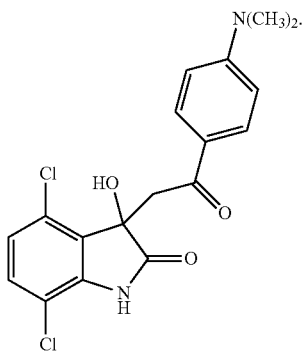 [SMILES: CN(C)c1ccc(C(=O)CC2(O)C(=O)Nc3c(Cl)ccc(Cl)c32)cc1]

Depending upon the substituents present, the small molecule inhibitors can be in a form of a pharmaceutically acceptable salt. The terms "pharmaceutically acceptable salt" as used herein are broad terms, and is to be given its ordinary and customary meaning to a person of ordinary skill in the art (and is not to be limited to a special or customized meaning), and refers without limitation to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as, for example, The Merck Index. Any suitable constituent can be selected to make a salt of the therapeutic agents discussed herein, provided that it is non-toxic and does not substantially interfere with the desired activity.

The compounds of preferred embodiments can include isomers, racemates, optical isomers, enantiomers, diastereomers, tautomers, and cis/trans conformers. All such isomeric forms are included within preferred embodiments, including mixtures thereof. As discussed above, the compounds of preferred embodiments may have chiral centers, for example, they may contain asymmetric carbon atoms and may thus exist in the form of enantiomers or diastereoisomers and mixtures thereof, e.g., racemates. Asymmetric carbon atom(s) can be present in the (R)-, (S)-, or (R,S)-configuration, preferably in the (R)- or (S)-configuration, or can be present as mixtures. Isomeric mixtures can be separated, as desired, according to conventional methods to obtain pure isomers.

The compounds can be in amorphous form, or in crystalline forms. The crystalline forms of the compounds of preferred embodiments can exist as polymorphs, which are included in preferred embodiments. In addition, some of the compounds of preferred embodiments may also form solvates with water or other organic solvents. Such solvates are similarly included within the scope of the preferred embodiments.

Certain Pharmaceutical Compositions

It is generally preferred to administer the inhibitors of preferred embodiments in an intravenous or subcutaneous unit dosage form; however, other routes of administration are also contemplated. Contemplated routes of administration include but are not limited to oral, parenteral, intravenous, and subcutaneous. The inhibitors of preferred embodiments can be formulated into liquid preparations for, e.g., oral administration. Suitable forms include suspensions, syrups, elixirs, and the like. Particularly preferred unit dosage forms for oral administration include tablets and capsules. Unit dosage forms configured for administration once a day are particularly preferred; however, in certain embodiments it can be desirable to configure the unit dosage form for administration twice a day, or more.

The pharmaceutical compositions of preferred embodiments are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Viscosity of the pharmaceutical compositions can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the thickening agent selected. An amount is preferably used that will achieve the selected viscosity. Viscous compositions are normally prepared from solutions by the addition of such thickening agents.

A pharmaceutically acceptable preservative can be employed to increase the shelf life of the pharmaceutical compositions. Benzyl alcohol can be suitable, although a variety of preservatives including, for example, parabens, thimerosal, chlorobutanol, or benzalkonium chloride can also be employed. A suitable concentration of the preservative is typically from about 0.02% to about 2% based on the total weight of the composition, although larger or smaller amounts can be desirable depending upon the agent selected. Reducing agents, as described above, can be advantageously used to maintain good shelf life of the formulation.

The inhibitors of preferred embodiments can be in admixture with a suitable carrier, diluent, or excipient such as sterile water, physiological saline, glucose, or the like, and can contain auxiliary substances such as wetting or emulsifying agents, pH buffering agents, gelling or viscosity enhancing additives, preservatives, flavoring agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; 18$^{th}$ and 19$^{th}$ editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

For oral administration, the pharmaceutical compositions can be provided as a tablet, aqueous or oil suspension, dispersible powder or granule, emulsion, hard or soft capsule, syrup or elixir. Compositions intended for oral use can be prepared according to any method known in the art for the manufacture of pharmaceutical compositions and can include one or more of the following agents: sweeteners, flavoring agents, coloring agents and preservatives. Aqueous suspensions can contain the active ingredient in admixture with excipients suitable for the manufacture of aqueous suspensions.

Formulations for oral use can also be provided as hard gelatin capsules, wherein the active ingredient(s) are mixed with an inert solid diluent, such as calcium carbonate, calcium phosphate, or kaolin, or as soft gelatin capsules. In soft capsules, the inhibitors can be dissolved or suspended in suitable liquids, such as water or an oil medium, such as peanut oil, olive oil, fatty oils, liquid paraffin, or liquid polyethylene glycols. Stabilizers and microspheres formulated for oral administration can also be used. Capsules can include push-fit capsules made of gelatin, as well as soft, sealed capsules made of gelatin and a plasticizer, such as glycerol or sorbitol. The push-fit capsules can contain the active ingredient in admixture with fillers such as lactose, binders such as starches, and/or lubricants such as talc or magnesium stearate and, optionally, stabilizers.

Tablets can be uncoated or coated by known methods to delay disintegration and absorption in the gastrointestinal tract and thereby provide a sustained action over a longer period of time. For example, a time delay material such as glyceryl monostearate can be used. When administered in solid form, such as tablet form, the solid form typically comprises from about 0.001 wt. % or less to about 50 wt. % or more of active ingredient(s), preferably from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %.

Tablets can contain the active ingredients in admixture with non-toxic pharmaceutically acceptable excipients including inert materials. For example, a tablet can be prepared by compression or molding, optionally, with one or more additional ingredients. Compressed tablets can be prepared by compressing in a suitable machine the active ingredients in a free-flowing form such as powder or granules, optionally mixed with a binder, lubricant, inert diluent, surface active or dispersing agent. Molded tablets can be made by molding, in a suitable machine, a mixture of the powdered inhibitor moistened with an inert liquid diluent.

Preferably, each tablet or capsule contains from about 1 mg or less to about 1,000 mg or more of an inhibitor of the preferred embodiments, more preferably from about 10, 20, 30, 40, 50, 60, 70, 80, 90, or 100 mg to about 150, 200, 250, 300, 350, 400, 450, 500, 550, 600, 650, 700, 750, 800, or 900 mg. Most preferably, tablets or capsules are provided in a range of dosages to permit divided dosages to be administered. A dosage appropriate to the patient and the number of doses to be administered daily can thus be conveniently selected. In certain embodiments it can be preferred to incorporate two or more of the therapeutic agents to be administered into a single tablet or other dosage form (e.g., in a combination therapy); however, in other embodiments it can be preferred to provide the therapeutic agents in separate dosage forms.

Suitable inert materials include diluents, such as carbohydrates, mannitol, lactose, anhydrous lactose, cellulose, sucrose, modified dextrans, starch, and the like, or inorganic salts such as calcium triphosphate, calcium phosphate, sodium phosphate, calcium carbonate, sodium carbonate, magnesium carbonate, and sodium chloride. Disintegrants or granulating agents can be included in the formulation, for example, starches such as corn starch, alginic acid, sodium starch glycolate, Amberlite, sodium carboxymethylcellulose, ultramylopectin, sodium alginate, gelatin, orange peel, acid carboxymethyl cellulose, natural sponge and bentonite, insoluble cationic exchange resins, powdered gums such as agar, karaya or tragacanth, or alginic acid or salts thereof.

Binders can be used to form a hard tablet. Binders include materials from natural products such as acacia, tragacanth, starch and gelatin, methyl cellulose, ethyl cellulose, carboxymethyl cellulose, polyvinyl pyrrolidone, hydroxypropylmethyl cellulose, and the like.

Lubricants, such as stearic acid or magnesium or calcium salts thereof, polytetrafluoroethylene, liquid paraffin, vegetable oils and waxes, sodium lauryl sulfate, magnesium lauryl sulfate, polyethylene glycol, starch, talc, pyrogenic silica, hydrated silicoaluminate, and the like, can be included in tablet formulations.

Surfactants can also be employed, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

Controlled release formulations can be employed wherein the amifostine or analog(s) thereof is incorporated into an inert matrix that permits release by either diffusion or leaching mechanisms. Slowly degenerating matrices can also be incorporated into the formulation. Other delivery systems can include timed release, delayed release, or sustained release delivery systems.

Coatings can be used, for example, nonenteric materials such as methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols, or enteric materials such as phthalic acid esters. Dyestuffs or pigments can be added for identification or to characterize different combinations of inhibitor doses When administered orally in liquid form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or *arachis* oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain sweetening and flavoring agents.

Pulmonary delivery can also be employed. The compound is delivered to the lungs while inhaling and traverses across the lung epithelial lining to the blood stream. A wide range of mechanical devices designed for pulmonary delivery of therapeutic products can be employed, including but not limited to nebulizers, metered dose inhalers, and powder inhalers, all of which are familiar to those skilled in the art. These devices employ formulations suitable for the dispensing of compound. Typically, each formulation is specific to the type of device employed and can involve the use of an appropriate propellant material, in addition to diluents, adjuvants, and/or carriers useful in therapy.

The compound and/or other optional active ingredients are advantageously prepared for pulmonary delivery in particulate form with an average particle size of from 0.1 µm or less to 10 µm or more, more preferably from about 0.2, 0.3, 0.4, 0.5, 0.6, 0.7, 0.8, or 0.9 µm to about 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5 µm. Pharmaceutically acceptable carriers for pulmonary delivery of inhibitor include carbohydrates such as trehalose, mannitol, xylitol, sucrose, lactose, and sorbitol. Other ingredients for use in formulations can include DPPC, DOPE, DSPC, and DOPC. Natural or synthetic surfactants can be used, including polyethylene glycol and dextrans, such as cyclodextran. Bile salts and other related enhancers, as well as cellulose and cellulose derivatives, and amino acids can also be used. Liposomes, microcapsules, microspheres, inclusion complexes, and other types of carriers can also be employed.

Pharmaceutical formulations suitable for use with a nebulizer, either jet or ultrasonic, typically comprise the inhibitor dissolved or suspended in water at a concentration of about 0.01 or less to 100 mg or more of inhibitor per mL of solution, preferably from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg per mL of solution. The formulation can also include a buffer and a simple sugar (e.g., for protein stabilization and regulation of osmotic pressure). The nebulizer formulation can also contain a surfactant, to reduce or prevent surface induced aggregation of the inhibitor caused by atomization of the solution in forming the aerosol.

Formulations for use with a metered-dose inhaler device generally comprise a finely divided powder containing the active ingredients suspended in a propellant with the aid of a surfactant. The propellant can include conventional propellants, such as chlorofluorocarbons, hydrochlorofluorocarbons, hydrofluorocarbons, and hydrocarbons. Preferred propellants include trichlorofluoromethane, dichlorodifluoromethane, dichlorotetrafluoroethanol, 1,1,1, 2-tetrafluoroethane, and combinations thereof. Suitable surfactants include sorbitan trioleate, soya lecithin, and oleic acid.

Formulations for dispensing from a powder inhaler device typically comprise a finely divided dry powder containing inhibitor, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, preferably from about 5, 10, 15, 20, 25, 30, 35, 40, 45, or 50 wt. % to about 55, 60, 65, 70, 75, 80, 85, or 90 wt. % of the formulation.

When a compound of the preferred embodiments is administered by intravenous, parenteral, or other injection, it is preferably in the form of a pyrogen-free, parenterally acceptable aqueous solution or oleaginous suspension. Suspensions can be formulated according to methods well known in the art using suitable dispersing or wetting agents and suspending agents. The preparation of acceptable aqueous solutions with suitable pH, isotonicity, stability, and the like, is within the skill in the art. A preferred pharmaceutical composition for injection preferably contains an isotonic vehicle such as 1,3-butanediol, water, isotonic sodium chloride solution, Ringer's solution, dextrose solution, dextrose and sodium chloride solution, lactated Ringer's solution, or other vehicles as are known in the art. In addition, sterile fixed oils can be employed conventionally as a solvent or suspending medium. For this purpose, any bland fixed oil can be employed including synthetic mono or diglycerides. In addition, fatty acids such as oleic acid can likewise be used in the formation of injectable preparations. The pharmaceutical compositions can also contain stabilizers, preservatives, buffers, antioxidants, or other additives known to those of skill in the art.

The duration of the injection can be adjusted depending upon various factors, and can comprise a single injection administered over the course of a few seconds or less, to 0.5, 0.1, 0.25, 0.5, 0.75, 1, 2, 3, 4, 5, 6, 7, 8, 9, 10, 11, 12, 13, 14, 15, 16, 17, 18, 19, 20, 21, 22, 23, or 24 hours or more of continuous intravenous administration.

The compounds of the preferred embodiments can additionally employ adjunct components conventionally found in pharmaceutical compositions in their art-established fashion and at their art-established levels. Thus, for example, the compositions can contain additional compatible pharmaceutically active materials for combination therapy (such as supplementary antimicrobials, antipruritics, astringents, local anesthetics, anti-inflammatory agents, reducing agents, chemotherapeutics and the like), or can contain materials useful in physically formulating various dosage forms of the preferred embodiments, such as excipients, dyes, thickening agents, stabilizers, preservatives or antioxidants. Anti-cancer agents that can be used in combination with the compounds of preferred embodiments include, but are not limited to, vinca alkaloids such as vinblastine and vincristine; anthracyclines such as doxorubicin, daunorubicin, epirubicin; anthracenes such as bisantrene and mitoxantrone; epipodophyllo-toxins such as etoposide and teniposide; and other anticancer drugs such as actinomyocin D, mithomycin C, mitramycin, methotrexate, docetaxel, etoposide (VP-16), paclitaxel, docetaxel, and adriamycin); and immunosuppressants (e.g., cyclosporine A, tacrolimus). In some embodiments, the compounds, compositions and methods provided herein may be in combination with histone deacetylase inhibitors (HDAC), aurora kinase inhibitors, demethylating agents (such as 5-AZA cytidine), immunotherapy with natural killer cells, IGF-IR antibodies, Ewing antigen antibodies, immunosuppressive drugs, and hydroxyurea. Examples of histone deacetylase inhibitors include vorinostat, romidepsin, panobinostat, valproic acid, belinostat, mocetinostat, givinostat, and trichostatin A. Examples of aurora kinase inhibitors include ZM447439, hesperadin, and VX-680. Examples of demethylating agents include 5-azacytidine, 5-azadeoxycytidine, and procaine. Examples of immunosuppressive drugs include 6-mercaptopurine, and azathioprine.

Certain Kits

The compounds of the preferred embodiments can be provided to an administering physician or other health care professional in the form of a kit. The kit is a package which houses a container which contains the compounds in a suitable pharmaceutical composition, and instructions for administering the pharmaceutical composition to a subject. The kit can optionally also contain one or more additional therapeutic agents, e.g., chemotherapeutics currently employed for treating the sarcomas described herein. For example, a kit containing one or more compositions comprising compounds of the preferred embodiments in combination with one or more additional chemotherapeutic agents can be provided, or separate pharmaceutical compositions containing an inhibitor of the preferred embodiments and additional therapeutic agents can be provided. The kit can also contain separate doses of a compound of the preferred embodiments for serial or sequential administration. The kit can optionally contain one or more diagnostic tools and instructions for use. The kit can contain suitable delivery devices, e.g., syringes, and the like, along with instructions for administering the inhibitor(s) and any other therapeutic agent. The kit can optionally contain instructions for storage, reconstitution (if applicable), and administration of any or all therapeutic agents included. The kits can include a plurality of containers reflecting the number of administrations to be given to a subject.

Certain Therapeutic Methods

Some embodiments provided herein relate to methods of treating the Ewing's sarcoma family of tumors (ESFT). ESFT contains the unique fusion protein EWS-FLI1. ESFT affects patients between the ages of 3 and 40 years, with most cases occurring in the second decade. Although the embryologic cell type from which ESFT are derived is unknown, the tumor often grows in close proximity to bone, but can occur as a soft-tissue mass. Over 40% of patients who present with localized tumors will develop recurrent disease and the majority of these will die from ESFT, while 75-80% of patients who present with metastatic ESFT will die within 5 years despite high-dose chemotherapy (Grier H E, Krailo M D, Tarbell N J, et al. Addition of ifosfamide and etoposide to standard chemotherapy for Ewing's sarcoma and primitive neuroectodermal tumor of bone. N Engl J Med 2003; 348(8):694-701). These survival rates have not improved for the past 20 years, even after dose-intensifying chemotherapy. To improve survival and reduce therapy-related morbidity, novel targeted strategies for treating ESFT patients, as provided in the preferred embodiments, can be employed.

ESFT are characterized by a translocation, occurring in 95% of tumors, between the central exons of the EWS gene (Ewing Sarcoma) located on chromosome 22 to the central exons of an ets family gene; either FLI1 (Friend Leukemia Insertion) located on chromosome 11, t(11;22), or ERG located on chromosome 21, t(21;22). The EWS-FLI1 fusion transcript encodes a 55 kDa protein (electrophoretic motility of approximately 68 kD) with two primary domains. The EWS domain is a potent transcriptional activator, while the FLI1 domain contains a highly conserved ets DNA binding domain (May W A, Lessnick S L, Braun B S, et al. The Ewing's sarcoma EWS/FLI-1 fusion gene encodes a more potent transcriptional activator and is a more powerful transforming gene than FLI-1. Mol Cell Biol 1993; 13(12): 7393-8); the resulting EWS-FLI1 fusion protein acts as an aberrant transcription factor. EWS-FLI1 transformation of mouse fibroblasts requires both the EWS and FLI1 functional domains to be intact (May W A, Gishizky M L, Lessnick S L, et al. Ewing sarcoma 11;22 translocation produces a chimeric transcription factor that requires the DNA-binding domain encoded by FLI1 for transformation. Proc Natl Acad Sci USA 1993; 90(12):5752-6).

EWS-FLI1 is an outstanding therapeutic target, in that it is expressed only in tumor cells and is required to maintain the growth of ESFT cell lines. Reduced expression levels of EWS-FLI1 using either antisense oligodeoxynucleotides (ODN) (Toretsky J A, Connell Y, Neckers L, Bhat N K. Inhibition of EWS-FLI-1 fusion protein with antisense oligodeoxynucleotides. J Neurooncol 1997; 31(1-2):9-16; Tanaka K, Iwakuma T, Harimaya K, Sato H, Iwamoto Y. EWS-Flil antisense oligodeoxynucleotide inhibits proliferation of human Ewing's sarcoma and primitive neuroectodermal tumor cells. J Clin Invest 1997; 99(2):239-47) or small interfering RNAs (siRNA) (Ouchida M, Ohno T, Fujimura Y, Rao V N, Reddy E S. Loss of tumorigenicity of Ewing's sarcoma cells expressing antisense RNA to EWS-fusion transcripts. Oncogene 1995; 11(6):1049-54; Maksimenko A, Malvy C, Lambert G, et al. Oligonucleotides targeted against a junction oncogene are made efficient by nanotechnologies. Pharm Res 2003; 20(10):1565-7; Kovar H, Aryee D N, Jug G, et al. EWS/FLI-1 antagonists induce growth inhibition of Ewing tumor cells in vitro. Cell Growth Differ 1996; 7(4):429-37) cause decreased proliferation of ESFT cell lines and regression of tumors in nude mice. Recent advances in nanotechnology have improved the delivery and controlled release of siRNA, yet neither antisense ODN nor siRNA reduction of EWS-FLI1 in humans is possible with current technologies (Maksimenko A, Malvy C, Lambert G, et al. Oligonucleotides targeted against a junction oncogene are made efficient by nanotechnologies. Pharm Res 2003; 20(10):1565-7; Lambert G, Bertrand J R, Fattal E, et al. EWS fli-1 antisense nanocapsules inhibits Ewing sarcoma-related tumor in mice. Biochem Biophys Res Commun 2000; 279(2):401-6). One interesting approach to EWS-FLI1 targeting used comparative expression between siRNA reduced EWS-FLI1 and a library of small molecules, which led to a current clinical trial with Ara-C(Stegmaier K, Wong J S, Ross K N, et al. Signature-based small molecule screening identifies cytosine arabinoside as an EWS/FLI modulator in Ewing sarcoma. PLoS medicine 2007; 4(4):e122). This method of identifying Ara-C also indicated doxorubicin and puromycin would reduce EWS-FLI1 levels. Doxorubicin is currently used as standard therapy for ESFT patients and yet, survival is far from acceptable (Grier H E, Krailo M D, Tarbell N J, et al. Addition of ifosfamide and etoposide to standard chemotherapy for Ewing's sarcoma and primitive neuroectodermal tumor of bone. N Engl J Med 2003; 348(8):694-701). The use of Ara-C in ESFT patients is currently being evaluated in a Phase II trial. While it is hoped that this represents a needed clinical breakthrough, it certainly demonstrates the importance of small molecule targeting of EWS-FLI1. The preferred embodiments provide small molecule protein-protein interaction inhibitors (SMPPII) that disrupt EWS-FLI1 from critical protein partners, thereby achieving tumor specificity and more precise targeting of EWS-FLI1.

There is sufficient evidence to conclude that EWS-FLI1 fusion protein functions differently than either untranslocated EWS or FLI1 (May W A, Gishizky M L, Lessnick S L, et al. Ewing sarcoma 11;22 translocation produces a chimeric transcription factor that requires the DNA-binding domain encoded by FLI1 for transformation. Proc Natl Acad Sci USA 1993; 90(12):5752-6). Changes in gene expression profiles of EWS-FLI1-expressing cell lines (Braun B S, Frieden R, Lessnick S L, May W A, Denny C T. Identification of target genes for the Ewing's sarcoma EWS/FLI fusion protein by representational difference analysis. Mol Cell Biol 1995; 15(8):4623-30) or tumor cells taken from ESFT patients, compared to tumors lacking EWS-FLI1 expression, indicate that EWS-FLI1 may play a role in transcriptional regulation (Khan J, Wei J S, Ringner M, et al. Classification and diagnostic prediction of cancers using gene expression profiling and artificial neural networks. Nat Med 2001; 7(6):673-9; Baer C, Nees M, Breit S, et al. Profiling and functional annotation of mRNA gene expression in pediatric rhabdomyosarcoma and Ewing's sarcoma. Int J Cancer 2004; 110(5):687-94). While a clear picture of the mechanism of EWS-FLI1-regulated gene expression has yet to emerge, this activity is likely the result of direct or secondary interactions between EWS-FLI1 and regulators of RNA synthesis and splicing (Uren A, Toretsky J A. Ewing's Sarcoma Oncoprotein EWS-FLI1: the Perfect Target without a Therapeutic Agent. Future Onc 2005; 1(4):521-8).

EWS-FLI1 is a great therapeutic target since it is only expressed in tumor cells; however, the ability to target this tumor-specific oncogene has previously not been successful. One of the challenges towards small molecule development is that EWS-FLI1 lacks any know enzymatic domains, and enzyme domains have been thought to be critical for targeted therapeutics. In addition, EWS-FLI1 is a disordered protein, indicating that it does not exhibit a rigid structure that can be used for structure based drug design (Uren A, Tcherkasskaya O, Toretsky J A. Recombinant EWS-FLI1 oncoprotein activates transcription. Biochemistry 2004; 43(42):13579-89). In fact, the disordered nature of EWS-FLI1 is critical for its transcriptional regulation (Ng K P, Potikyan G, Savene R O, Denny C T, Uversky V N, Lee K A. Multiple aromatic side chains within a disordered structure are critical for transcription and transforming activity of EWS family oncoproteins. Proc Natl Acad Sci USA 2007; 104(2):479-84). Disordered proteins are considered as more attractive targets for small molecule protein-protein interaction inhibitors specifically because of their biochemical disordered properties (Cheng Y, LeGall T, Oldfield C J, et al. Rational drug design via intrinsically disordered protein. Trends Biotechnol 2006; 24(10):435-42).

EWS-FLI1 binds RNA helicase A in vitro and in vivo. It is believed that protein-protein interactions of EWS-FLI1 may contribute to its oncogenic potential; therefore, novel proteins have been sought that directly interact with and functionally modulate EWS-FLI1. Recombinant EWS-FLI1 that is transcriptionally active (Uren A, Tcherkasskaya O, Toretsky J A. Recombinant EWS-FLI1 oncoprotein activates transcription. Biochemistry 2004; 43(42):13579-89) was used as a target for screening a commercial peptide phage display library. Twenty-eight novel peptides that differentially bind to EWS-FLI1 were identified from phage sequencing. A National Center for Biotechnology Information database search for human proteins homologous to these peptides identified a peptide that was homologous to aa 823-832 of the human RNA helicase A, (RHA, gene bank accession number A47363) (Toretsky J A, Erkizan V, Levenson A, et al. Oncoprotein EWS-FLI1 activity is enhanced by RNA helicase A. Cancer Res 2006; 66(11):5574-81).

RHA, a member of the highly conserved DEXD/H box helicase family of proteins, is an integral, multifunctional member of the human transcriptome (Zhang S, Grosse F. Multiple functions of nuclear DNA helicase II (RNA helicase A) in nucleic acid metabolism. Acta Biochim Biophys Sin (Shanghai) 2004; 36(3):177-83; von Hippel P H, Delagoutte E. A general model for nucleic acid helicases and their "coupling" within macromolecular machines. Cell 2001; 104(2):177-90). These proteins are involved in diverse functions in a variety of organisms, from archaea, eubacteria, lower and higher eukaryotes and a number of viruses, including the positive-sense RNA viruses of the Flavivirus family. RHA is a transcriptional coactivator for NF-κB, and has been shown to form complexes with Creb-binding protein (CBP) (Nakajima T, Uchida C, Anderson S F, et al. RNA helicase A mediates association of CBP with RNA polymerase II. Cell 1997; 90(6):1107-12), RNA Polymerase II (Nakajima T, Uchida C, Anderson S F, et al. RNA helicase A mediates association of CBP with RNA polymerase II. Cell 1997; 90(6):1107-12), the breast cancer tumor suppressor BRCA1 (Anderson S F, Schlegel B P, Nakajima T, Wolpin E S, Parvin J D. BRCA1 protein is linked to the RNA polymerase II holoenzyme complex via RNA helicase A. Nat Genet 1998; 19(3):254-6), and, most recently, EWS-FLI1 (Toretsky J A, Erkizan V, Levenson A, et al. Oncoprotein EWS-FLI1 activity is enhanced by RNA helicase A. Cancer Res 2006; 66(11):5574-81). EWS-FLI1 binds to a region of RHA that is unique and not known as a binding site for any of the other RHA binding partners (Toretsky J A, Erkizan V, Levenson A, et al. Oncoprotein EWS-FLI1 activity is enhanced by RNA helicase A. Cancer Res 2006; 66(11):5574-81). RHA expression enhanced EWS-FLI1 mediated anchorage-independent colony formation, while an inactivating mutation of RHA prevented colony formation (Toretsky J A, Erkizan V, Levenson A, et al. Oncoprotein EWS-FLI1 activity is enhanced by RNA helicase A. Cancer Res 2006; 66(11):5574-81). This structural and function interaction is the basis for the therapeutic agents of preferred embodiments.

Despite the importance of transcription in tumorigenesis, the role of helicases in this process has not been well-studied. RHA is an integral member of the human transcriptome with diverse functions (Zhang S, Grosse F. Multiple functions of nuclear DNA helicase II (RNA helicase A) in nucleic acid metabolism. Acta Biochim Biophys Sin (Shanghai) 2004; 36(3):177-83; von Hippel P H, Delagoutte E. A general model for nucleic acid helicases and their "coupling" within macromolecular machines. Cell 2001; 104(2): 177-90). Our recently published data show that RHA interacts with the multifunctional EWS-FLI1 oncoprotein (Toretsky J A, Erkizan V, Levenson A, et al. Oncoprotein EWS-FLI1 activity is enhanced by RNA helicase A. Cancer Res 2006; 66(11):5574-81). This interaction could account for the observed ability of EWS-FLI1 to function in both transcription initiation and post-transcriptional RNA modification. RNA helicases are also known to bind and act as a bridge for some of the same factors that have been identified as binding partners for EWS-FLI1, including the splicing factor U1C (Chen J Y, Stands L, Staley J P, Jackups R R, Jr., Latus L J, Chang T H. Specific alterations of U1-C protein or U1 small nuclear RNA can eliminate the requirement of Prp28p, an essential DEAD box splicing factor. Mol Cell 2001; 7(1):227-32; Knoop L L, Baker S J. The splicing factor U1C represses EWS/FLI-mediated transactivation. J Biol Chem 2000; 275(32):24865-71), Creb-binding protein (CBP) (Nakajima T, Uchida C, Anderson S F, et al. RNA helicase A mediates association of CBP with RNA polymerase II. Cell 1997; 90(6):1107-12) and RNA Polymerase II (Nakajima T, Uchida C, Anderson S F, et al. RNA helicase A mediates association of CBP with RNA polymerase II. Cell 1997; 90(6):1107-12). RHA may perform a similar function for EWS-FLI1 and RNA Pol II, acting in the recruitment of key processing proteins. RHA may also contribute to ESFT oncogenesis by maintaining EWS-FLI1 as part of a large transcriptional complex whose function relies on the ATPase activity of RHA as an energy source. Finally, helicases, like RHA, can stabilize mRNA species (Iost I, Dreyfus M. mRNAs can be stabilized by DEAD-box proteins. Nature 1994; 372(6502):193-6). The stabilization and metabolism of EWS-FLI1 transcribed mRNA by RHA may augment the oncogenic nature of EWS-FLI1.

While EWS-FLI1 is quite specific to ESFT cells, EWS and RHA are ubiquitously expressed. The region between EWS-FLI1 and RHA are targeted by molecular therapeutics that may have specificity; since EWS-FLI1 is expressed only in tumors and the interaction points with RHA may be unique. Therapeutic agents, namely, small molecule protein-protein interaction inhibitors, are provided herein to inhibit EWS-FLI1 function.

Most translocation-fusion protein sarcomas portend a poor prognosis, including ESFT. The chromosomal translocation t(11;22), leading to the unique and critical fusion protein EWS-FLI1, is a perfect cancer target. Many other sarcomas share similar translocation variants (Table 2. from Helman L J, Meltzer P. Mechanisms of sarcoma development. Nat Rev Cancer 2003; 3(9):685-94).

EWS-FLI1 translocations have been reported in solid pseudopapillaryneoplasms of the pancreas (Maitra A., et al., Detection of t(11;22)(q24;q12) translocation and EWS-FLI-1 fusion transcript in a case of solid pseudopapillary tumor of the pancreas. Pediatr Dev Pathol 2000; 3:603-605), however the role of EWS-FLI1 in all solid pseudopaillary neoplasms remains to be resolved (Katharina Tiemann et al., Solid pseudopapillary neoplasms of the pancreas are associated with FLI-1 expression, but not with EWS/FLI-1 translocation).

EWS or FLI1 homologues are partners in translocations that occur in a wide range of sarcomas and leukemias. EWS, or its homologue TLS or FUS, is involved in chromosomal translocations of clear cell sarcoma, myxoid liposarcoma, desmoplastic small round cell tumor, chondrosarcoma and acute myeloid leukemia. FLI1 belongs to the ets family of genes. The FLI1 homologue ERG is translocated in approximately 10% of Ewing's sarcomas and 20% of acute myeloid leukemias. This suggests that EWS-FLI1 can serve as model system that might impact upon a family of diseases (related by translocation partners) that affect a large number of patients (Uren A., Tcherkasskaya O. and Toretsky J. A. Recombinant EWS-FLI1 oncoprotein activates transcription. Biochemistry 43(42) 13579-89 (2004)).

ERG is also translocated in prostate cancer, where the TMPRSS2:ERG fusion suggests a distinct molecular subtype that may define risk for disease progression (F. Demichelis et al., TMPRSS2:ERG gene fusion associated with lethal cancer in a watchful waiting cohort. Oncogene (2007) 26, 4596-4599). Other diseases where translocations of EWS or FLI1 family members have been observed include congenital fibrosarcoma and cellular mesobalstic nephroma where the ets family member ETV6 is juxtaposed with NTRK3. Other translocation gene fusions include chronic myeloid leukemia that leads to expression of the BCR-ABL fusion protein, and synovial sarcoma where the SYT gene from chromosome 18 is juxtaposed with either SSX1 or SSX2 from the X chromosome (Aykut Uren and Jeffrey A. Toretsky, Pediatric malignancies provide unique cancer therapy targets. Curr Opin Pediatr 17:14-19 (2005)).

Therefore, the therapeutic agents of the preferred embodiments have potential for application in many other tumors. More broadly, some of the most difficult leukemias also have translocation-generated fusion proteins involving the mixed-lineage leukemia gene (MLL, 11 q23), and our work could serve as a paradigm for a very treatment-resistant group of cancers (Pui C H, Chessells J M, Camitta B, et al. Clinical heterogeneity in childhood acute lymphoblastic leukemia with 11q23 rearrangements. Leukemia 2003; 17(4):700-6.). Thus embodiments include cancers where translocations have occurred. Translocation fusion genes are listed in Table 1.

TABLE 1

| Translocation | Genes | Type of fusion gene |
|---|---|---|
| Ewing's sarcoma | | |
| t(11; 22)(q24; q12) | EWSR1-FLI1 | Transcription factor |
| t(21; 22)(q22; q12) | EWSR1-ERG | Transcription factor |
| t(7; 22)(p22; q12) | EWSR1-ETV1 | Transcription factor |
| t(17; 22)(q21; q12) | EWSR1-ETV4 | Transcription factor |
| t(2; 22)(q33; q12) | EWSR1-FEV | Transcription factor |
| Clear-cell sarcoma | | |
| t(12; 22)(q13; q12) | EWSR1-ATF1 | Transcription factor |
| Desmoplastic small round-cell tumor | | |
| t(11 ;22)(p13:q12) | EWSR1-WT1 | Transcription factor |
| Myxoid chondrosarcoma | | |
| t(9; 22)(q22-31; q11-12) | EWSR1-NR4A3 | Transcription factor |
| Myxoid liposarcoma | | |
| t(12; 16)(q13; p11) | FUS-DDIT3 | Transcription factor |
| t(12; 22)(q13; q12) | EWSR1-DDIT3 | Transcription factor |
| Alveolar rhabdomyosarcoma | | |
| t(2; 13)(q35; q14) | PAX3-FOXO1A | Transcription factor |
| t(1; 13)(p36; q14) | PAX7-FOXO1A | Transcription factor |

TABLE 1-continued

| Translocation | Genes | Type of fusion gene |
|---|---|---|
| Synovial sarcoma | | |
| t(X; 18)(p11; q11) | SYT-SSX | Transcription factor |
| Dermatofibrosarcoma protuberans | | |
| t(17; 22)(q22; q13) | COL1A1-PDGFB | Growth factor |
| Congenital fibrosarcoma | | |
| t(12; 15)(p13; q25) | ETV6-NTRK3 | Transcription-factor receptor |
| Inflammatory myofibroblastic tumor | | |
| 2p23 rearrangements | TMP3-ALK; TMP4-ALK | Growth-factor receptor |
| Alveolar soft-part sarcoma | | |
| t(X; 17)(p11.2; q25) | ASPL-TFE3 | Transcription factor |

Certain Indications

Certain compounds, compositions and methods provided herein can be used to treat a number of disorders such as a tumor comprising a translocation gene fusion, Ewing's sarcoma, clear cell sarcoma, myxoid liposarcoma, desmoplastic small round-cell tumor, myxoid chondrosarcoma, acute myeloid leukemia, congenital fibrosarcoma, prostate cancer, breast cancer, and pancreatic cancer.

EXAMPLES

The following examples, including experiments and results achieved, are provided for illustrative purposes only and are not to be construed as limiting the present invention. Where chemical structures depict atoms having an unfilled valency, it is to be understood that the valency is satisfied with one or more hydrogen atoms.

Example 1—Synthesis of 4,7 Dichloroisatin Analogs

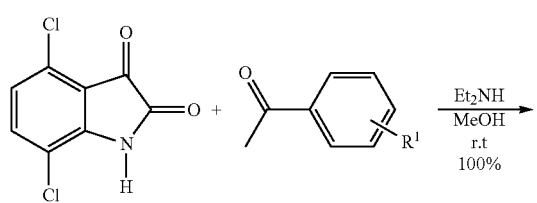

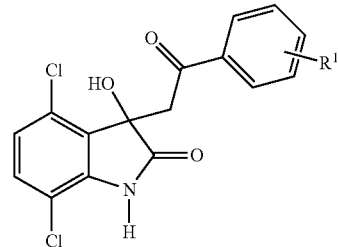

An appropriate acetophenone and 4,7-dichloroisatin were condensed in the presence of a catalytic amount of diethylamine to prepare the desired compound in quantitative yield. Example compounds: $R^1$=4'-CN (PT-1-11); 2'-$OCH_3$ (PT-1-12); 3'-$OCH_3$ (PT-1-18); 2',4'-$OCH_3$ (PT-1-19); 2',3'-$OCH_3$ (PT-1-20); 3',4'$OCH_3$ (PT-1-21); 3',5'$OCH_3$ (PT-1-22); 2',3',4',-$OCH_3$ (PT-1-23); 3',4',5'-$OCH_3$ (PT-1-13); 4'-$OC_2H_5$(PT-1-14); 4'-$CF_3$ (PT-1-15); 4'-$OCF_3$ (PT-1-16); 4'-$N(CH_3)_2$(PT-1-17); 4'-OPh (PT-1-60); 4'-$SCH_3$ (PT-1-67); and 4'-$C(CH_3)_2$ (PT-1-67).

Example 2—Synthesis of Dehydrated 4,7 Dichloroisatin Analogs

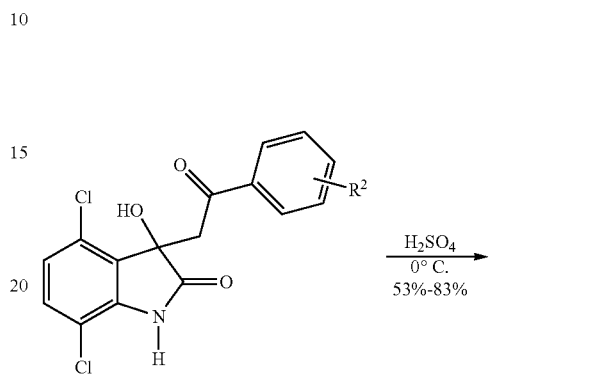

A solution of 4,7-dichloroisatin in 96% $H_2SO_4$ was stirred at room temperature to yield the reduced analogs. Example compounds: R2=4'-OCH3 (PT-1-33); 2',4'-OCH3 (PT-1-39); 2',3',4',-OCH3 (PT-1-41); 4'-OC2H5 (PT-1-43); and 4'-N(CH3)2 (PT-1-38).

Example 3—Synthesis of Reduced 4,7 Dichloroisatin Analogs

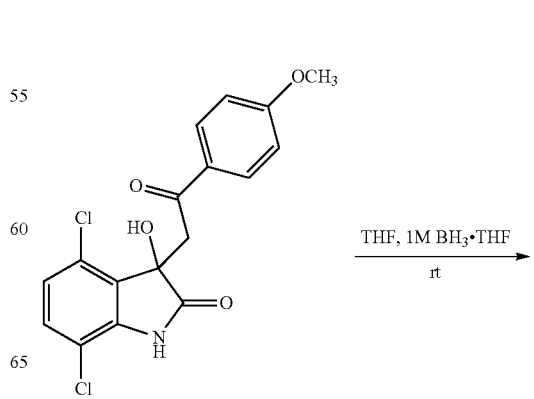

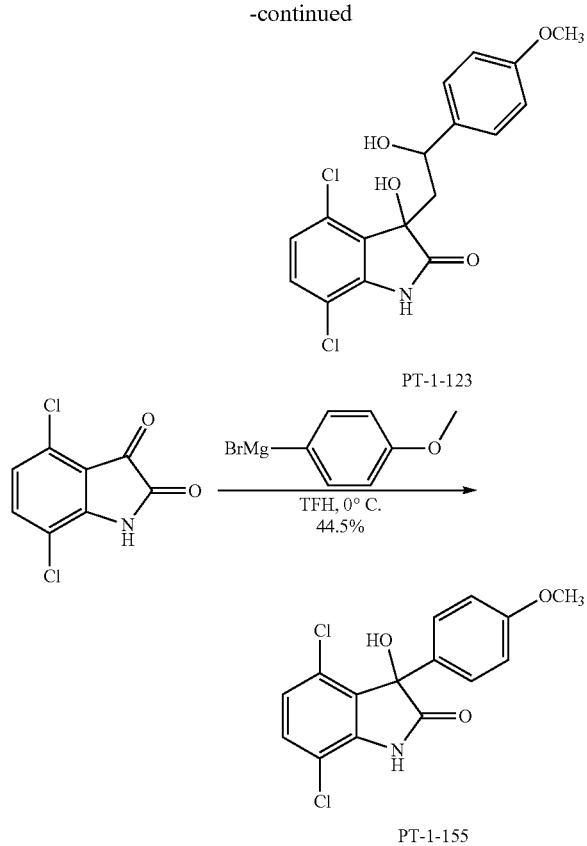

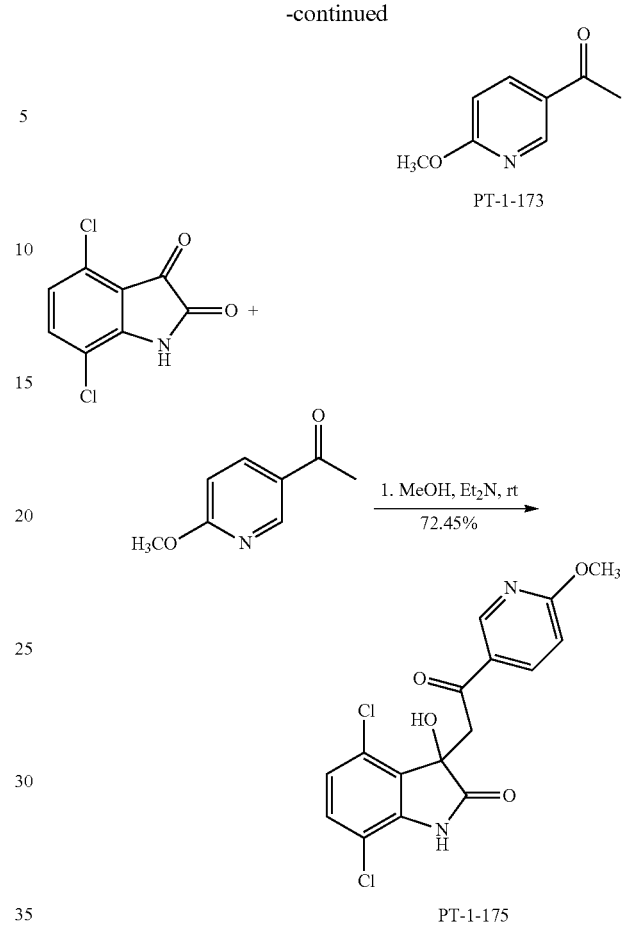

Example 4—Synthesis of Reduced 4.7 Dichloroisatin Pyiridine Derivatives

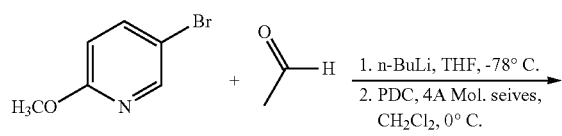

Example 5—Biological Activity of Certain Compounds

Compounds provided in Table 2 were prepared using methods similar to those described herein. The structures and $IC_{50}$ activities of particular compounds in PANC1 (a human pancreatic carcinoma), TC32 (human ESFT cell line), and TC71 (human ESFT cell line) cells are summarized in Table 2.

TABLE 2

| Example | Structure | $IC_{50}$ (µM) | | |
| --- | --- | --- | --- | --- |
| | | PANC 1 | TC32 | TC71 |
| YK-4-275 | 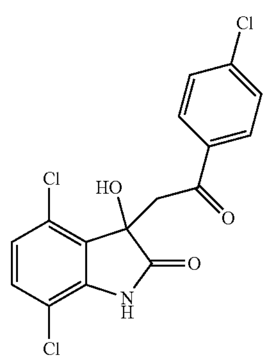 [SMILES: O=C(CC1(O)C(=O)Nc2c(Cl)ccc(Cl)c21)c1ccc(Cl)cc1] | 11 | 40 | 23.95 |

TABLE 2-continued

| Example | Structure | IC$_{50}$ (μM) | | |
|---|---|---|---|---|
| | | PANC 1 | TC32 | TC71 |
| YK-4-279 | 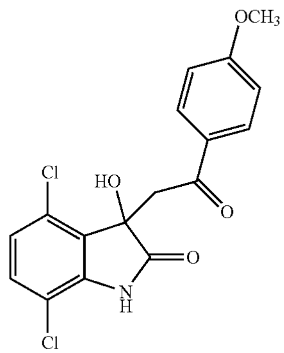 [SMILES: COc1ccc(C(=O)CC2(O)C(=O)Nc3c(Cl)ccc(Cl)c32)cc1] | 19.98; 33.96 | 0.9395; 0.7657 | 0.9178; 1.426 |
| YK-4-280 | 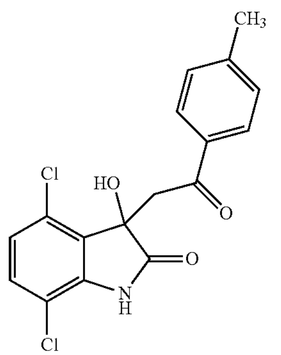 [SMILES: Cc1ccc(C(=O)CC2(O)C(=O)Nc3c(Cl)ccc(Cl)c32)cc1] | 40 | 12.11 | 30.08 |
| YK-4-281 | 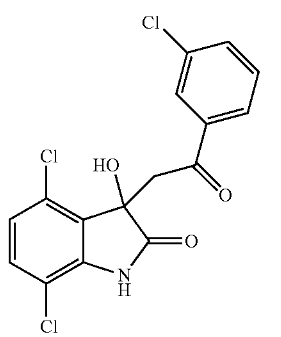 [SMILES: O=C(CC1(O)C(=O)Nc2c(Cl)ccc(Cl)c21)c1cccc(Cl)c1] | 40 | 7.218 | 29.61 |
| YK-4-283 | 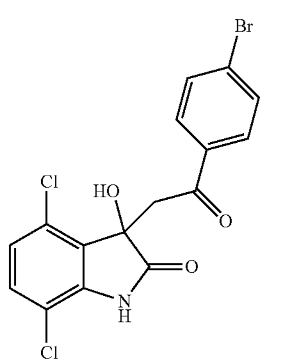 [SMILES: O=C(CC1(O)C(=O)Nc2c(Cl)ccc(Cl)c21)c1ccc(Br)cc1] | 12.66 | 8.911 | 25.96 |

TABLE 2-continued
| Example | Structure | IC$_{50}$ (μM) | | |
| --- | --- | --- | --- | --- |
| | | PANC 1 | TC32 | TC71 |
| YK-4-284 | 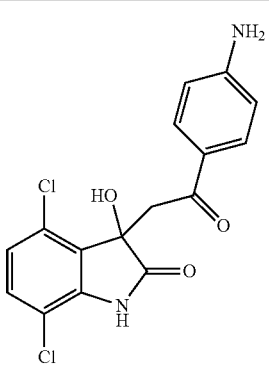 | 40 | 40 | 40 |
| YK-4-285 | 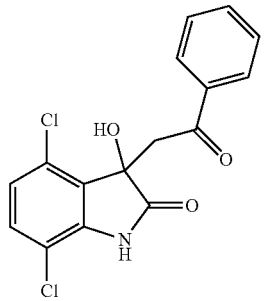 [SMILES: O=C(CC1(O)C(=O)Nc2c(Cl)ccc(Cl)c21)c1ccccc1] | 40 | 40 | 40 |
| YK-4-286 | 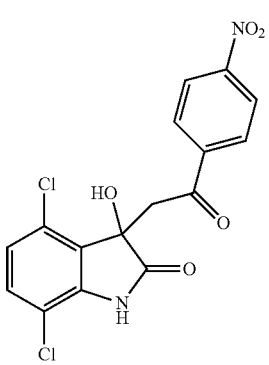 [SMILES: O=C(CC1(O)C(=O)Nc2c(Cl)ccc(Cl)c21)c1ccc([N+](=O)[O-])cc1] | 40 | 4.631 | 9.149 |
| YK-4-287 | 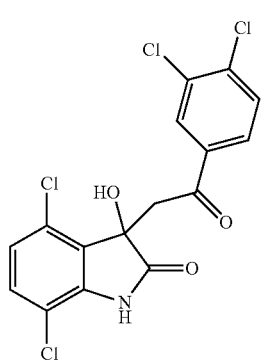 [SMILES: O=C(CC1(O)C(=O)Nc2c(Cl)ccc(Cl)c21)c1ccc(Cl)c(Cl)c1] | 12.6 | 6.32 | 15.82 |

TABLE 2-continued
| Example | Structure | IC₅₀ (μM) | | |
|---|---|---|---|---|
| | | PANC 1 | TC32 | TC71 |
| YK-4-288 | 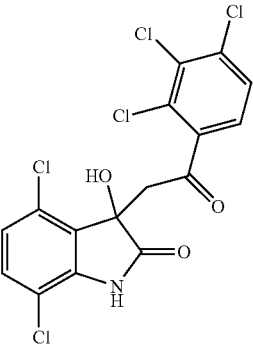 [SMILES: O=C(CC1(O)C(=O)Nc2c(Cl)ccc(Cl)c21)c1ccc(Cl)c(Cl)c1Cl] | 40 | 3.002 | 9.345 |
| YK-4-289 | 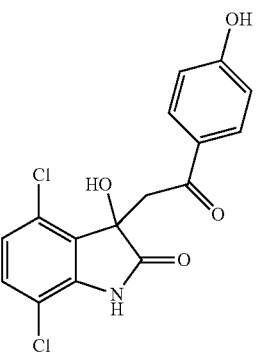 | 40 | 40 | 40 |
| PT-1-11 | 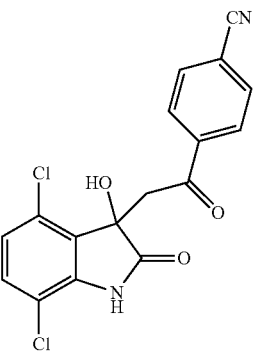 [SMILES: N#Cc1ccc(C(=O)CC2(O)C(=O)Nc3c(Cl)ccc(Cl)c32)cc1] | 40 | 10.34 | 12.28 |
| PT-1-14 | 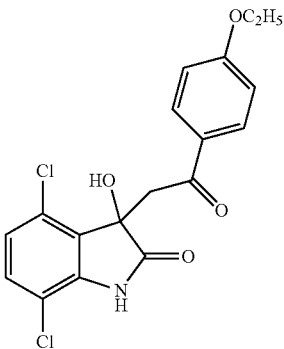 [SMILES: CCOc1ccc(C(=O)CC2(O)C(=O)Nc3c(Cl)ccc(Cl)c32)cc1] | 11.11 | 2.698 | 3.568 |

TABLE 2-continued

| Example | Structure | IC$_{50}$ (μM) | | |
|---|---|---|---|---|
| | | PANC 1 | TC32 | TC71 |
| PT-1-15 | (4-CF$_3$-phenyl ketone, 4,7-dichloro-3-hydroxy-oxindole) | 10.91 | 2.952 | 6.941 |
| PT-1-17 | (4-N(CH$_3$)$_2$-phenyl ketone, 4,7-dichloro-3-hydroxy-oxindole) | 40; 40 | 0.2589; 0.2836 | 0.4008; 0.2945 |
| PT-1-18 | (3-OCH$_3$-phenyl ketone, 4,7-dichloro-3-hydroxy-oxindole) | 40 | 40 | 40 |
| PT-1-19 | (2,4-di-OCH$_3$-phenyl ketone, 4,7-dichloro-3-hydroxy-oxindole) | 22.94 | 2.609 | 2.819 |

TABLE 2-continued

| Example | Structure | IC$_{50}$ (μM) | | |
|---|---|---|---|---|
| | | PANC 1 | TC32 | TC71 |
| PT-1-22 | 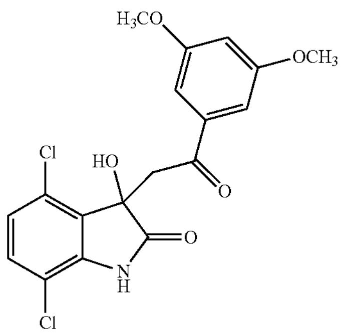 [SMILES: COc1cc(OC)cc(C(=O)CC2(O)C(=O)Nc3c(Cl)ccc(Cl)c32)c1] | 40 | 8.988 | 40 |
| PT-1-23 | 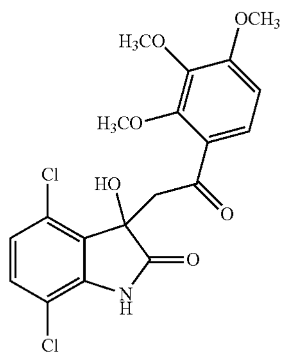 [SMILES: COc1ccc(C(=O)CC2(O)C(=O)Nc3c(Cl)ccc(Cl)c32)c(OC)c1OC] | 40 | 2.698 | 4.422 |
| PT-1-38 | 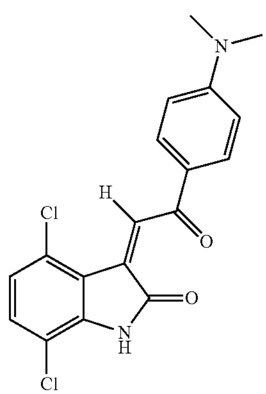 [SMILES: CN(C)c1ccc(C(=O)/C=C2\C(=O)Nc3c(Cl)ccc(Cl)c32)cc1] | 15.5; 40 | 0.2908; 0.3833 | 40; 0.5682 |
| PT-1-39 | 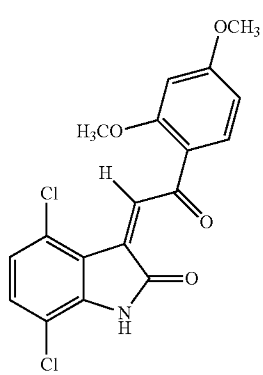 [SMILES: COc1ccc(C(=O)/C=C2\C(=O)Nc3c(Cl)ccc(Cl)c32)c(OC)c1] | 5.413; 6.763 | 1.052; 1.664 | 1.806; 2.318 |

TABLE 2-continued

| Example | Structure | IC$_{50}$ (μM) | | |
|---|---|---|---|---|
| | | PANC 1 | TC32 | TC71 |
| PT-1-41 | 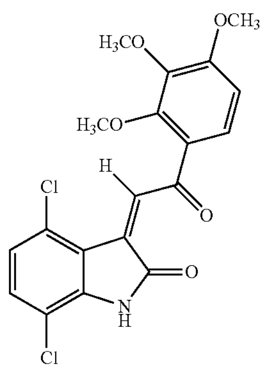 [SMILES: COc1ccc(C(=O)/C=C2\C(=O)Nc3c(Cl)ccc(Cl)c32)c(OC)c1OC] | 2.855; 5.158 | 1.194; 1.611 | 2.142; 1.599 |
| PT-1-43 | 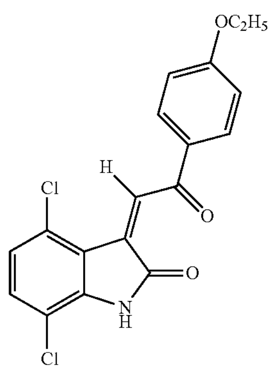 [SMILES: CCOc1ccc(C(=O)/C=C2\C(=O)Nc3c(Cl)ccc(Cl)c32)cc1] | 10.98 | 1.409 | 5.655 |
| PT-1-53 | 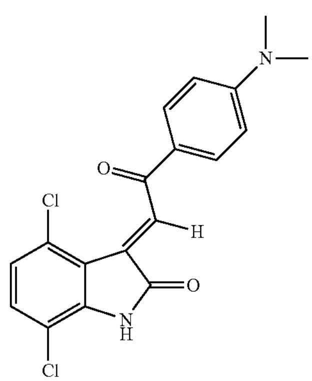 [SMILES: CN(C)c1ccc(C(=O)/C=C2/C(=O)Nc3c(Cl)ccc(Cl)c32)cc1] | 2.202 | 40 | 4.08 |
| PT-1-54 | 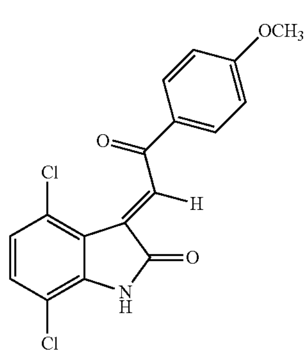 [SMILES: COc1ccc(C(=O)/C=C2/C(=O)Nc3c(Cl)ccc(Cl)c32)cc1] | 2.127; 40 | 1.498; 2.57 | 1.362; 2.202 |

TABLE 2-continued

| Example | Structure | IC$_{50}$ (µM) | | |
| --- | --- | --- | --- | --- |
| | | PANC 1 | TC32 | TC71 |
| PT-1-60 | 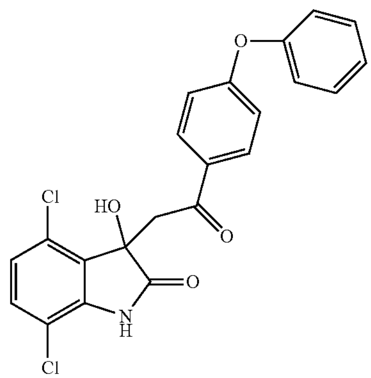 [SMILES: O=C(CC1(O)C(=O)Nc2c(Cl)ccc(Cl)c21)c1ccc(Oc2ccccc2)cc1] | 40 | 40 | 40 |
| PT-1-64 | | 40 | 32.8 | 40 |
| PT-1-67 | 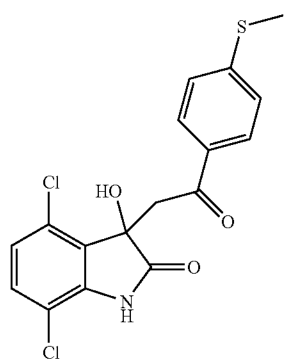 [SMILES: CSc1ccc(C(=O)CC2(O)C(=O)Nc3c(Cl)ccc(Cl)c32)cc1] | 28.1; 40 | 0.9822; 1.203 | 0.9086; 1.409 |
| PT-1-69 | 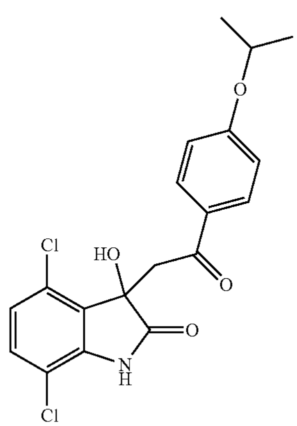 [SMILES: CC(C)Oc1ccc(C(=O)CC2(O)C(=O)Nc3c(Cl)ccc(Cl)c32)cc1] | 40 | 40 | 40 |
| PT-1-267 | 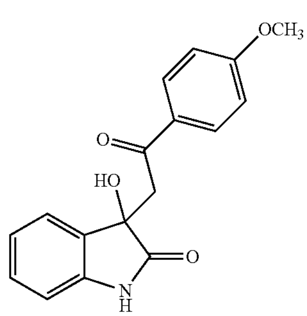 [SMILES: COc1ccc(C(=O)CC2(O)C(=O)Nc3ccccc32)cc1] | 40 | 40 | 40 |

TABLE 2-continued

| Example | Structure | IC$_{50}$ (μM) | | |
|---|---|---|---|---|
| | | PANC 1 | TC32 | TC71 |
| PT-1-271 | 4,6-dibromo-3-hydroxy-3-(2-(4-methoxyphenyl)-2-oxoethyl)indolin-2-one | 40 | 40 | 40 |
| PT-1-275 | 4-chloro-3-hydroxy-3-(2-(4-methoxyphenyl)-2-oxoethyl)indolin-2-one | 40 | 40 | 40 |
| PT-2-39 | 5,6-dichloro-3-hydroxy-3-(2-(4-methoxyphenyl)-2-oxoethyl)indolin-2-one | 40 | 40 | 40 |
| PT-2-52 | 7-chloro-3-hydroxy-3-(2-(4-methoxyphenyl)-2-oxoethyl)indolin-2-one | 40 | 40 | 40 |

TABLE 2-continued

| Example | Structure | IC$_{50}$ (μM) | | |
|---|---|---|---|---|
| | | PANC 1 | TC32 | TC71 |
| PT-2-56 | 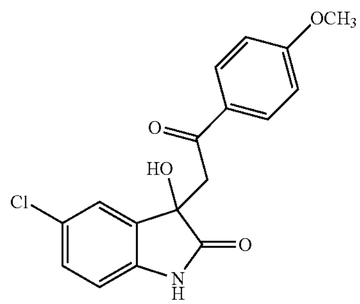 [SMILES: COc1ccc(C(=O)CC2(O)C(=O)Nc3ccc(Cl)cc32)cc1] | 40 | 12.36 | 40 |
| PT-2-59 | 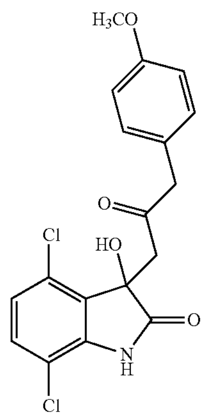 [SMILES: COc1ccc(CC(=O)CC2(O)C(=O)Nc3c(Cl)ccc(Cl)c32)cc1] | 40 | 40 | 40 |
| PT-2-64 | 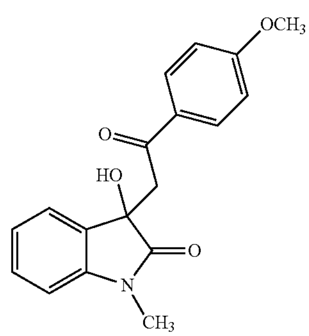 [SMILES: COc1ccc(C(=O)CC2(O)C(=O)N(C)c3ccccc32)cc1] | 40 | 40 | 40 |
| PT-2-69 | 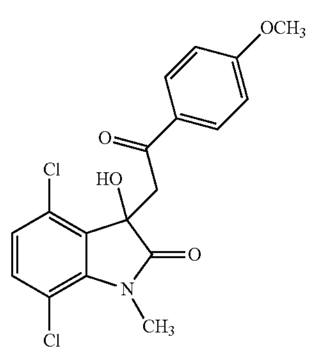 [SMILES: COc1ccc(C(=O)CC2(O)C(=O)N(C)c3c(Cl)ccc(Cl)c32)cc1] | 40; 40 | 2.178; 2.305 | 0.7145; 2.341 |

TABLE 2-continued

| Example | Structure | IC$_{50}$ (µM) | | |
|---|---|---|---|---|
| | | PANC 1 | TC32 | TC71 |
| PT-2-71 | 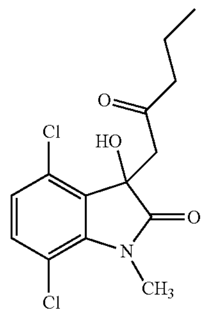 [SMILES: CCCC(=O)CC1(O)C(=O)N(C)c2c(Cl)ccc(Cl)c21] | 40 | 40 | 40 |
| YK-4-276 | 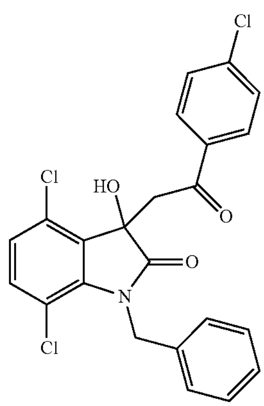 [SMILES: O=C(CC1(O)C(=O)N(Cc2ccccc2)c2c(Cl)ccc(Cl)c21)c1ccc(Cl)cc1] | 40 | 40 | 40 |
| YK-4-277 | 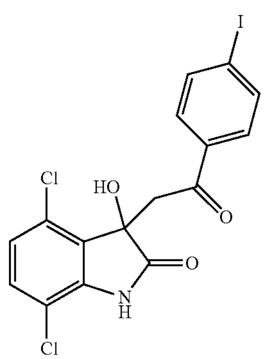 [SMILES: O=C(CC1(O)C(=O)Nc2c(Cl)ccc(Cl)c21)c1ccc(I)cc1] | 40 | 40 | 40 |
| YK-4-278 | 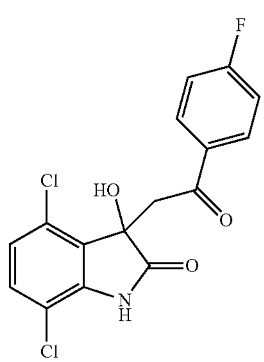 [SMILES: O=C(CC1(O)C(=O)Nc2c(Cl)ccc(Cl)c21)c1ccc(F)cc1] | 40 | 40 | 40 |

TABLE 2-continued

| Example | Structure | IC$_{50}$ (µM) | | |
|---|---|---|---|---|
| | | PANC 1 | TC32 | TC71 |
| YK-4-282 | *(structure: 4,7-dichloro-3-hydroxy-3-[2-(2-chlorophenyl)-2-oxoethyl]indolin-2-one)* | 40 | 40 | 40 |
| PT-1-12 | *(structure: 4,7-dichloro-3-hydroxy-3-[2-(2-methoxyphenyl)-2-oxoethyl]indolin-2-one)* | 40 | 40 | 40 |
| PT-1-13 | *(structure: 4,7-dichloro-3-hydroxy-3-[2-(3,4,5-trimethoxyphenyl)-2-oxoethyl]indolin-2-one)* | 40 | 40 | 40 |
| PT-1-16 | *(structure: 4,7-dichloro-3-hydroxy-3-[2-(4-trifluoromethoxyphenyl)-2-oxoethyl]indolin-2-one)* | 40 | 40 | 40 |

TABLE 2-continued

| Example | Structure | IC$_{50}$ (μM) | | |
|---|---|---|---|---|
| | | PANC 1 | TC32 | TC71 |
| PT-1-20 | 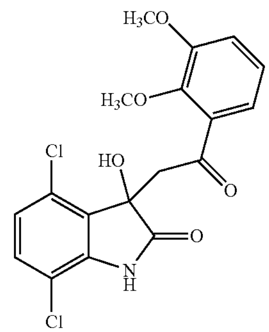 [SMILES: COc1cccc(C(=O)CC2(O)C(=O)Nc3c(Cl)ccc(Cl)c32)c1OC] | 40 | 40 | 40 |
| PT-1-21 | 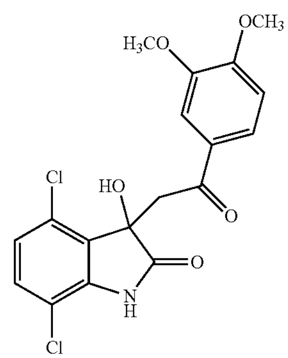 [SMILES: COc1ccc(C(=O)CC2(O)C(=O)Nc3c(Cl)ccc(Cl)c32)cc1OC] | 40 | 40 | 40 |
| PT-1-33 | 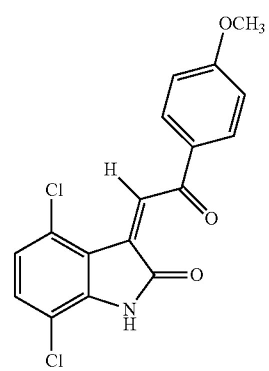 [SMILES: COc1ccc(C(=O)/C=C2\C(=O)Nc3c(Cl)ccc(Cl)c32)cc1] | 40 | 1.035 | 1.636 |
| PT-2-37 | 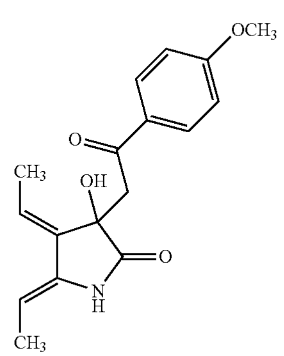 [SMILES: C/C=C1\NC(=O)C(O)(CC(=O)c2ccc(OC)cc2)\C1=C/C] | 40 | 40 | 40 |

TABLE 2-continued

| Example | Structure | IC$_{50}$ (μM) | | |
|---|---|---|---|---|
| | | PANC 1 | TC32 | TC71 |
| PT-2-78 | 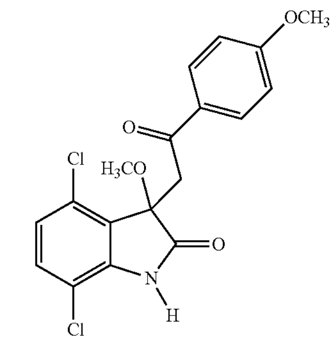 [SMILES: COc1ccc(C(=O)CC2(OC)C(=O)Nc3c(Cl)ccc(Cl)c32)cc1] | 40 | 40 | 40 |
| PT-2-79 | 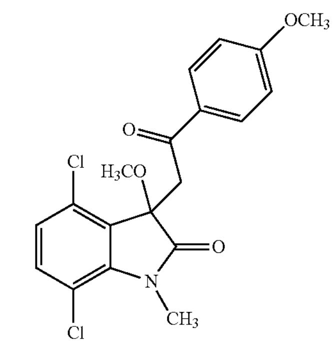 [SMILES: COc1ccc(C(=O)CC2(OC)C(=O)N(C)c3c(Cl)ccc(Cl)c32)cc1] | 11.19 | 12.13 | 16.98 |
| PT-2-47 | 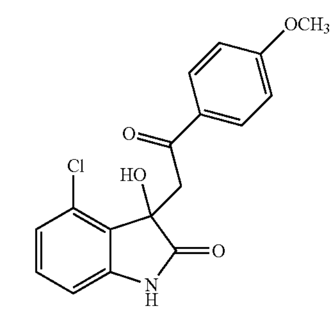 [SMILES: COc1ccc(C(=O)CC2(O)C(=O)Nc3cccc(Cl)c32)cc1] | | | |
| PT-2-39 | 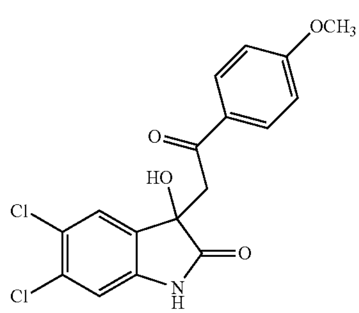 [SMILES: COc1ccc(C(=O)CC2(O)C(=O)Nc3cc(Cl)c(Cl)cc32)cc1] | | | |

TABLE 2-continued

| Example | Structure | IC$_{50}$ (μM) | | |
|---|---|---|---|---|
| | | PANC 1 | TC32 | TC71 |
| PT-2-99 | 3-hydroxy-4,7-dimethoxy-3-[2-(4-methoxyphenyl)-2-oxoethyl]-1,3-dihydro-2H-indol-2-one | | | |
| PT-2-94 | 4,7-difluoro-3-hydroxy-3-[2-(4-methoxyphenyl)-2-oxoethyl]-1,3-dihydro-2H-indol-2-one | | | |
| PT-2-84 | 4,7-dichloro-3-hydroxy-3-{2-[4-(methylamino)phenyl]-2-oxoethyl}-1,3-dihydro-2H-indol-2-one | | | |
| PT-2-89 | 4,7-dichloro-3-hydroxy-3-{2-[4-(morpholin-4-yl)phenyl]-2-oxoethyl}-1,3-dihydro-2H-indol-2-one | | | |

Example 6—Growth Inhibition of EWS-FLI1 Cells with Substituted Analogs

Figure 3A:
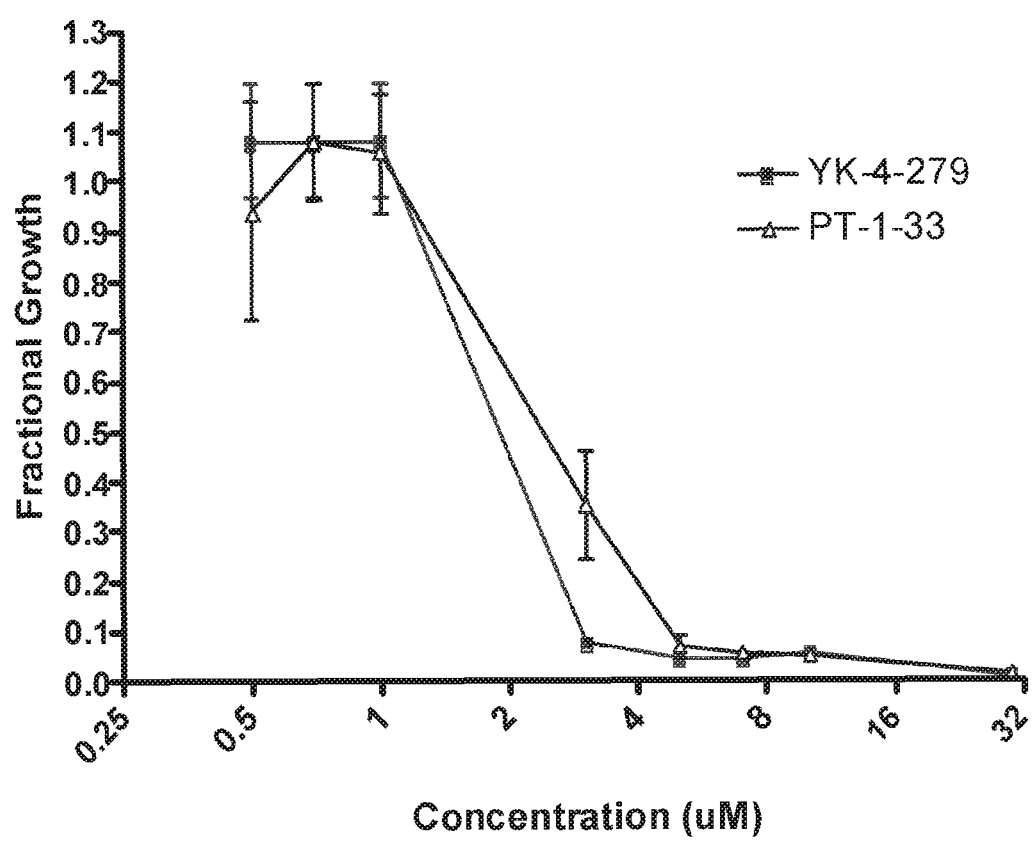
FIG. 3A is a graph of the growth inhibition of TC71 and TC32 cells for various concentrations of YK-4-279 and PT-1-33.
Figure 3B:
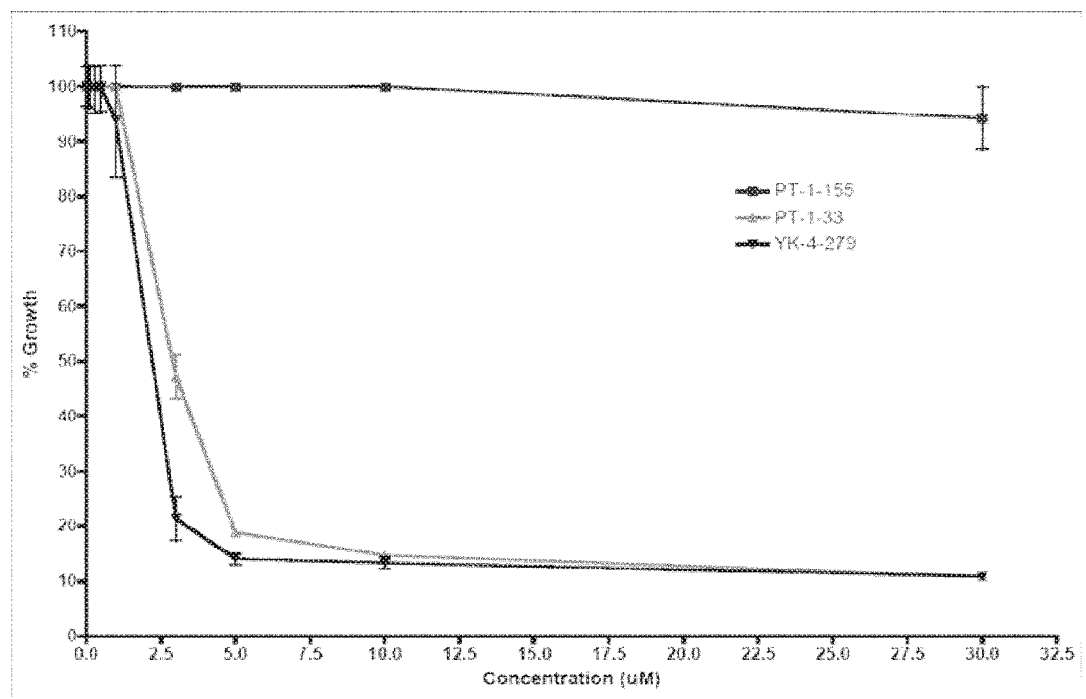
FIG. 3B is a graph of the growth inhibition of TC71 cells for various concentrations of YK-4-279, PT-1-33, and PT-1-55.
Figure 3C:
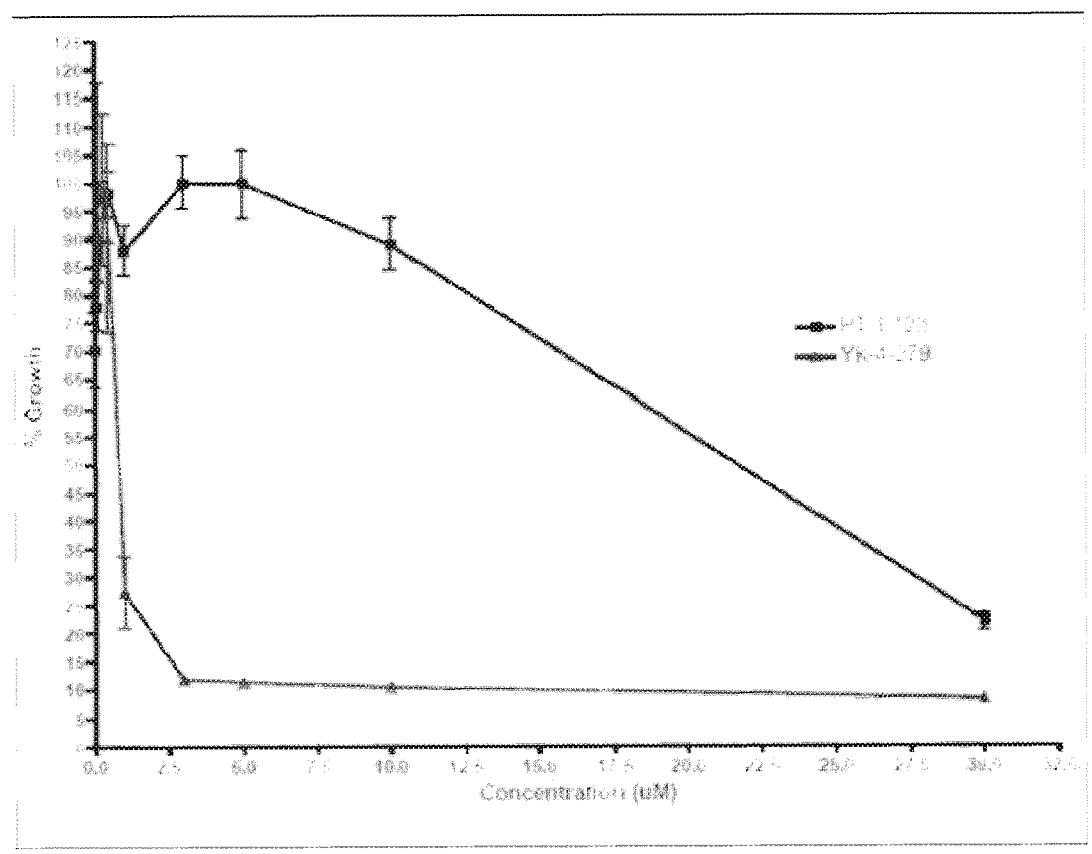
FIG. 3C is a graph of the growth inhibition of TC71 cells for various concentrations of YK-4-279 and PT-1-123.

The effects of the YK-4-279 analogs on the ESFT cells were tested by determining their growth inhibition. The IC50 of the lead compound was 900 nM for cells growing in monolayer. Growth inhibition of ESFT cells was measured for various concentrations of particular compounds. Growth inhibition of TC71 and TC32 cells was measured for various concentrations of YK-4-279 and PT-1-33 (FIG. 3A). Growth inhibition of TC71 cells was measured for various concentrations of YK-4-279, PT-1-33, and PT-1-55 (FIG. 3B). Growth inhibition of TC71 cells was measured for various concentrations of YK-4-279 and PT-1-123 (FIG. 3C). Some of the analogs had similar activity to YK-4-279. The dehydrated analogs and the alcohol analogs showed a similar activity against ESFT cells (FIG. 3A). Modifications of the ketone did not improve the activity of compounds (FIG. 3B and FIG. 3C).

Example 7—Apoptosis of EWS-FLI1 Cells

Figure 4:
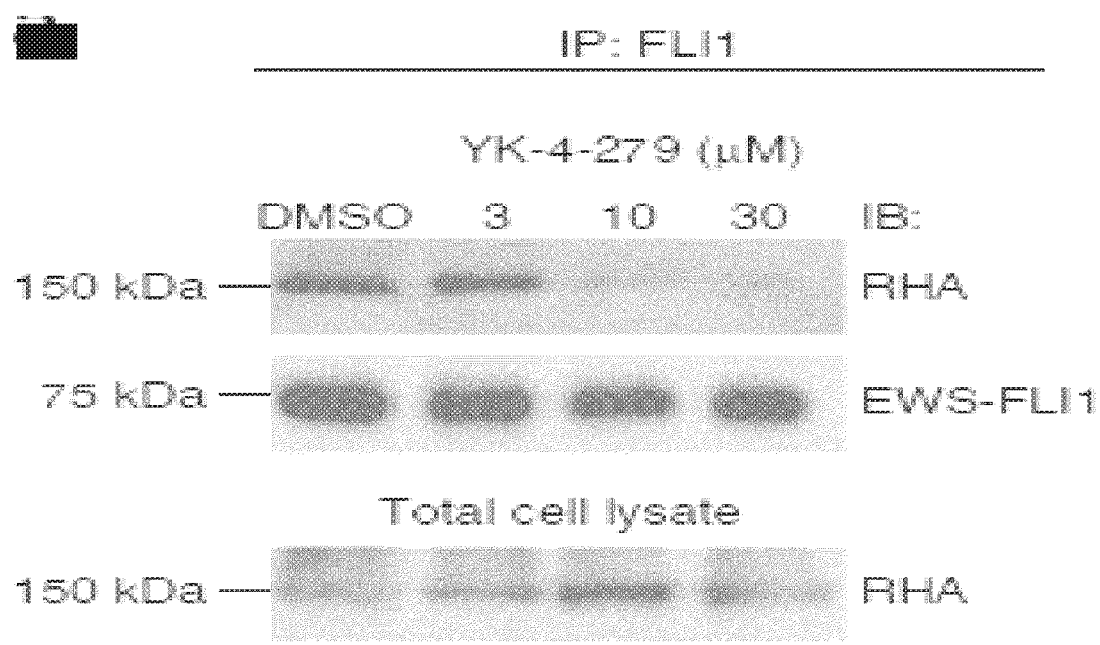
FIG. 4 is a photomicrograph of an immunoblot of protein lysates from TC32 cells treated with YK-4-279 and co-precipitated with RHA, EWS-FLI1 or total protein.

Immunoblots were prepared from protein lysates from TC32 cells treated with YK-4-279 and co-precipitated with RHA, EWS-FLI1 or total protein (FIG. 4). YK-4-279 did not directly affect the level of EWS-FLI1 or RHA but did disrupt their interactions. The disruption of the interaction of RHA with EWS-FLI1 presents an avenue for the development of a class of small molecules as potential therapeutics against the Ewing's family sarcoma tumors. While YK-4-279 disrupted the protein-protein interaction, PT-1-17 appeared to be more potent in the TC71 cells. Dehydrated analogs of YK-4-279 did not significantly increase the potency of the compounds.

Example 8—Disruption of EWS-FLI1/RHA Binding

The activity of candidate small molecules to disrupt binding between EWS-FLI1 and the His-tagged RHA protein, His-Tag RHA (647-1075), was screened in an ELISA assay. Briefly, candidate agents were incubated with RHA on plates coated with EWS-FLI1. After washing the plates, the amount of RHA that remained bound to the plates was determined using a primary anti-RHA antibody, and a secondary signal antibody.

Figure 5A:
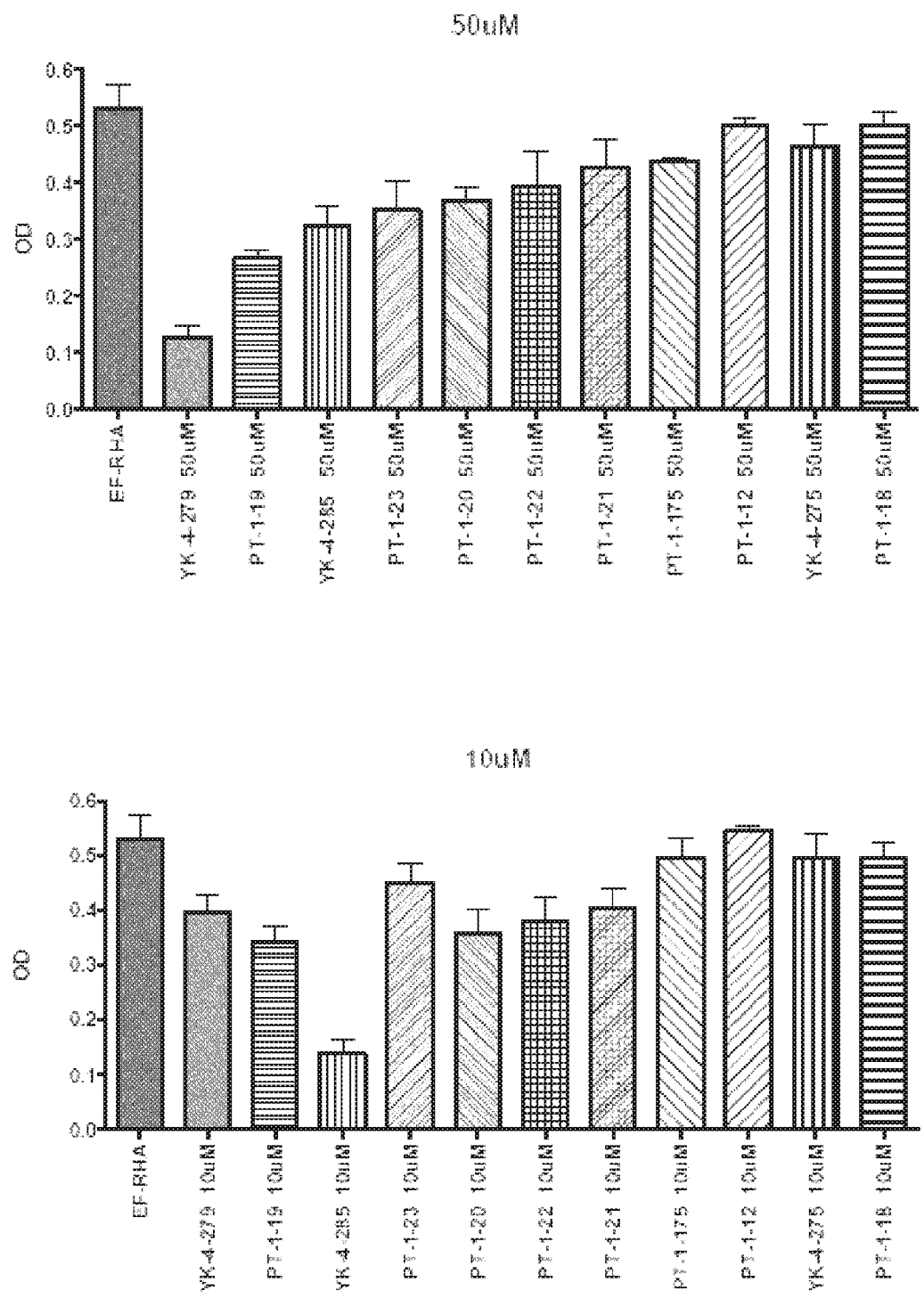
FIGS. 5A-5G are graphs of the relative optical density in ELISA assays measuring inhibition of EWS-FLI1 binding to RHA by various candidate agents.
Figure 5B:
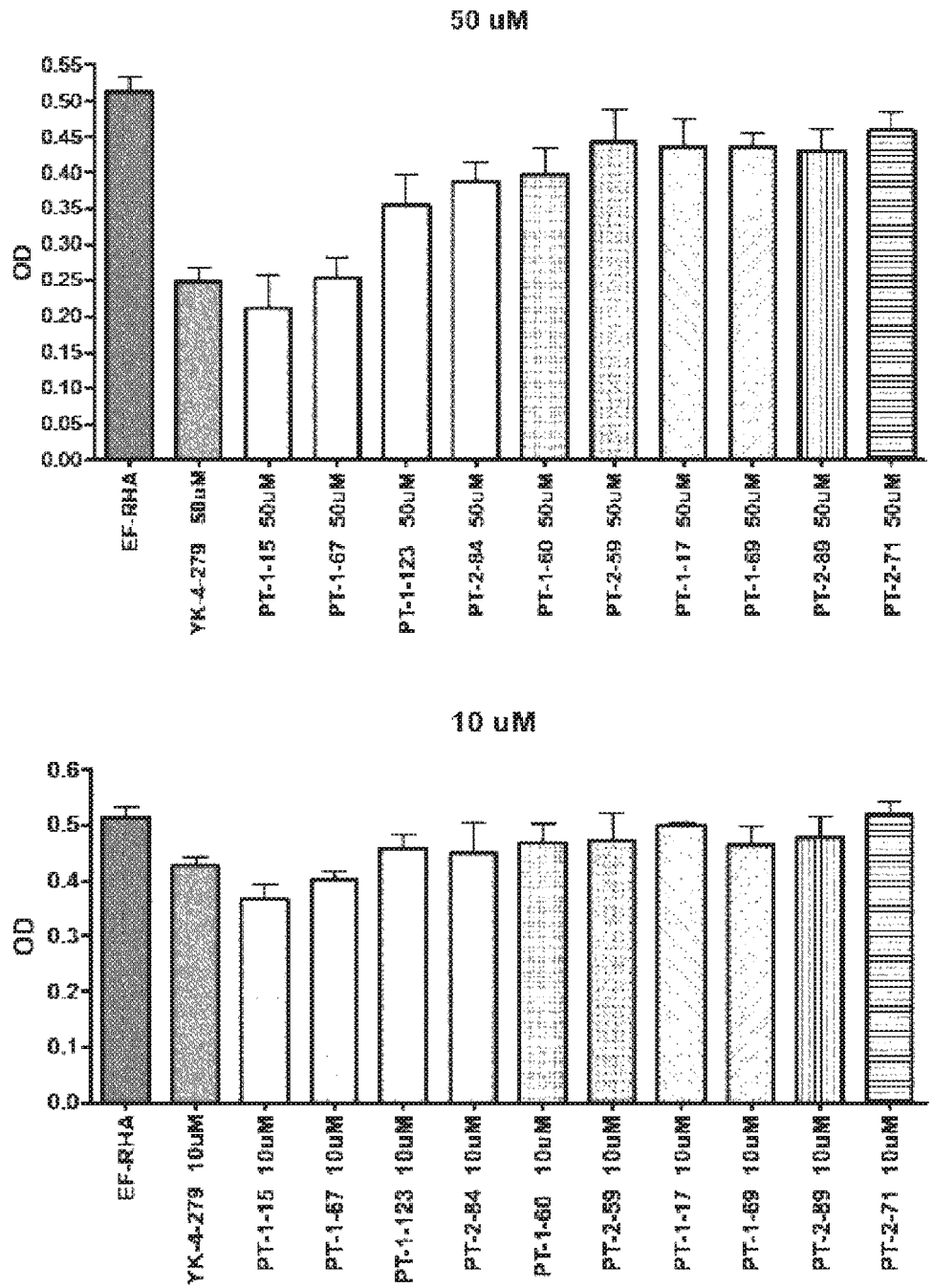
Figure 5C:
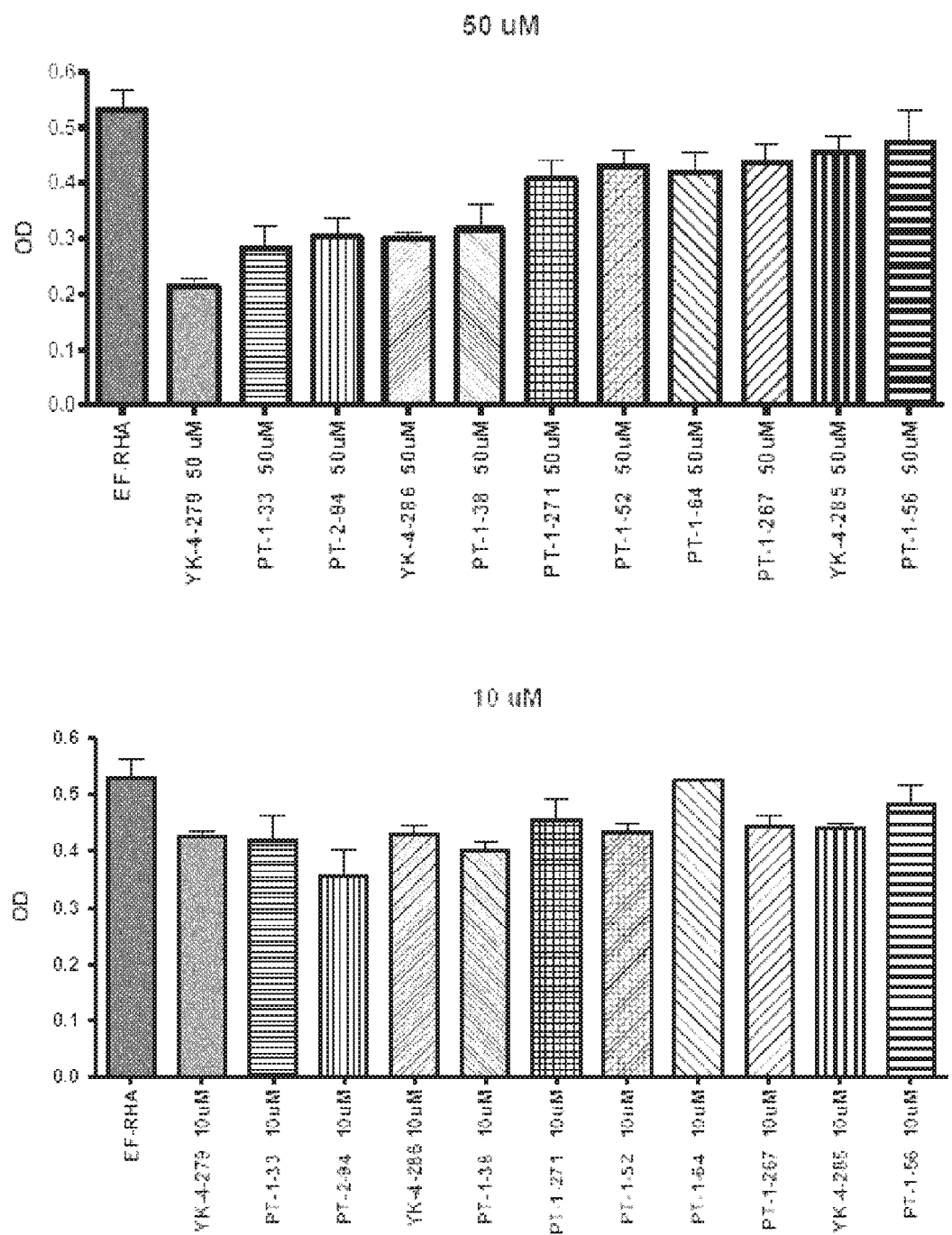
Figure 5D:
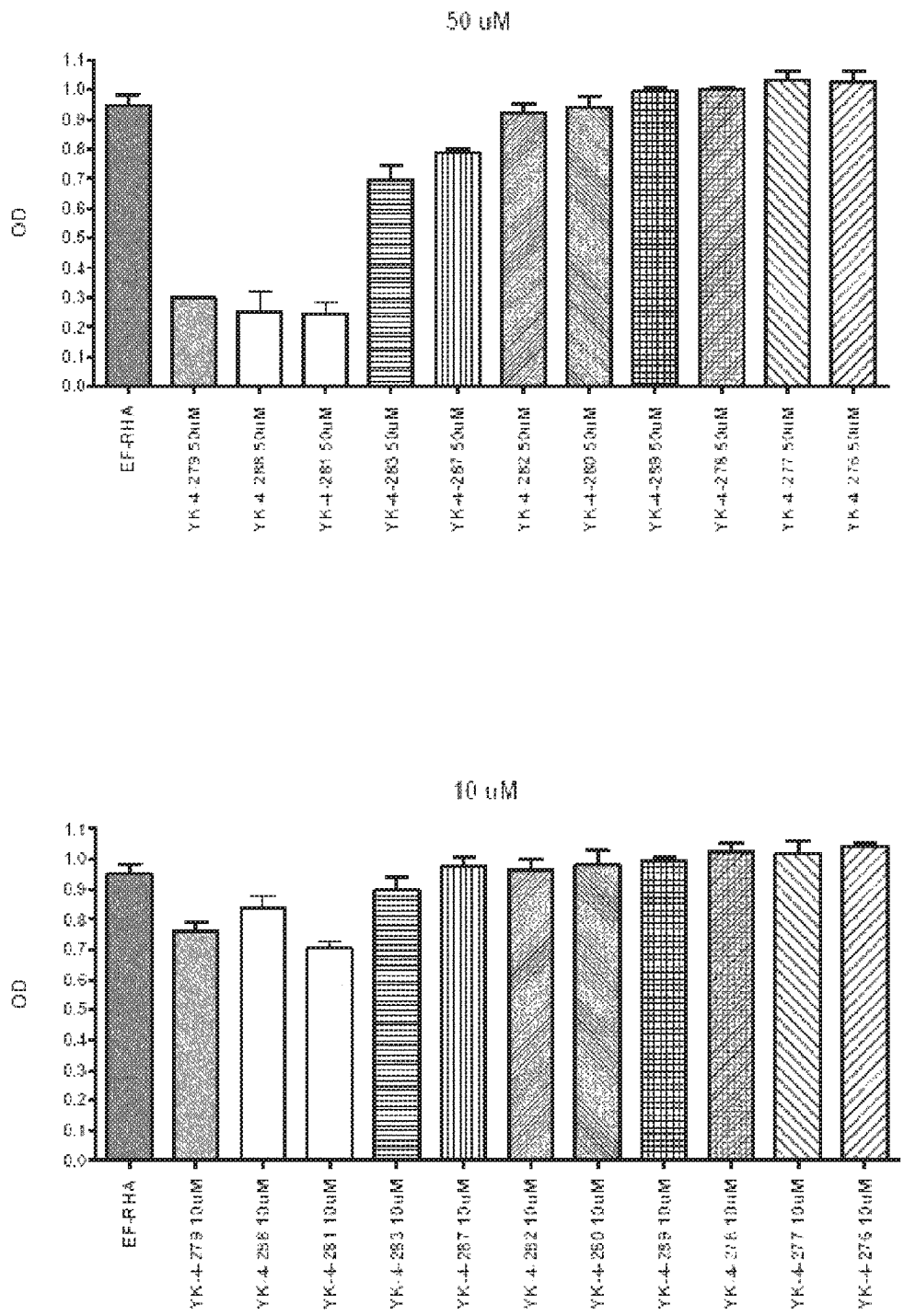
Figure 5E:
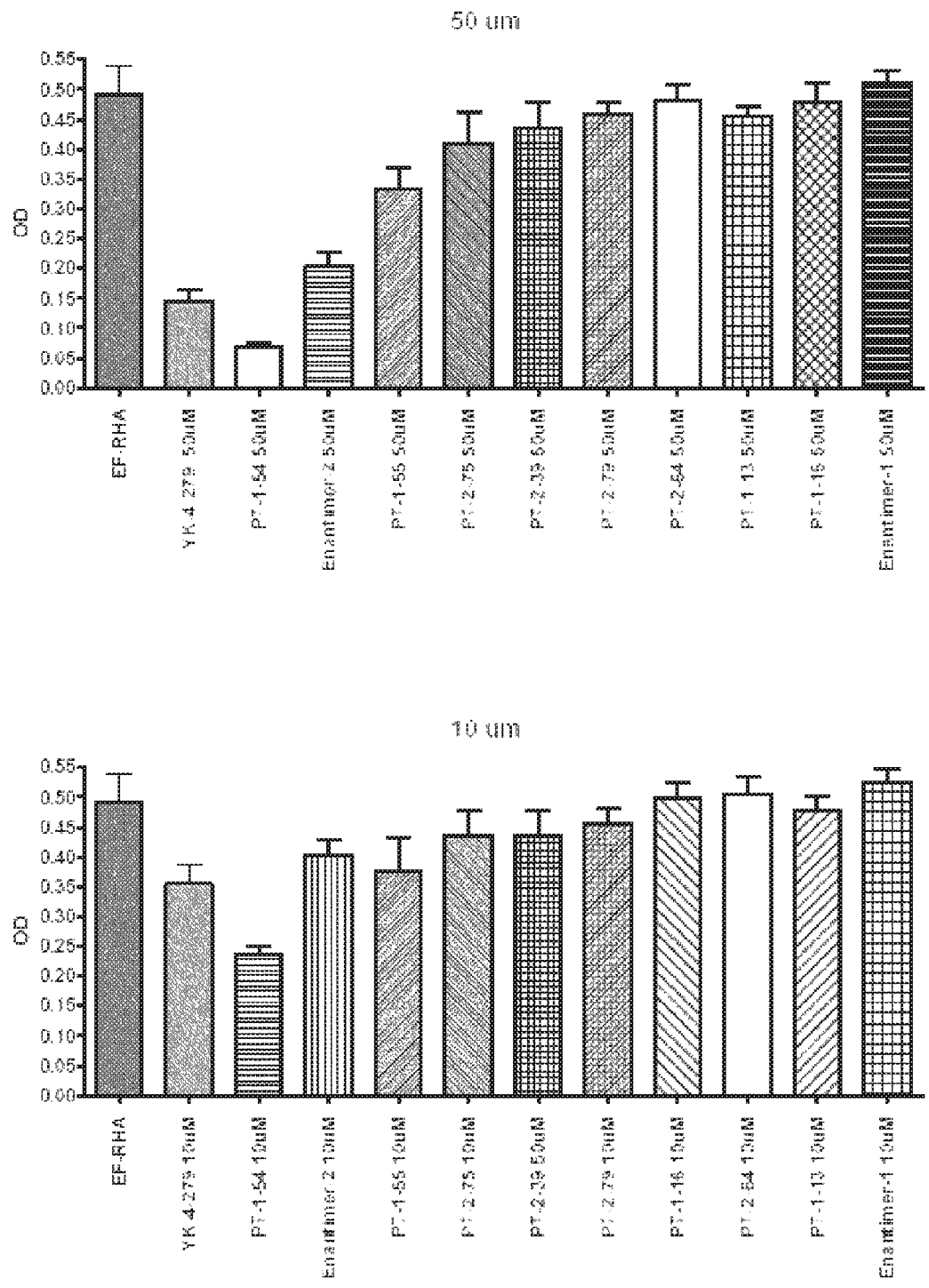
Figure 5F:
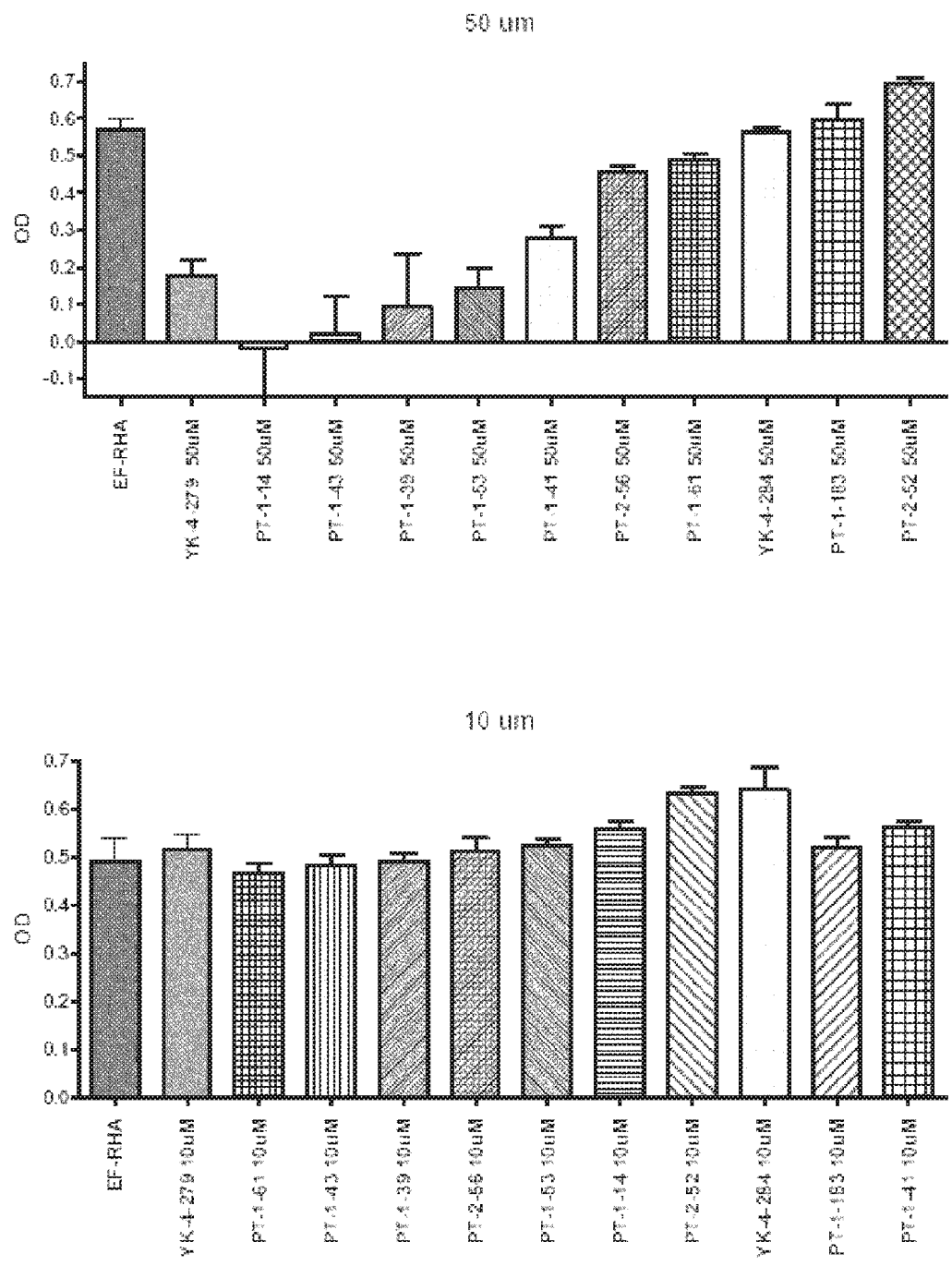
Figure 5G:
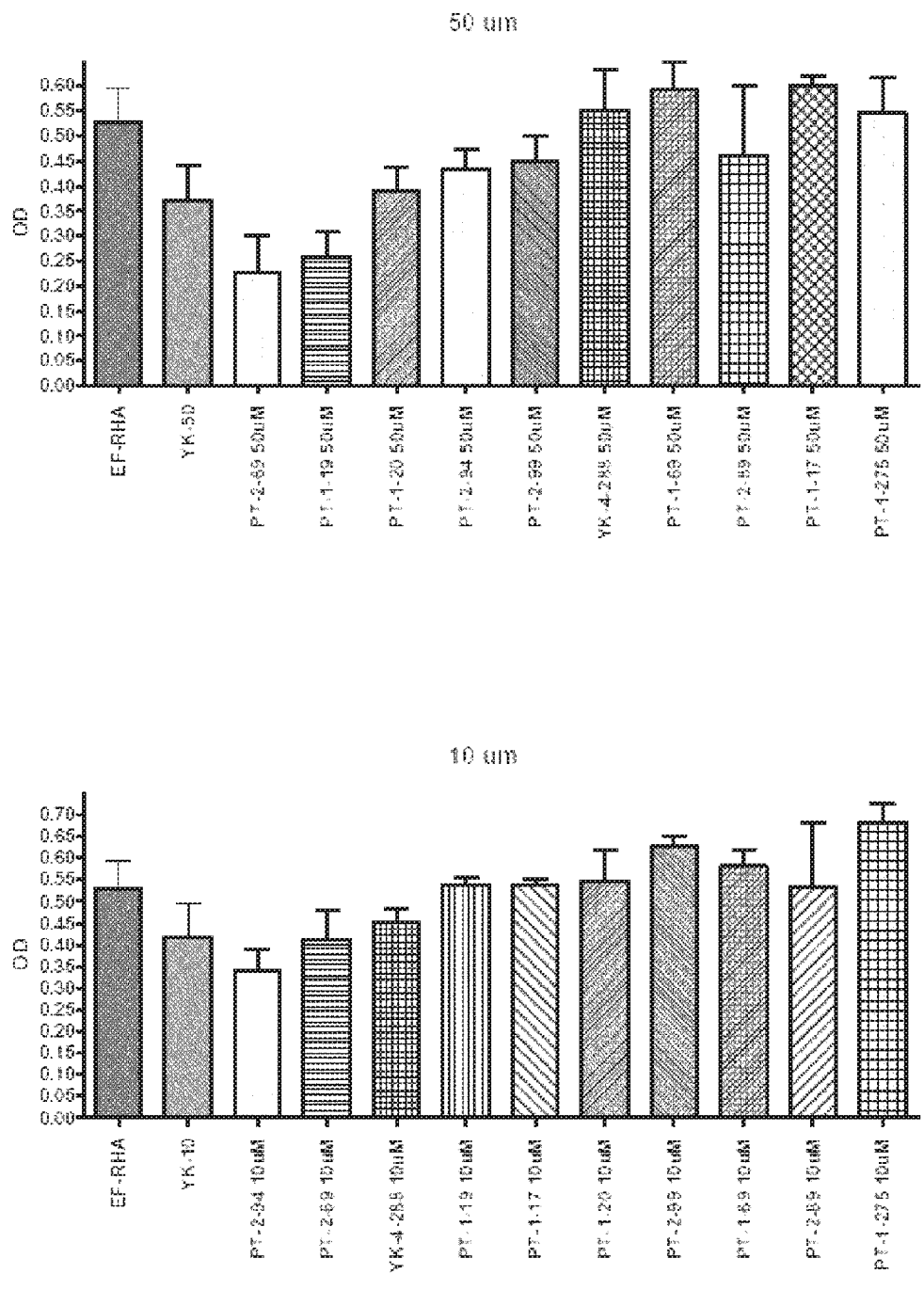

Wells in a 96-well plate were incubated with 100 µl/well 20 nM EWS-FLI1 protein solution (1M imidazole, 20 mM Tris, 500 mM NaCl) overnight at 4° C. Plates were washed with PBS, blocked with 150 µl/well 4% BSA for at least 2 h at room temperature, and then washed again with ELISA wash solution (PBS+0.1% T20, 200 µl/well). Plates were incubated for 1 hour at room temperature with 100 µl/well candidate agent in PBS (10 µM or 50 µM final), or DMSO control. Plates were incubated overnight at 4° C. with 100 µl/well 20 nM His-RHA protein solution (0.5 M imidazole, 125 mM NaCl, 20 mM Tris), and then washed with ELISA wash solution (PBS+0.1% T20, 200 µl/well). RHA bound to the plates was detected by incubating plates for 1 hour at room temperature with 100 µl/well primary anti-RHA antibody (1:1000 goat Anti-DHX9/EB09297, Everest), and then washing with ELISA wash solution (PBS+0.1% T20, 200 µl/well). Primary antibody was detected by incubating plates for 1 hour at room temperature with 100 µl/well secondary anti-goat antibody (1:500 donkey anti-goat IgG-HRP: sc-2020), and then washing with ELISA wash solution (PBS+0.1% T20, 200 µl/well). A horseradish peroxidase assay kit was used to determine the amount of secondary anti-goat antibody in each well (Bio-Rad-TMB Peroxidase EIA Substrate Kit #172-1066), with plates read at 450 nm. A relatively lower optical density indicating lower amounts of HRP indicate a candidate agent with increased inhibitory activity for EWS-FLI1-RHA binding. The results are summarized in FIGS. 5A-5G. FIG. 5A summarizes results for the following candidate molecules: YK-4-275, YK-4-285, PT-1-12, PT-1-18, PT-1-19, PT-1-20, PT-1-21, PT-1-22, PT-1-23, PT-1-175. FIG. 5B summarizes results for the following candidate molecules: PT-2-84, PT-2-59, PT-1-17, PT-2-71, PT-2-89, PT-1-123, PT-1-15, PT-1-60, PT-1-67, PT-1-69. FIG. 5C summarizes results for the following candidate molecules: YK-4-285, YK-4-286, PT-1-33, PT-1-38, PT-1-271, PT-1-52, PT-1-56, PT-1-64, PT-2-94, PT-1-267). FIG. 5D summarizes results for the following candidate molecules: YK-4-282, YK-4-287, YK-4-2 80, YK-4-289, YK-4-288, YK-4-278, YK-4-276, YK-4-283, YK-4-277, YK-4-281 FIG. 5E summarizes results for the following candidate molecules: PT-1-54, YK-4-279 (S), YK-4-279 (R), PT-1-55, PT-2-75, PT-2-39, PT-2-79, PT-1-16, PT-1-13, PT-2-64. FIG. 5F summarizes results for the following candidate molecules: YK-4-284, PT-1-14, PT-1-39, PT-1-41, PT-1-43, PT-1-53, PT-2-56, PT-2-52, PT-1-61, PT-1-183. FIG. 5G summarizes results for the following candidate molecules: PT-1-275, PT-2-69, PT-2-99, YK-4-288, PT-1-19, PT-1-20, PT-1-69, PT-2-89, PT-1-17, PT-2-94.

Example 9—Disruption of EWS-FLI1 Transcription Factor Activity

Figure 6A:
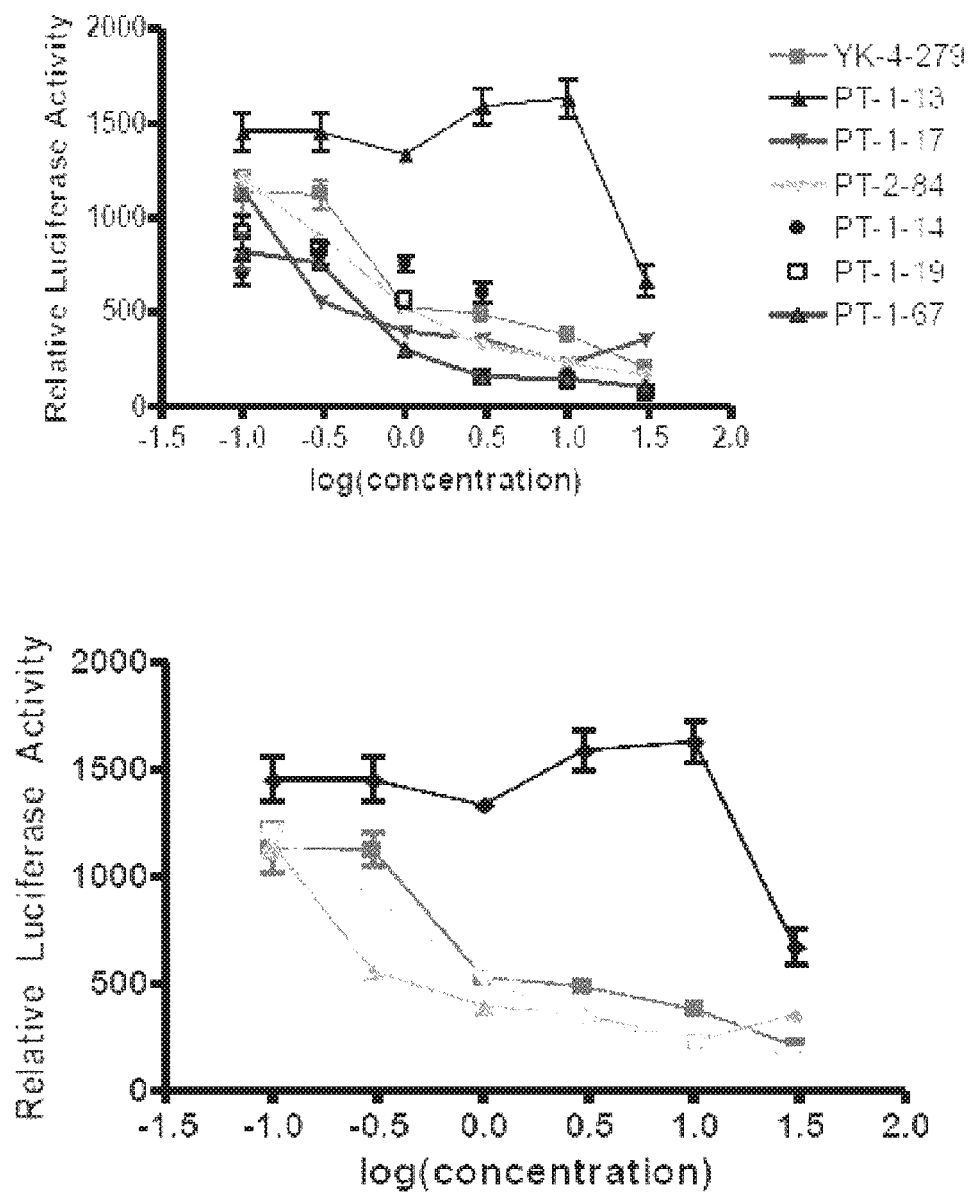
FIG. 6A and FIG. 6B are graphs showing general trends for relative luciferase activity for various concentrations of candidate agents in luciferase assays measuring inhibition of EWS-FLI1 binding to the NROB1 promoter.
Figure 6B:
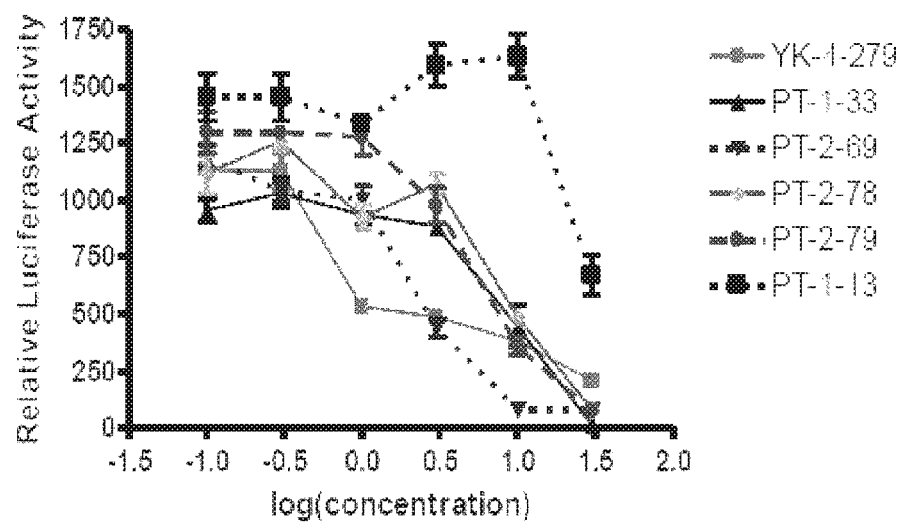
Figure 6B:
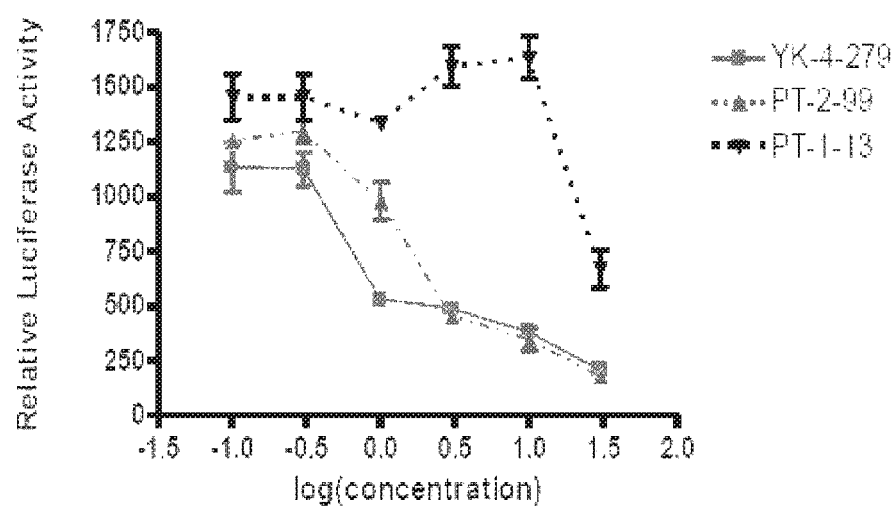
Figure 7A:
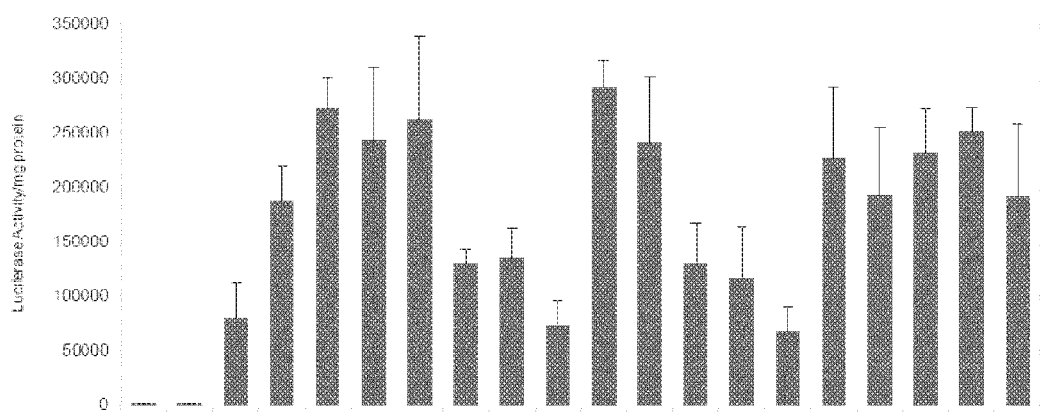
FIG. 7A-FIG. 7I illustrate luciferase activity for various concentrations of candidate agents in luciferase assays measuring inhibition of EWS-FLI1 binding to the NROB1 promoter.
Figure 7B:
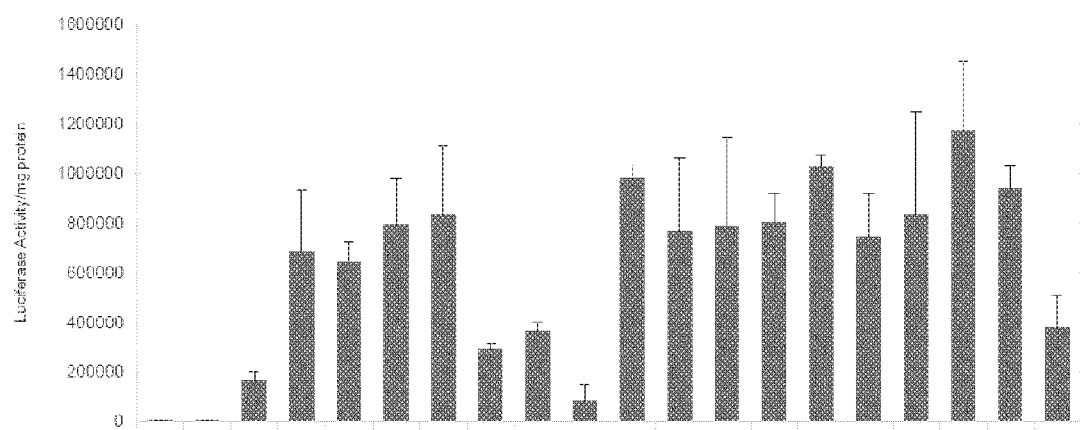
Figure 7C:
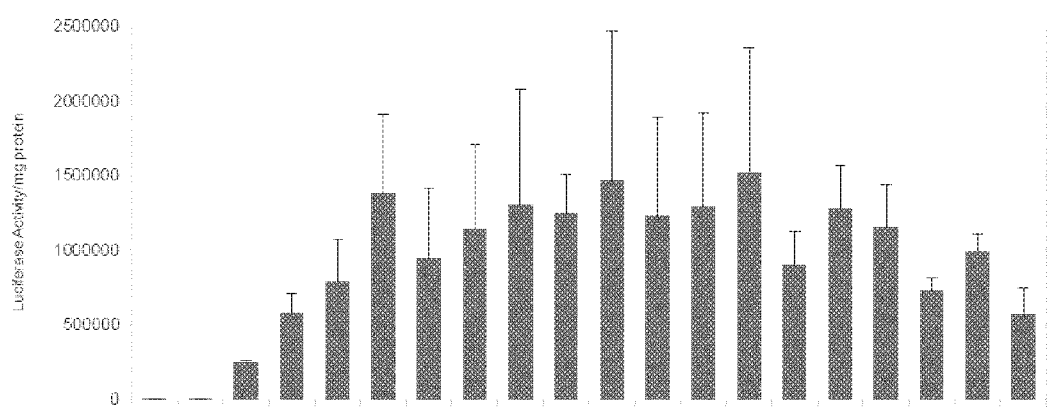
Figure 7D:
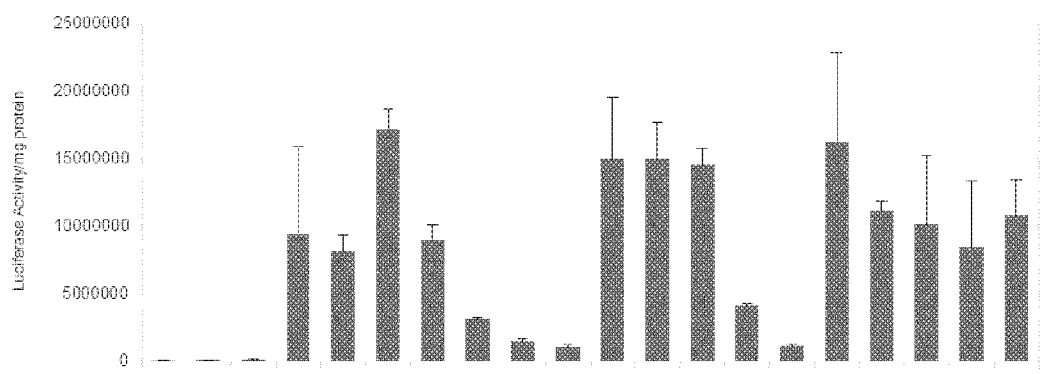
Figure 7E:
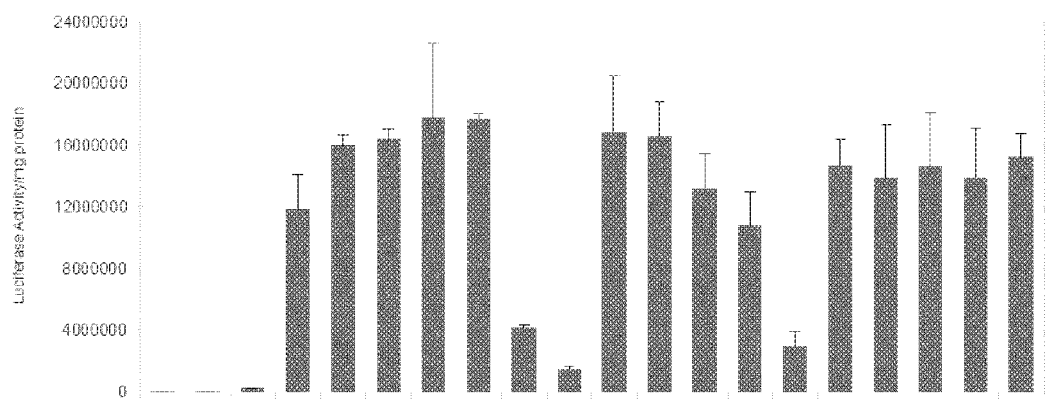
Figure 7F:
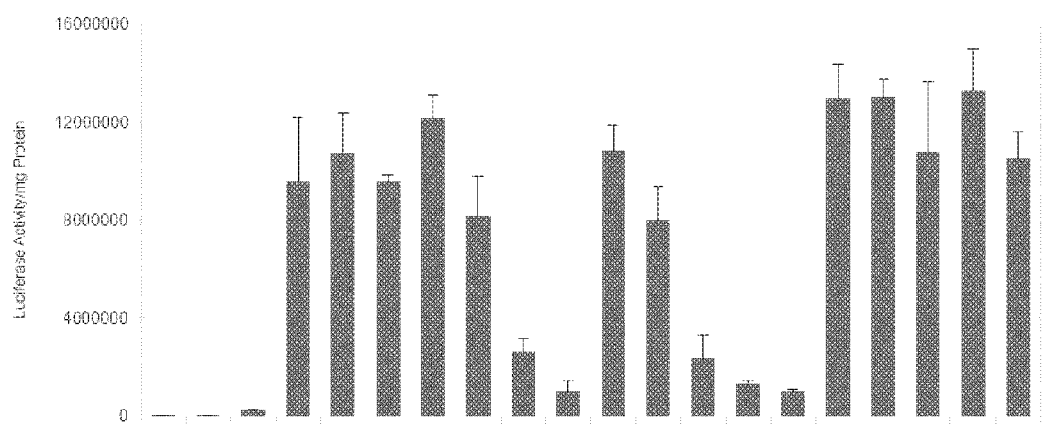
Figure 7G:
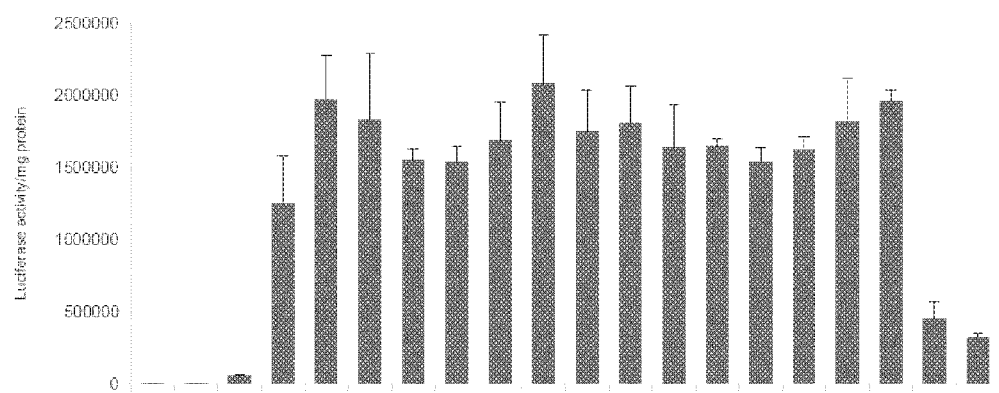
Figure 7H:
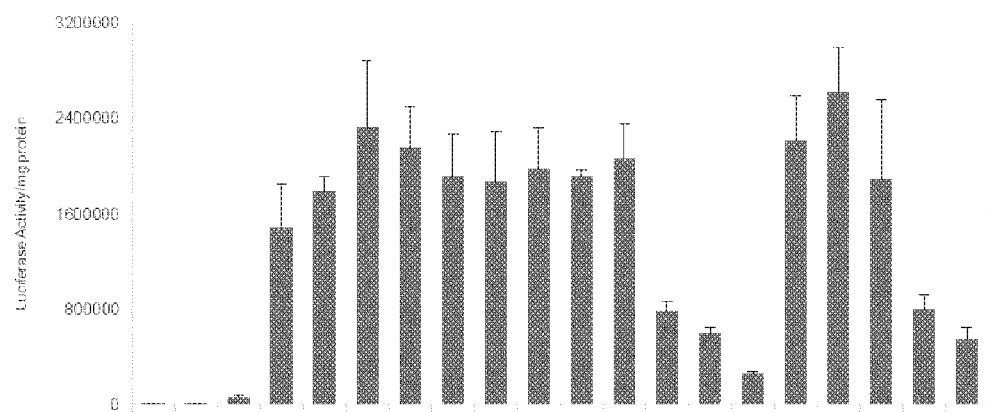
Figure 7I:
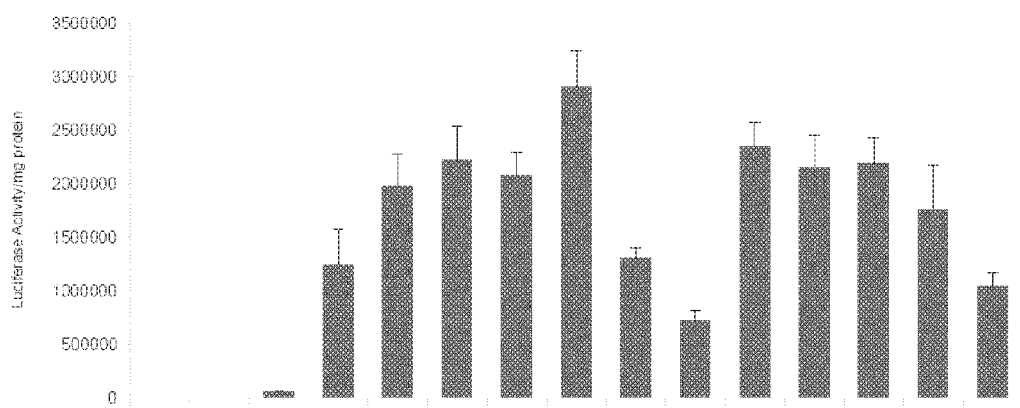

The activity of candidate small molecules to disrupt EWS-FLI1 transcription factor activity was screened using a luciferase assay in which EWS-FLI1 binding to the NROB1 promoter increases luciferase expression. Briefly, cells were transfected with a vector containing the NROB1 promoter driving luciferase expression, and an EWS-FLI1 expression vector. Transfected cells were treated with various concentrations of a candidate agent, and any change in the relative level of luciferase expression was determined. COS7 cells were plated in 96-well plates and transfected with pciNEO/EF vector and pGL3-NROB1. Controls included transfections with each vector only. Transfected cells were treated with various concentrations of a candidate agent, and treated cells were assays for luciferase activity. Decreased luciferase activity indicates a candidate agent with inhibitory activity in EWS-FLI1 acting as a transcription factor, promoting transcription of luciferase. FIG. 6A and FIG. 6B show general trends for relative luciferase activity for various concentrations of candidate agents. FIGS. 7A-71 show inhibitory activity for various concentrations of candidate agents.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method of preparing a compound of Formula I:

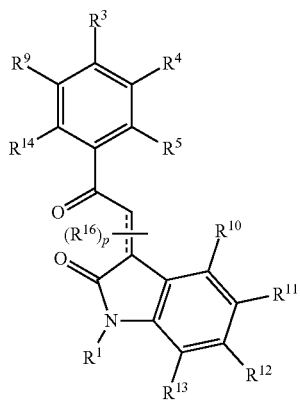

(I)

wherein $R^1$ is selected from the group consisting of hydrogen, $C_{1-6}$ alkyl, one amino acid, two amino acids linked together, three amino acids linked together,

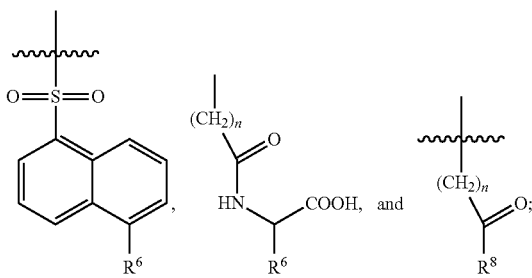

$R^3$ is selected from the group consisting of hydrogen, halogen, $C_{1-6}$ alkyl, $C_{1-6}$ alkoxy, —C(=O)NH$_2$, —NO$_2$, —NH$_2$, —OH, —N($R^{15}$)$_2$, and —S$R^{15}$;

$R^4$, $R^5$, $R^9$, and $R^{14}$ are each independently selected from the group consisting of hydrogen, halogen, $C_{1-6}$ alkyl, $C_{1-6}$ alkoxy, —C(=O)NH$_2$, —NO$_2$, —NH$_2$, —OH, —NH($R^{15}$), —N($R^{15}$)$_2$, and —S$R^{15}$;

$R^{10}$ is selected from the group consisting of halogen, $C_{1-6}$ alkyl, $C_{1-6}$ alkoxy, —C(=O)NH$_2$, —NO$_2$, —NH$_2$, —OH, —NH($R^{15}$), —N($R^{15}$)$_2$, and —S$R^{15}$;

$R^{11}$, $R^{12}$, and $R^{13}$ are each independently selected from the group consisting of hydrogen, halogen, $C_{1-6}$ alkyl, $C_{1-6}$ alkoxy, —C(=O)NH$_2$, —NO$_2$, —NH$_2$, —OH, —NH($R^{15}$), —N($R^{15}$)$_2$, and —S$R^{15}$;

$R^6$ is $C_{1-6}$ dialkyl amine;

$R^7$ is selected from the group consisting of hydrogen and $C_{1-6}$ alkyl;

$R^8$ and $R^{15}$ are each independently $C_{1-6}$ alkyl;

each $R^{16}$ is independently hydrogen, —OH;

n is an integer from 0 to 4;

p is 1 or 3; and the dashed line represents an optional double bond where said double bond has a configuration selected from the group consisting of cis and trans, with the proviso that at least one of $R^4$, $R^5$, $R^9$, and $R^{14}$ is selected from the group consisting of —NH($R^{15}$), —N($R^{15}$)$_2$, and —S$R^{15}$ or $R^3$ is selected form the group consisting of —N($R^{15}$)$_2$, and S$R^{15}$;

the method comprising: condensing a substituted acetophenone with a substituted isatin.

2. The method of claim 1, wherein the substituted isatin is a 4,7-dichloroisatin.

3. The method of claim 1, wherein the condensation is performed in the presence of a catalytic amount of a diethylamine.

4. The method of claim 1, further comprising dehydrating the product of the condensation.

5. The method of claim 1, wherein the compound is:

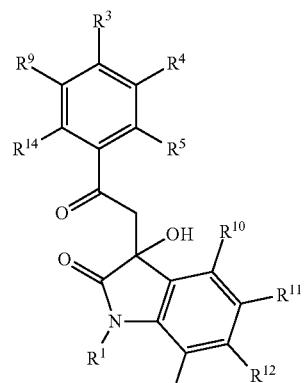

(Ia)

or a pharmaceutically acceptable salt thereof.

6. The method of claim 1, wherein the compound is:

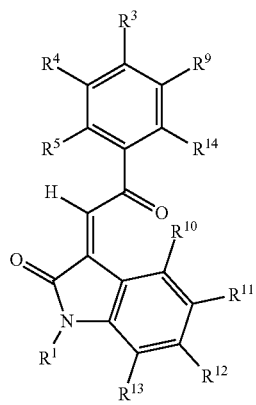

(Ib)

or a pharmaceutically acceptable salt thereof.

7. The method of claim 1, wherein $R^1$ is selected from the group consisting of Leu, Leu-Asp, Leu-Asp-Ala, —CH$_2$—C(=O)—NHCH$_2$COOH, —CH$_2$—C(=O)—(CH$_2$)C(CH$_3$)$_2$,

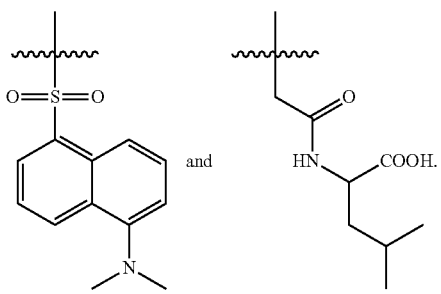 [SMILES: *S(=O)(=O)c1cccc2c(N(C)C)cccc12 ; *CC(=O)NC(CC(C)C)C(=O)O]

8. The method of claim 1, wherein the compound is selected from the group consisting of:

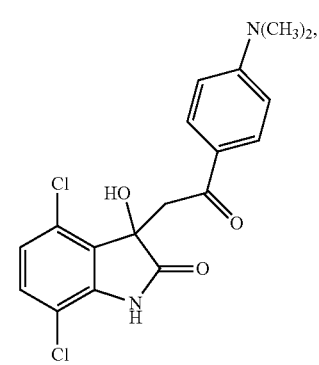

,

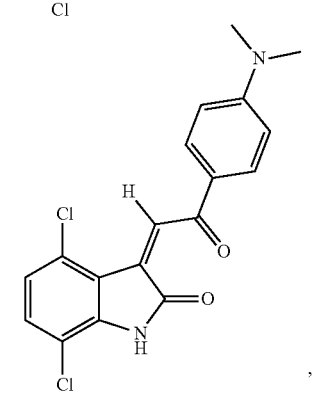

,

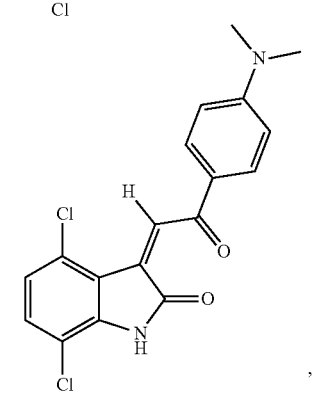

, and

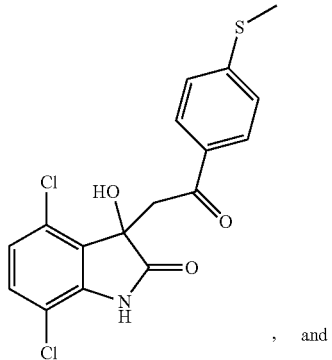

.

9. The method of claim 1, wherein $R^3$ is selected from $-N(R^{15})_2$, and $-SR^{15}$.

10. The method of claim 1, wherein $R^3$ is $-N(CH_3)_2$.

11. The method of claim 1, wherein $R^3$ is $-SCH_3$.

12. The method of claim 1, wherein the compound is:

13. The method of claim 1, wherein the compound is:

14. A method of treating a cancer selected from pancreatic cancer or Ewing's sarcoma, the method comprising administering an effective amount of a compound of Formula (I) in combination with an additional chemotherapeutic agent to a subject in need thereof, wherein the compound of Formula (I) is:

(I)

wherein $R^1$ is selected from the group consisting of hydrogen, $C_{1-6}$ alkyl, one amino acid, two amino acids linked together, three amino acids linked together,

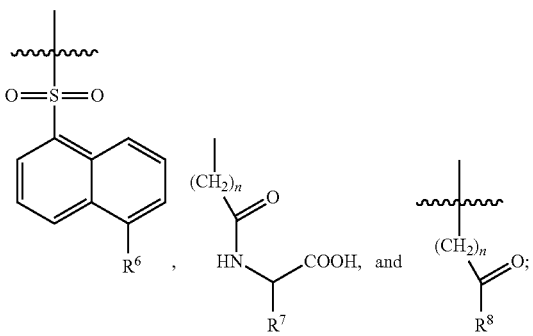

$R^3$ is selected from the group consisting of hydrogen, halogen, $C_{1-6}$ alkyl, $C_{1-6}$ alkoxy, —C(═O)NH$_2$, —NO$_2$, —NH$_2$, —OH, —N(R$^{15}$)$_2$, and —SR$^{15}$;

$R^4$, $R^5$, $R^9$, and $R^{14}$ are each independently selected from the group consisting of hydrogen, halogen, $C_{1-6}$ alkyl, $C_{1-6}$ alkoxy, —C(═O)NH$_2$, —NO$_2$, —NH$_2$, —OH, —NH(R$^{15}$), —N(R$^{15}$)$_2$, and —SR$^{15}$;

$R^{10}$ is selected from the group consisting of halogen, $C_{1-6}$ alkyl, $C_{1-6}$ alkoxy, —C(═O)NH$_2$, —NO$_2$, —NH$_2$, —OH, —NH(R$^{15}$), —N(R$^{15}$)$_2$, and —SR$^{15}$;

$R^{11}$, $R^{12}$, and $R^{13}$ are each independently selected from the group consisting of hydrogen, halogen, $C_{1-6}$ alkyl, $C_{1-6}$ alkoxy, —C(═O)NH$_2$, —NO$_2$, —NH$_2$, —OH, —NH(R$^{15}$), —N(R$^{15}$)$_2$, and —SR$^{15}$;

$R^6$ is $C_{1-6}$ dialkyl amine;

$R^7$ is selected from the group consisting of hydrogen and $C_{1-6}$ alkyl;

$R^8$ and $R^{15}$ are each independently $C_{1-6}$ alkyl;

each $R^{16}$ is independently hydrogen, —OH;

n is an integer from 0 to 4;

p is 1 or 3; and the dashed line represents an optional double bond where said double bond has a configuration selected from the group consisting of cis and trans, with the proviso that at least one of $R^4$, $R^5$, $R^9$, and $R^{14}$ is selected from the group consisting of —NH(R$^{15}$), —N(R$^{15}$)$_2$, and —SR$^{15}$ or $R^3$ is selected form the group consisting of —N(R$^{15}$)$_2$, and SR$^{15}$.

15. The method of claim 14, wherein the additional chemotherapeutic agent is selected from the group consisting of a *vinca* alkaloid, an anthracycline, an anthracene an epipodophyllo-toxin, actinomyocin D, mithomycin C, mitramycin, methotrexate, docetaxel, etoposide (VP-16), paclitaxel, docetaxel, adriamycin, an immunosuppressant, a histone deacetylase inhibitor (HDAC), an aurora kinase inhibitor, a demethylating agent, an Ewing antigen antibody, and hydroxyurea.

16. The method of claim 15, wherein the *vinca* alkaloid is selected from the group consisting of vinblastine and vincristine.

17. The method of claim 14, wherein the cancer is pancreatic cancer.

18. The method of claim 14, wherein the cancer comprises a translocation in the EWS gene.

19. The method of claim 14, wherein the subject is mammalian.

20. The method of claim 14, wherein the cancer is Ewing's sarcoma.

* * * * *

UNITED STATES PATENT AND TRADEMARK OFFICE
CERTIFICATE OF CORRECTION

PATENT NO.         : 9,714,222 B2
APPLICATION NO.    : 15/040840
DATED              : July 25, 2017
INVENTOR(S)        : Jeffrey A. Toretsky It is certified that error appears in the above-identified patent and that said Letters Patent is hereby corrected as shown below:

On the Title Page

In Column 2 (item (56)) at Line 13, Under Other Publications, change "adol" to --aldol--.

In Column 2 (item (56)) at Line 30, Under Other Publications, change "hyroxy" to --hydroxy--.

In Column 2 (item (56)) at Line 32, Under Other Publications, change "Hetercycles:" to --Heterocycles:--.

In Column 2 (item (56)) at Line 35, Under Other Publications, change "Pharmazle" to --Pharmazole--.

In Column 2 (item (56)) at Line 45, Under Other Publications, change "2(IH)" to --2(1H)--.

In Column 2 (item (56)) at Line 52, Under Other Publications, change "Recommentations" to --Recommendations--.

In Column 1 (page 2, item (56)) at Line 7, Under Other Publications, change "3-hyrdrozyoxindoles"" to --3-hydroxyoxindoles"--.

In Column 1 (page 2, item (56)) at Line 9, Under Other Publications, change "Alkyidene" to --Alkadiene--.

In Column 1 (page 2, item (56)) at Line 12, Under Other Publications, change "Tetrahetron" to --Tetrahedron--.

In Column 1 (page 2, item (56)) at Line 15, Under Other Publications, change "acrykuc" to --acrylic--.

Signed and Sealed this
Twenty-first Day of November, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,714,222 B2

In Column 1 (page 2, item (56)) at Line 35, Under Other Publications, change "trimethoxphenyl)" to --trimethoxyphenyl)--.

In Column 1 (page 2, item (56)) at Line 44, Under Other Publications, change "Hyrdoxy" to --Hydroxy--.

In Column 1 (page 2, item (56)) at Line 51, Under Other Publications, change "Neucleophilic" to --Nucleophilic--.

In Column 1 (page 2, item (56)) at Line 52, Under Other Publications, change "Flourine" to --Fluorine--.

In Column 1 (page 2, item (56)) at Line 57, Under Other Publications, change "(PubChm" to --(PubChem--.

In Column 1 (page 3, item (56)) at Line 40, Under Other Publications, change "Classsification" to --Classification--.

In Column 1 (page 3, item (56)) at Line 62, Under Other Publications, change "Sciene" to --Science--.

In Column 2 (page 3, item (56)) at Line 36, Under Other Publications, change "Bioconjug" to --Bioconjugate--.

In Column 1 (page 4, item (56)) at Line 3, Under Other Publications, change "assocation" to --association--.

In Column 1 (page 4, item (56)) at Line 22, Under Other Publications, change "Cyclohexonone" to --Cyclohexanone--.

In Column 1 (page 4, item (56)) at Line 42, Under Other Publications, change "Luekemia" to --Leukemia--.

In Column 1 (page 4, item (56)) at Line 59, Under Other Publications, change "oxoehyl]," to --oxoethyl],--.

In the Drawings

Sheet 11 of 24 (X-axis, Graph 1, FIG. 5E) at Line 4 (approx.), Change "Enantimer" to --Enantiomer--.

Sheet 11 of 24 (X-axis, Graph 1, FIG. 5E) at Line 12 (approx.), Change "Enantimer" to --Enantiomer--.

Sheet 11 of 24 (X-axis, Graph 2, FIG. 5E) at Line 4 (approx.), Change "Enantimer" to --Enantiomer--.

Sheet 11 of 24 (X-axis, Graph 2, FIG. 5E) at Line 12 (approx.), Change "Enantimer" to --Enantiomer--.

In the Specification

In Column 1 at Line 46, Change "(FLI)1" to --FLI1--.

In Column 1 at Line 54, Change "ESTF" to --ESFT--.

In Column 1 at Line 60, Change "EWS-FI1" to --EWS-FLI1--.

In Column 4 at Line 2, Change "—$SR^{15}$;" to -- —$SR^{15}$.--.

In Column 5 at Line 2, Change "of" to --of:--.

In Column 6 at Line 40, Change "NROB1" to --NR0B1--.

In Column 6 at Line 43, Change "NROB1" to --NR0B1--.

In Column 6 at Line 63, Change "EWS-FI1 interactin" to --EWS-FLI1 interacting--.

In Column 7 at Lines 13-17 (approx.), After " 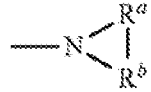 " insert --.--.

In Column 9 at Lines 63, Change "heteroalicyclylic" to --heteroalicyclic--.

In Column 13 at Line 13 (approx.), Change "(6)" to --($\delta$)--.

In Column 14 at Line 67, Change "$R^1$," to --$R^{11}$,--.

In Column 15 at Line 2, Change "$C_{1-6}$alkyl, $C_{1-6}$alkoxy," to --$C_{1-6}$ alkyl, $C_{1-6}$ alkoxy,--.

In Column 15 at Line 5, Change "$C_{1-6}$alkyl;" to --$C_{1-6}$ alkyl;--.

In Column 15 at Line 6, Change "$C_{1-6}$alkyl;" to --$C_{1-6}$ alkyl;--.

In Column 15 at Line 28, Change "—$SR^{15}$;" to -- —$SR^{15}$.--.

In Column 17 at Line 43, Change "spheroblasts." to --spheroplasts.--.

In Column 18 at Line 57, Change "ultramylopectin," to --ultraamylopectin,--.

In Column 19 at Line 23, Change "providone" to --povidone--.

In Column 19 at Line 26, After "doses" insert --.--.

CERTIFICATE OF CORRECTION (continued)
U.S. Pat. No. 9,714,222 B2

In Column 20 at Line 3, Change "cyclodextran." to --cyclodextrin.--.

In Column 21 at Line 19, Change "actinomyocin" to --actinomycin--.

In Column 21 at Line 19, Change "mithomycin" to --mitomycin--.

In Column 22 at Line 49, Change "EWS-Flil" to --EWS-FLI1--.

In Column 23 at Line 3, Change "EWS fli-1" to --EWS-FLI1--.

In Column 23 at Line 9, Change "Ara-C(Stegmaier" to --Ara-C (Stegmaier--.

In Column 23 at Line 54, Change "Onc" to --Oncol.--.

In Column 24 at Line 25, Change "aa" to --a--.

In Column 25 at Line 63, Change "pseudopaillary" to --pseudopapillary--.

In Column 26 at Line 22, Change "mesobalstic" to --mesoblastic--.

In Column 26 at Line 35, Change "11 q23)," to --11q23),--.

In Column 27 at Line 67, Change "3',4'OCH$_3$" to --3',4'-OCH$_3$--.

In Column 27 at Line 67, Change "3',5'OCH$_3$" to --3',5'-OCH$_3$--.

In Column 28 at Lines 1-2, Change "4'-OC$_2$H$_5$(PT-1-14);" to --4'-OC$_2$H$_5$ (PT-1-14);--.

In Column 28 at Lines 2-3, Change "4'-N(CH$_3$)$_2$(PT-1-17);" to --4'-N(CH$_3$)$_2$ (PT-1-17);--.

In Column 29 at Line 36 (approx.), Change "4.7" to --4,7--.

In Column 29 at Line 37 (approx.), Change "Pyiridine" to --Pyridine--.

In Column 60 at Line 35, Change "NROB1" to --NR0B1--.

In Column 60 at Line 36, Change "NROB1" to --NR0B1--.

In Column 60 at Line 42, Change "pGL3-NROB1." to --pGL3-NR0B1.--.

In Column 60 at Line 51, Change "7A-71" to --7A-7I--.

In the Claims

In Column 63 at Line 64, In Claim 1, change "form" to --from--.

CERTIFICATE OF CORRECTION (continued)
U.S. Pat. No. 9,714,222 B2

In Column 68 at Line 15, In Claim 15, change "actinomyocin" to --actinomycin--.

In Column 68 at Line 15, In Claim 15, change "mithomycin" to --mitomycin--.